US010475525B2

(12) United States Patent
Cashman et al.

(10) Patent No.: US 10,475,525 B2
(45) Date of Patent: Nov. 12, 2019

(54) METHODS AND SYSTEMS FOR PREDICTING MISFOLDED PROTEIN EPITOPES

(71) Applicant: The University of British Columbia, Vancouver (CA)

(72) Inventors: Neil R. Cashman, Vancouver (CA); Steven S. Plotkin, Vancouver (CA); William C. Guest, Vancouver (CA)

(73) Assignee: The University of British Columbia, Vancouver (CA)

( * ) Notice: Subject to any disclaimer, the term of this patent is extended or adjusted under 35 U.S.C. 154(b) by 335 days.

(21) Appl. No.: 14/997,951

(22) Filed: Jan. 18, 2016

(65) Prior Publication Data

US 2016/0132633 A1   May 12, 2016

Related U.S. Application Data

(62) Division of application No. 12/574,637, filed on Oct. 6, 2009, now abandoned.
(Continued)

(51) Int. Cl.
*G01N 33/48* (2006.01)
*G16B 5/00* (2019.01)
(Continued)

(52) U.S. Cl.
CPC .......... *G16B 5/00* (2019.02); *C07K 14/70596* (2013.01); *C07K 16/2863* (2013.01); *C07K 16/2872* (2013.01); *C07K 16/40* (2013.01); *C12N 9/0089* (2013.01); *C12N 9/12* (2013.01); *G06N 3/126* (2013.01); *G06N 7/005* (2013.01); *G16B 15/00* (2019.02);

*G16B 20/00* (2019.02); *A61K 2039/505* (2013.01); *C07K 2317/34* (2013.01); *C07K 2317/73* (2013.01);
(Continued)

(58) Field of Classification Search
None
See application file for complete search history.

(56) References Cited

U.S. PATENT DOCUMENTS 6,165,784 A    12/2000  O'Rourke et al.

FOREIGN PATENT DOCUMENTS

JP    7-501798       2/1995
JP    2003-504087    2/2003
(Continued)

OTHER PUBLICATIONS

Office Action dated May 9, 2016, in corresponding Japanese Patent Application No. 2014-119308, 8 pages.
(Continued)

*Primary Examiner* — Larry D Riggs, II
(74) *Attorney, Agent, or Firm* — Bereskin & Parr LLP; Carmela De Luca

(57) ABSTRACT

A method and system to identify an epitope unique to a misfolded form of a protein is provided. Sets of one or more amino acid residues are selected from a model representing the structure of the protein; the free energy of unfolding of each set is determined; and the epitope is identified from the sets having a total probability of unfolding above a minimum probability or a free energy of unfolding below a minimum energy. In other aspects, the invention provides for the use of epitopes identified by the epitope prediction methods, and related antibodies, to diagnose and treat disease and to screen samples for the presence of such epitopes.

15 Claims, 5 Drawing Sheets

Specification includes a Sequence Listing.

Related U.S. Application Data

(60) Provisional application No. 61/136,815, filed on Oct. 6, 2008, provisional application No. 61/156,807, filed on Mar. 2, 2009.

(51) Int. Cl.

| | | |
|---|---|---|
| *G16B 20/00* | (2019.01) | |
| *C07K 16/28* | (2006.01) | |
| *C07K 16/40* | (2006.01) | |
| *C07K 14/705* | (2006.01) | |
| *C12N 9/02* | (2006.01) | |
| *C12N 9/12* | (2006.01) | |
| *G06N 3/12* | (2006.01) | |
| *G06N 7/00* | (2006.01) | |
| *G16B 15/00* | (2019.01) | |
| *A61K 39/00* | (2006.01) | |

(52) U.S. Cl.
CPC ............... *C12Y 115/01001* (2013.01); *C12Y 207/10001* (2013.01)

(56) References Cited

FOREIGN PATENT DOCUMENTS

| JP | 2003-534000 | 11/2003 |
|----|-------------|---------|
| JP | 2005-023074 | 1/2005 |
| WO | 93/11155 | 6/1993 |
| WO | 01/05426 | 1/2001 |
| WO | 01/90191 | 11/2001 |

OTHER PUBLICATIONS

Office Action dated Dec. 21, 2017 (including English translation) in corresponding Japanese Patent Application No. 2014-119308, 12 pages.

Korth et al., "Prion (PrPSc)-specific epitope defined by a monoclonal antibody," Nature, Nov. 6, 1997, vol. 390, pp. 74-77.

Rubenstein et al., "Immune surveillance and antigen conformation determines humoral immune response to the prion protein immunogen," Journal of NeuroVirology (1999) 5, 401-413.

JP2005-023074 Machine Translation, 24 pages.

Sachsamanoglou et al., "Antigenic profile of human recombinant PrP: generation and characterization of a versatile polyclonal antiserum," Journal of Neuroimmunology 146 (2004) 22-32.

Serbec et al., "Monoclonal Antibody against a Peptide of Human Prion Protein Discriminates between Creutzfeldt-Jacob's Disease-affected and Normal Brain Tissue," The Journal of Biological Chemistry, vol. 279, No. 5, Jan. 30, 2004, pp. 3694-3698.

Kim et al., "Antigenic characterization of an abnormal isoform of prion protein using a new diverse panel of monoclonal antibodies," Virology 320 (2004) 40-51.

Thackray et al., "Modification of blood cell PrP epitope exposure during prion disease," Biochem J. (2005) 390, 563-571.

Choi et al., "Generation of Monoclonal Antibody Recognized by the GXXXG Motif (Glycine Zipper) of Prion Protein," Hybridoma, vol. 25, No. 5, 2006, pp. 271-278.

Privat et al., "Human prion diseases: from antibody screening to a standardized fast immunodiagnosis using automation," Modern Pathology (2008) 21, 140-149.

Yuan J et al. Accessibility of a critical prion protein region involved in strain recognition and its implications for the early detection of prions, CMLS Cellular and Molecular Life Sciences, Jan. 15, 2008, vol. 65, No. 4, pp. 631-643.

Zou W et al. Acidic pH and Detergents Enhance in Vitro Conversion of Human Brain PrPC to a PrPSC-Like Form, Journal of Biological Chemistry, American Society for Biochemistry and Molecular Biology, US, Aug. 2, 2002, vol. 277, No. 46, pp. 43942-43947.

Cashman N et al. A Prion-Specific Immunological Epitope, Abstracts of the Annual Meeting of the Society for Neuroscience, Society for Neuroscience, Washington, DC, US, Jan. 1, 2001, vol. 27, No. 2, p. 1743.

Mornon J et al. Structural features of prions explored by sequence analysis. II. A PrP Sc model, Cellular and Molecular Life Sciences, vol. 59, No. 12, Dec. 2002, pp. 2144-2154.

METHODS AND SYSTEMS FOR PREDICTING MISFOLDED PROTEIN EPITOPES

This application is a divisional application of U.S. patent application Ser. No. 12/574,637, filed Oct. 6, 2009, which claims the benefit of U.S. Provisional Application Nos. 61/136,815 filed Oct. 6, 2008 and 61/156,807 filed Mar. 2, 2009, the full disclosures of each of these is incorporated herein by reference.

SEQUENCE LISTING

The following application contains a sequence listing in computer readable format (CRF), identical to that submitted with U.S. patent application Ser. No. 12/574,637, filed Oct. 6, 2009. The content of that CRF is hereby incorporated by reference.

FIELD OF THE INVENTION

The present invention provides methods and systems for identifying epitopes. More specifically, the invention provides methods and systems for identifying epitopes unique to a misfolded form of a protein.

BACKGROUND OF THE INVENTION

The endoplasmic reticulum (ER) is a specialized folding environment in which nearly one-third of the proteins encoded by a eukaryotic genome are translocated and folded as either luminal secreted proteins or transmembrane proteins. Proteins are exported from the ER by the concatamer complex II (COPII) machinery which generates transport vesicles for delivery of cargo to the Golgi (Lee et al., Annu. Rev Cell Dev. Biol. 20, 87 (2004)). The ER-associated folding (ERAF) pathways are also coordinated with ER-associated degradation (ERAD) pathways whereby misfolded proteins are targeted for translocation to the cytosolic proteasome system (Wegele et al., Rev Physiol Biochem Pharmacol 151, 1 (2004); Young et al., Trends Biochem. Sci. 28, 541 (2003)). For cytosolic proteins, there is also protein folding quality control system involving molecular chaperones and the ubiquitin-proteosomal and autophagic degradation pathways (Kubota, J. Biochem. (2009)).

Numerous misfolding diseases occur when normally folded protein expressed on the cell surface, extracellular environment or the cytosol misfolds due to pathologic conditions, resulting in misfolded aggregates. Neurodegenerative diseases, such as Alzheimer's disease (AD), amyotrophic lateral sclerosis (ALS) and Parkinson's disease/Lewy body disease (PD, LBD) are associated with neural deposits of misfolded aggregates of normal protein, including tau and the Aβ fragment of the amyloid precursor protein (APP) in AD; superoxide dismutase-1 (SOD1) in ALS; and α-synuclein in PD and LBD. Misfolding of the cellular prion protein, a cell surface glycoprotein expressed in nervous system and other tissues, is implicated in Creutzfeldt-Jakob disease (CJD) of sporadic and familial origin, Gerstmann-Straussler-Scheinker syndrome (GSS), kuru, and fatal familial insomnia (FFI). The normally folded prion protein (denoted $PrP^C$) can adopt a pathogenic misfolded conformation induced by physical contact with the disease-misfolded prion protein (generically denoted $PrP^{Sc}$) in a process designated template-directed misfolding. The tertiary and secondary structure of $PrP^{Sc}$ differs substantially from that of $PrP^C$ leading to solvent exposure of previously buried residues that in this invention are used as the basis for distinguishing one form from the other. The original aggregate of misfolded prion protein that seeds the misfolding process can either arise endogenously, as in sporadic CJD, or be acquired as an infectious agent from another animal or human, as in variant and iatrogenic CJD. In the former case, certain inherited mutations of the Prion Protein gene (PRNP) coding sequence can predispose individuals to misfolding of $PrP^C$ and trigger clinical manifestations of the disease. At present, there is no curative therapy for prion disease, resulting in a mortality rate of 100% (Prusiner, Ann Rev Microbiol 48, 655 (1994)). Prion protein is implicated in animal diseases as well. Those of economic interest include bovine spongiform encephalopathy (BSE) of cattle, scrapie of sheep, and chronic wasting disease of cervids. As with human disease, there is no effective treatment or vaccine prevention for animal prion diseases.

Protein misfolding diseases are not limited to those of the central nervous system. The misfolding and aggregation of the thyroid hormone carrier protein transthyretin (TTR) is involved in familial amyloid polyneuropathy and senile systemic amyloidosis (Benson and Kincaid, Muscle Nerve 36 (4), 411 (2007)). Patients on protracted hemodialysis for kidney failure may suffer from renal accumulation of $β_2$ microglobulin amyloid deposits, a component of the type 1 major histocompatibility complex (MHC) present on most cells of the body (Winchester et al, Adv Ren Replace Ther 10(4), 279 (2003)).

Diseases of protein aggregation can be considered in two broad classes: those involving natively unstructured proteins or peptides (e.g., alpha synuclein and Aβ respectively), and those involving proteins possessing structured domains (e.g., $PrP^C$ and TTR). According to one hypothesis, natively structured proteins are thought to have been evolutionarily selected to remain soluble in physiological conditions; i.e., they do not spontaneously aggregate.

Protein misfolding also occurs in cancerous cells where a generalized decline in folding fidelity results in misfolded protein residing at the cell surface. In cancer cells, dysregulation of cell cycle control results in their uncontrolled proliferation. Left unchecked, the growth and dispersion of these cells through metastasis can cause anatomic and functional derangement of organs and compete for vital nutrients. A normal human cell is subject to careful regulatory control by many signalling mechanisms to prevent division except when needed for tissue repair or renewal. Cancerous cells accumulate somatic mutations that render them insensitive to these signals. A consequence of these and other mutations is a decline in protein folding quality control: a healthy cell is able to recognize and destroy synthesized protein that has not correctly folded, but some cancer cells display reduced fidelity and monitoring of folding which can lead to incorporation of misfolded proteins into the plasma membrane (reviewed in Nature Vol 426 No 6968 pp 883-909). The ectodomains of these misfolded proteins expose to the extracellular environment protein surfaces that are normally buried in the molecular interior, and as such present epitopes for selective identification. Thus misfolded cell surface proteins can provide a diagnostic tool and therapeutic targeting for discrimination between cancerous cells and normal cells that retain their correct protein folding machinery.

Folding fidelity is expected to be particularly impaired with the overexpression of certain proteins by selected tumor cells Which membrane proteins are over-expressed depends on the form of cancer. For example, some aggressive breast cancers over-express HER2 (Milanezi et al, Expert Rev Mol Diagn 8 (4), 417 (2008)), while some lung and colon cancers overexpress EGFR (Ciardiello and Tortora, N Engl J Med 358 (11), 1160 (2008)). CD20, a membrane-spanning protein of unclear function, is expressed on the surface of B-cell lymphomas, hairy cell leukemias, and B-cell chronic lymphocytic leukemias. CD38 is associated with leukemias and myelomas, while CD44 is a surface glycoprotein implicated in colon cancer metastasis. Targeting these various receptors provides a mechanism for identifying cancerous cells and directing cytotoxic treatments toward them.

Activating pro-apoptotic signalling pathways on cancerous cells is a related way of promoting eradication of the cancer. The Fas receptor (FasR) is involved in triggering apoptosis through an intracellular signalling cascade, so an agonist binding to FasR can trigger death of the cell (Daniel and Wilson, Curr Cancer Drug Targets 8 (2), 124 (2008)). One approach of exploiting this mechanism as a therapeutic strategy may be to selectively activate Fas receptors on cancerous cells, as nonspecific Fas activation generally leads to apoptosis of healthy cells expressing the Fas receptor. The Notch signalling pathway is involved in cell fate decisions, and dysregulated expression of the cell-surface Notch receptor, ligands and targets has been implicated in cervical, head and neck, endometrial, renal, lung, and breast carcinomas, pleural mesotheliomas, and malignant melanomas, as well as Hodgkin lymphomas, anaplastic large-cell non-Hodgkin lymphomas, and some acute myeloid luekemias and B-cell chronic lymphoid leukemias (Nickoloff et al, Oncogene 22, 6598 (2003). Blocking Notch signalling on cancerous cells by interference with the extracellular domain of Notch protein offers a way to attenuate the stimulus required for continued uncontrolled proliferation. Ideally, this interference should be limited to cancerous cells, as other non-malignant cells employ Notch signalling. Specifically targeting misfolded Notch receptor would accomplish this, as healthy cells will not present misfolded Notch to the extracellular environment. Additionally, the presence of misfolded Notch receptor protein on the cell surface can be used as an indicator of malignancy, enabling induction of an immune response against malignant cells expressing misfolded Notch by administration of an antibody against Notch specific for the misfolded conformation.

The overexpression and impaired folding fidelity expected in certain cancer cells is likely accompanied by partial unfolding of protein structured domains.

The protein unfolding process can be explained by studying free energy changes in proteins. The Gibbs free energy is the thermodynamic quantity minimized for spontaneous reactions occurring at constant pressure (Atkins and de Paula, Physical Chemistry, 7$^{th}$ Edition (2002)). Its change during a chemical process $\Delta G$ is a function of a reaction enthalpy change $\Delta H$, the reaction entropy change $\Delta S$, and the reaction temperature T:

$$\Delta G = \Delta H - T\Delta S$$

Alternatively, the Helmholtz free energy change $\Delta F = \Delta U - T\Delta S$, which replaces the enthalpy change with the internal energy change $\Delta U$, is nearly equivalent since protein unfolding involves a small change in the volume of the protein system and may also be calculated. For the process of protein unfolding, $\Delta H$ and $\Delta S$ are complicated functions that depend on many parameters of the protein's structure, including the hydrogen bonding network, topology of folding, interactions with solvent, and presence of post-translational modifications. The Gibbs free energy change is related to the equilibrium occupation of the folded and unfolded states by the equilibrium unfolding constant K:

$$K = \frac{[\text{Protein}]_{unfolded}}{[\text{Protein}]_{folded}} = \exp\left(-\frac{\Delta G}{RT}\right)$$

If the free energy of occupation for all partially unfolded states of a protein is known, the partition function Z may be constructed as a sum of Boltzmann factors over all partially unfolded states:

$$Z = \sum \exp\left(-\frac{\Delta G}{RT}\right)$$

The equilibrium probability of occupation for a given partially unfolded state i is then:

$$P_i = \frac{\exp\left(-\frac{\Delta G_i}{RT}\right)}{Z}$$

The difference in conformation between normally folded and misfolded protein introduces the concept of a disease-specific epitope—a region of the protein that is uniquely solvent exposed in the misfolded form. Antibodies raised against this epitope will therefore have the ability to bind exclusively to the misfolded protein, which is of use for diagnosis by identifying the presence of the misfolded protein in patient specimens. The application of antibodies against disease specific epitopes for treatment depends on the circumstances of the disease: in the case of cancer cells presenting misfolded protein, they can mark the cancerous cells for destruction by the immune system; for amyloidoses, they work by inhibiting the recruitment of additional misfolded monomers to the amyloid fibril, by marking the misfolded proteins for immune-mediated phagocytosis and destruction, and perhaps by also preventing template-directed misfolding by blocking binding of misfolded protein to normally folded protein.

In order to identify useful disease specific epitopes, a high resolution structure of the misfolded protein aggregate may provide a rational starting point for prediction. Unfortunately, technical limitations have rendered futile such atomic level structures for PrP$^{Sc}$, amyloids composed of Abeta, TTR, or Thy-1, or any misfolded protein on cancer cells, obviating predication of any stable discontinuous epitope or structured conformational epitope. A further limitation of this approach is that misfolded proteins may exist in an ensemble of interchangeable forms, with stable conformational epitope formation likely being non-universal. It is also in principle possible to identify misfolding specific linear epitopes experimentally by an exhaustive method comprising raising antibodies against all possible epitopes contained within the protein and screening them for selective reactivity toward the misfolded forms. However this "shotgun approach" for the thousands of overlapping linear epitopes in a medium-sized protein is likely to be expensive, laborious, and time-consuming. It is therefore desirable to rapidly and rationally limit candidate epitopes to ten or fewer per protein that can then be rigorously characterized for suitability as therapeutic or diagnostic targets.

From a diagnostic and therapeutic point of view it is important to identify disease-relevant epitopes caused by protein misfolding. Current strategies have focused on preparing misfolding-specific antibodies using whole misfolded protein as an immunogen. This approach has several disadvantages. Recombinant misfolded protein may not expose the disease-relevant epitopes due to differences between the in vitro and in vivo misfolding mechanisms. Furthermore, misfolding-specific epitopes are poorly recognized in the context of whole proteins (like PrPSc), and whole protein immunization runs the risk of immune recognition of native surface epitopes that could trigger autoimmunity.

SUMMARY OF THE INVENTION

In one of its aspects, the present invention provides a method of operating a system to identify an epitope unique to a misfolded form of a protein of interest, the system comprising an input unit, a candidate selection unit, a free energy computation unit, and an epitope identification unit, the method comprising:

(a) receiving by the input unit a model representing at least a portion of the structure of the protein of interest;
(b) selecting by the candidate selection unit one or more sets from the model, each set comprising one or more amino acid residues;
(c) determining by the free energy computation unit the free energy of unfolding of each set; and
(d) identifying by the epitope identification unit the epitope by:
  (i) determining the total probability of unfolding of each set based on the free energy of unfolding of one or more of the sets in isolation, and identifying the epitope from the sets having a total probability of unfolding above a minimum probability; or
  (ii) identifying the epitope from the sets having a free energy of unfolding below a minimum energy.

The method can be applied such that:

(a) the method further comprises receiving by the input unit a selection of a region in the model; and
(b) each of the one or more sets selected by the candidate selection unit comprise at least one residue in the region.

The model may be the structure of at least a portion of the protein of interest. The model may also be a predicted structure of at least a portion of the protein of interest. The predicted structure may be predicted from the primary sequence of the protein of the protein of interest, or portion thereof, or is predicted from the structure of one or more other proteins, or portions thereof, wherein the one or more other proteins are homologous to the protein of interest.

Selecting by the candidate selection unit one or more sets from the model comprises selecting all sets may comprise a sequence of one or more contiguous amino acid residues in the model. Selecting by the candidate selection unit one or more sets from the model may also comprise selecting all sets comprising a sequence of one or more contiguous residues in the model, wherein each set comprises at least one amino acid residue in the region. Selecting by the candidate selection unit one or more sets from the model may also comprise selecting all sets comprising two or more non-contiguous sequences of one or more contiguous amino acid residues in the model. Selecting by the candidate selection unit one or more sets from the model may also comprise selecting all sets comprising two or more non-contiguous sequences of one or more amino acid residues in the model, wherein each set comprises at least one amino acid residue in the region. Further, each sequence may comprise a length between a minimum length and a maximum length.

Determining by the free energy computation unit the free energy of unfolding of each set may comprise determining the enthalpy of unfolding of the set. Determining the enthalpy of unfolding of the set may also comprise:

(a) determining the total number of pairs of polar atoms in the model that (i) are comprised of at least one polar atom in the set, (ii) are more than one amino acid residue apart in the amino acid sequence of the model, and (iii) are within a cutoff distance from one another; and
(b) determining the enthalpy of unfolding of the set as the product of the total number of pairs determined in (a) by a fixed interaction energy.

Determining the enthalpy of unfolding of the set may also comprise:

(a) determining the total number of pairs of atoms in the model that (i) are comprised of polar or non-polar atoms, (ii) are comprised of at least one atom in the set, (ii) are more than one amino acid residue apart in the amino acid sequence of the model, and (iii) are within a cutoff distance from one another; and
(b) determining the enthalpy of unfolding of the set as the product of the total number of pairs determined in (a) by a fixed interaction energy.

The cutoff distance may be between about 2 Angstroms and about 7 Angstroms. The fixed interaction energy may be between about 0.5 and about 2 kcal/mol/interaction.

Determining the enthalpy of unfolding of the set may also comprise summing the results of solving the following equation for each pair of polar atoms in the model that are comprised of at least one atom in the set:

$$\Delta H = \in' \cos^4(\theta)\left(\left(\frac{1}{r}\right)^{10} - \beta\left(\frac{1}{r}\right)^{12}\right)$$

wherein:

ΔH is the enthalpy of unfolding of the pair of polar atoms;
$\acute{\varepsilon}$ is a fitting parameter;
θ is the angle between covalent bonds to carbon involving the polar atoms
r is the distance between the pair of polar atoms; and
β is a fitting parameter.

Determining the enthalpy of unfolding of the set may also comprise summing the results of solving the following equation for each pair of atoms in the model that (i) are comprised of at least one atom in the set and (ii) are comprised of polar or non-polar atoms:

$$\Delta H = \in' \cos^4(\theta)\left(\left(\frac{1}{r}\right)^{10} - \beta\left(\frac{1}{r}\right)^{12}\right)$$

wherein:

ΔH is the enthalpy of unfolding of the pair of polar atoms;
$\acute{\varepsilon}$ is a fitting parameter;
θ is the angle between covalent bonds to carbon involving the atoms
r is the distance between the pair of atoms; and
β is a fitting parameter.

Determining the enthalpy of unfolding of the set may also comprise:
(a) determining the solvent accessible surface area of the polar, nonpolar and hydroxyl functional groups that comprise the amino acid residues in the model;
(b) determining the solvent accessible surface area of the polar, nonpolar and hydroxyl functional groups that comprise the amino acid residues in the model with the set removed;
(c) determining the solvent accessible surface area of the polar, nonpolar and hydroxyl functional groups that comprise the amino acid residues of the set in isolation;
(d) determining the sum of the solvent accessible surface area of the polar functional groups determined in (b) and (c) minus the solvent accessible surface area of the polar functional groups determined in (a);
(e) determining the sum of the solvent accessible surface area of the nonpolar functional groups determined in (b) and (c) minus the solvent accessible surface area of the nonpolar functional groups determined in (a);
(f) determining the sum of the solvent accessible surface area of the hydroxyl functional groups determined in (b) and (c) minus the solvent accessible surface area of the hydroxyl functional groups determined in (a);
(g) determining the enthalpy of unfolding of the set by solving the following equation:

$$\Delta H(T) = (-8.44 \Delta ASA_{nonpolar} + 31.4(\Delta ASA_{polar} + \Delta ASA_{hydroxyl}) - (60-T)$$
$$(0.45 \Delta ASA_{nonpolar} - 0.26 \Delta ASA_{polar} - 0.09 \Delta ASA_{hydroxyl})) \frac{cal}{mol \cdot K}$$

wherein:
ΔH is the change in enthalpy of unfolding of the set;
T is the temperature;
$\Delta ASA_{polar}$ is the change in solvent accessible surface area of the nonpolar functional groups determined in (d);
$\Delta ASA_{nonpolar}$ is the change in solvent accessible surface area of the nonpolar functional groups determined in (e); and
$\Delta ASA_{hydroxyl}$ is the change in solvent accessible surface area of the hydroxyl functional groups determined in (f).

Determining the solvent accessible surface area of the polar, nonpolar and hydroxyl functional groups of the set in isolation may comprise:
(a) for each amino acid residue in the set not located at the N- or C-terminus of the protein of interest:
  (i) selecting a polypeptide formed of the amino acid residue and a first number of the closest neighbouring amino acid residues to the amino acid residue in the amino acid sequence of the protein of interest.
  (ii) obtaining a plurality of structures of the polypeptide by simulating the motion of the polypeptide in isolation in a molecular dynamics simulation;
  (iii) determining the solvent accessible surface area of the polar, nonpolar and hydroxyl functional groups of each structure; and
  (iv) averaging each of the solvent accessible surface area of the polar, nonpolar and hydroxyl functional groups over all of the structures.
(b) for each amino acid residue in the set located at the N- or C-terminus of the protein of interest:
  (i) selecting a polypeptide formed of the amino acid residue and second number of the closest neighbouring amino acid residues to the amino acid residue in the amino acid sequence of the protein of interest.
  (ii) obtaining a plurality of structures of the polypeptide by simulating the motion of the polypeptide in isolation in a molecular dynamics simulation;
  (iii) determining the solvent accessible surface area of the polar, nonpolar and hydroxyl functional groups of each structure; and
  (iv) averaging each of the determined solvent accessible surface area of the polar, nonpolar and hydroxyl functional groups over all of the structures.

The first number may be 2 and the second number may be 1.

Determining by the free energy computation unit the enthalpy of unfolding of the set may comprise:
(a) simulating the motion of the model in a molecular dynamics simulation;
(b) summing the interaction energies between all pairs of amino acid residues in the model, wherein each pair comprises at least one amino acid residue in the set;
(c) simulating the motion of the model with the set in an unfolded state in a molecular dynamics simulation;
(d) summing the interaction energies between all pairs of amino acid residues in the set in the unfolded state; and
(e) subtracting the interaction energies determined in (d) from (b).

Determining by the free energy computation unit the free energy of unfolding of each set may comprise determining the free energy of breaking one or more salt bridges in the model by unfolding the set.

Determining the free energy of breaking one or more salt bridges in the model by unfolding the set comprises determining the sum of the Coulombic energy between each pair of oppositely charged amino acid residues in the model within a cutoff distance from one another and wherein each pair comprises at least one amino acid residue in the set, the Coulombic energy determined assuming a fixed permittivity within the protein. The cuttoff distance may be about 7 Angstroms. The fixed permittivity may be between about 4 and about 20.

Determining the free energy of breaking one or more salt bridges in the model by unfolding the set may also comprise determining the sum of the Coulombic energy between each pair of amino acid residues in the model, wherein each pair comprises at least one amino acid residue in the set, the Coulombic energy determined assuming a fixed permittivity within the protein. The fixed permittivity may be between about 4 and about 20.

Determining the free energy of unfolding of each set may comprise determining the effects of one or more glycans on the free energy by solving the following equation:

$$\Delta G_{PTM} = -RT \ln\left(1 - \frac{a}{r_o}\left(1 - \operatorname{erf}\left(\frac{a - r_o}{b\sqrt{(2/3)n}}\right)\right)\right)$$

wherein:
$\Delta G_{ptm}$ is the effect of the glycans on the free energy of unfolding;
R is the ideal gas constant;
T is the temperature;
a is the radius of the glycans;
$r_o$ is the starting position of the set around the glycans as measured from the center of the glycans;
erf is the error function;
b is the persistence length of the unfolded set; and
n is the number of residues in the unfolded set.

Determining the total probability of unfolding of each set based on the free energy of unfolding of one or more of the sets may comprise, for each set, determining the sum of the equilibrium probabilities of unfolding of all of the sets comprising the amino acid residue sequence of the set, the equilibrium probability of unfolding of each set determined based on the free energy of unfolding of the set.

The minimum probability may be a multiple of the average probability of unfolding of all the sets having the same length. The multiple may be at least 10. The multiple may also be at least 100.

The minimum energy may be a fixed amount less than the average free energy of unfolding of all sets having the same length. The fixed amount may be at least 1.4 kcal/mol. The minimum energy may be 8 kcal/mol or less.

In another aspect, the present invention provides a method for obtaining an immunogen useful to produce an antibody that binds selectively to a misfolded form of a protein relative to the natively folded form of that protein, the method comprising:
(a) applying the method of operating a system to identify an epitope unique to a misfolded form of a protein of interest described above to identify an epitope presented uniquely by a misfolded form of said protein; and
(b) producing an immunogen comprising a peptide that comprises an epitope unique to the misfolded form of said protein.

In another aspect, the present invention provides an immunogen, whenever produced by the preceding method.

In another aspect, the present invention provides a method for obtaining an antibody that binds selectively to a misfolded form of a protein relative to the natively folded form of that protein, the method comprising:
(a) applying the method of operating a system to identify an epitope unique to a misfolded form of a protein of interest described above to identify an epitope unique to a misfolded form of said protein; and
(b) producing an antibody that binds selectively to said epitope, thereby obtaining an antibody that binds selectively to said misfolded form of said protein.

In another aspect, the present invention provides an antibody, whenever prepared by the preceding method.

In another aspect, the present invention provides a method for obtaining a pharmaceutical composition useful to treat a subject presenting with a disease associated with a misfolded form of a protein, the method comprising combining a pharmaceutically acceptable carrier with a medically useful amount of an antibody or binding fragment thereof that binds to an epitope that is unique to the misfolded form of the protein relative to the natively folded form thereof and that was identified using the method of operating a system to identify an epitope unique to a misfolded form of a protein of interest described above.

In another aspect, the present invention provides a method for treating a subject presenting with a disease associated with a misfolded form of a protein, the method comprising administering to the subject a pharmaceutical composition comprising an effective amount of an antibody or binding fragment thereof that binds selectively to an epitope unique to the misfolded form of the protein relative to the natively folded form of the protein, wherein the epitope was identified by applying the method of operating a system to identify an epitope unique to a misfolded form of a protein of interest described above.

In another aspect, the present invention provides a method for treating a subject presenting with a disease associated with a misfolded form of a protein, the method comprising administering to the subject a pharmaceutical composition comprising an effective amount of a vaccine comprising an immunogen that incorporates a peptide comprising an epitope unique to the misfolded form of the protein relative to the natively folded form of that protein, wherein the epitope was identified by applying the method of operating a system to identify an epitope unique to a misfolded form of a protein of interest described above.

In another aspect, the present invention provides a method for detecting a misfolded form of a protein in a sample, the method comprising:
(a) treating a sample suspected to contain a misfolded form of the protein with an antibody or binding fragment that binds selectively to an epitope presented uniquely by the misfolded protein relative to the natively folded form of that protein, wherein said epitope has been identified by applying the method of operating a system to identify an epitope unique to a misfolded form of a protein of interest described above; and
(b) determining whether an antigen:antibody complex has formed, the formation thereof being indicative of the presence in the sample of a misfolded form of said protein.

In another aspect, the present invention provides a method of diagnosing disease associated with a misfolded form of a protein, the method comprising:
(a) treating a sample that is obtained from a subject and is suspected to contain the misfolded form of the protein with an antibody or binding fragment that binds selectively to an epitope presented uniquely by the misfolded protein relative to the natively folded form of that protein, wherein said epitope has been identified by applying the method of operating a system to identify an epitope unique to a misfolded form of a protein of interest described above; and
(b) determining whether an antigen:antibody complex has formed, the formation thereof being indicative of the presence in the sample of a misfolded form of said protein.

In another aspect, the present invention provides a method for obtaining an antibody that binds selectively to a misfolded form of a protein relative to the natively folded form of that protein, the method comprising:
(a) obtaining an immunogen comprising any three contiguous amino acids resident in a peptide having one of SEQ ID Nos. 1-80, with the proviso that the peptide does not have the sequence of SEQ ID No.5, 7, 27-40 or 76; and
(b) using the immunogen to produce an antibody that binds selectively to said epitope, thereby obtaining an antibody that binds selectively to said misfolded form of said protein.

In another aspect, the present invention provides an antibody that binds to an epitope that includes at least 3 contiguous amino acids resident in a peptide having SEQ ID Nos 1-4, 6, 8-26, 28, 29, 31-36, 41-75 and 77-80.

In another aspect, the present invention provides a pharmaceutical composition comprising a therapeutically effective amount of an antibody according to the preceding antibody and a pharmaceutically acceptable carrier.

In another aspect, the present invention provides a method for treating a subject presenting with or at risk for a disease associated with a misfolded form of a protein, the method comprising the step of administering to a subject in need thereof an effective amount of pharmaceutical composition comprising an antibody or binding fragment thereof that binds selectively to an epitope unique to the misfolded form of the protein relative to the natively folded form of that protein, wherein the misfolded protein to which the antibody binds is selected from tau, Abeta, SOD1, α-synuclein, PrP$^C$, TTR, δ2-microglobulin, EGFR, CD20, CD38, CD44, FasR, and Notch1. The epitope to which the antibody binds may comprise at least 3 contiguous amino acids resident in a peptide having any one of SEQ ID Nos. 1-4, 6, 8-26, 28, 29, 31-36, 41-75 and 77-80. The antibody and disease to be treated may be selected from:

(a) an antibody that binds selectively to the epitope designated by SEQ ID No. 1, 2, 3, 4, 5, 6, 7, 8, 9 or 10, and particularly 3, 4, 6, 7, 8, 9 or 10, for the treatment of subjects afflicted with CJD or a related prion disease;

(b) an antibody that binds selectively to the epitope designated by SEQ ID No. 16, 17, 18, 19, 20, 21 or 22 for the treatment of subjects afflicted with familial amyloid polyneuropathy or senile systemic amyloidosis or a disease related by the presence of misfolded TTR;

(c) an antibody that binds selectively to the epitope designated by SEQ ID No. 23, 24, 25, or 26 for the treatment of subjects afflicted with renal accumulation of β2 microglobulin amyloid deposits or a disease related by the presence of misfolded β2 microglobulin;

(d) an antibody that binds selectively to the epitope designated by SEQ ID No. 27, 28, 29, 30, 31, 32, 33, 34, 35, 36, 37, 38, 39 or 40, and particularly by SEQ ID Nos. 28, 29, 31, 32, 33, 34, 35 and 36 for the treatment of subjects afflicted with amyotrophic lateral sclerosis (ALS) or a disease related by the presence of misfolded SOD1;

(e) an antibody that binds selectively to the epitope designated by SEQ ID No. 41, 42, 43, 44, or 45 for the treatment of subjects afflicted with leukemias or myelomas or a disease related by the presence of misfolded CD38;

(f) an antibody that binds selectively to the epitope designated by SEQ ID No. 46, 47, f8, 49, or 50 for the treatment of subjects afflicted with colon cancer metastasis and or a disease related by the presence of misfolded CD44;

(g) an antibody that binds selectively to the epitope designated by SEQ ID No. 51, 52, 53, 54, or 55 for the treatment of subjects afflicted with cancer in which Fas receptor is implicated;

(h) an antibody that binds selectively to the epitope designated by SEQ ID No. 56, 57, 58, 59, or 60 for the treatment of subjects afflicted with cancers including cervical, head and neck, endometrial, lung and breast carcinomas, pleural mesotheliomas, malignant melanomas, Hodgkin lymphomas, anaplastic large cell non-Hodgkin lymphomas, or a disease related by the presence of misfolded NOTCH1 including certain acute myeloid leukemias and B-cell chronic lymphoid leukemias;

(i) an antibody that binds selectively to the epitope designated by SEQ ID No. 61, 62, 63, 64, or 65 for the treatment of subjects afflicted with cancer in which Fas receptor activation is implicated; and (j) an antibody that binds selectively to the epitope designated by SEQ ID No. 66, 67, 68, 69, 70, 71, 72, 73, 74, 75, 76, 77, 78, 79 or 80, with the optional proviso that SEQ ID No. 76 is excluded, for the treatment of subjects afflicted with certain cancers and related disorders in which misfolded EGFR is implicated.

In another aspect, the present invention provides a method for treating a subject presenting with, or at risk for, a disease associated with a misfolded form of a protein, the method comprising the step of administering to the subject a vaccine comprising an immunogen that incorporates a peptide constituting an epitope unique to the misfolded form of the protein relative to the natively folded form of that protein, wherein the epitope comprises at least 3 contiguous amino acids resident in a peptide having any one of SEQ ID Nos. 1-4, 6, 8-26, 28, 29, 31-36, 41-75 and 77-80. The vaccine and the disease to be treated may be selected from:

(a) a vaccine that incorporates an immunogen comprising the epitope designated by SEQ ID No. 1, 2, 3, 4, 5, 6, 7, 8, 9 or 10, and particularly 3, 4, 6, 7, 8, 9 or 10, for the treatment of subjects afflicted with CJD or a related prion disease;

(b) a vaccine that incorporates an immunogen comprising the epitope designated by SEQ ID No. 11, 12, 13, 14, or 15 for the prophylaxis in subjects, particularly cattle, at risk for BSE or a related prion disease;

(c) a vaccine that incorporates an immunogen comprising the epitope designated by SEQ ID No. 16, 17, 18, 19, 20, 21 or 22 for the treatment of subjects afflicted with familial amyloid polyneuropathy or senile systemic amyloidosis or a disease related by the presence of misfolded TTR;

(d) a vaccine that incorporates an immunogen comprising the epitope designated by SEQ ID No. 23, 24, 25, or 26 for the treatment of subjects afflicted with renal accumulation of β2 microglobulin amyloid deposits or a disease related by the presence of misfolded β2 microglobulin;

(e) a vaccine that incorporates an immunogen comprising the epitope designated by SEQ ID No. 27, 28, 29, 30, 31, 32, 33, 34, 35, 36, 37, 38, 39 or 40, and particularly by SEQ ID Nos. 28, 29, 31, 32, 33, 34, 35 and 36 for the treatment of subjects afflicted with amyotrophic lateral sclerosis (ALS) or a disease related by the presence of misfolded SOD1;

(f) a vaccine that incorporates an immunogen comprising the epitope designated by SEQ ID No. 41, 42, 43, 44, or 45 for the treatment of subjects afflicted with leukemias or myelomas or a disease related by the presence of misfolded CD38;

(g) a vaccine that incorporates an immunogen comprising the epitope designated by SEQ ID No. 46, 47, 48, 49, or 50 for the treatment of subjects afflicted with colon cancer metastasis and or a disease related by the presence of misfolded CD44;

(h) a vaccine that incorporates an immunogen comprising the epitope designated by SEQ ID No. 51, 52, 53, 54, or 55 for the treatment of subjects afflicted with cancer in which Fas receptor activation is implicated;

(i) a vaccine that incorporates an immunogen comprising the epitope designated by SEQ ID No. 56, 57, 58, 59, or 60 for the treatment of subjects afflicted with cancers including cervical, head and neck, endometrial, lung and breast carcinomas, pleural mesotheliomas, malignant melanomas, Hodgkin lymphomas, anaplastic large cell non-Hodgkin lymphomas, or a disease related by the presence of misfolded NOTCH1 including certain acute myeloid leukemias and B-cell chronic lymphoid leukemias;

(j) a vaccine that incorporates an immunogen comprising the epitope designated by SEQ ID No. 61, 62, 63, 64, or 65 for the treatment of subjects afflicted with cancer in which Fas receptor activation is implicated; and (k) a vaccine that incorporates an immunogen comprising the epitope designated by SEQ ID No. 66, 67, 68, 69, 70, 71, 72, 73, 74, 75, 76, 77, 78, 79 or 80, with the optional proviso that SEQ ID No. 76 is excluded, for the treatment of subjects afflicted with certain cancers and related disorders in which misfolded EGFR is implicated.

In another aspect, the present invention provides a peptide having an amino acid sequence set out in any one of SEQ ID Nos.1-80, in isolated form. The peptide may comprise an amino acid substitution. The peptide may also be a variant that is truncated by amino acid deletion to a length not exceeding 7 residues. The peptide may also be a variant that is extended by amino acid addition to a length of at least 7 residues.

In another aspect, the present invention provides the use of a method according to the method of operating a system to identify an epitope unique to a misfolded form of a protein of interest described above for identification of an epitope unique to a misfolded form of a protein, relative to the natively folded form of that protein.

In another aspect, the present invention provides the use of an epitope identified by the method of operating a system to identify an epitope unique to a misfolded form of a protein of interest described above for the production of an antibody that binds selectively to said epitope.

In another aspect, the present invention provides the use of an antibody that binds an epitope identified by the method of operating a system to identify an epitope unique to a misfolded form of a protein of interest described above for the detection of a misfolded form of a protein that presents said epitope.

In another aspect, the present invention provides the use of an antibody that binds an epitope identified by the method of operating a system to identify an epitope unique to a misfolded form of a protein of interest described above, for the treatment of a disease or disorder associated with a misfolded form of a protein that presents said epitope.

In another aspect, the present invention provides the use of an epitope identified by the method of operating a system to identify an epitope unique to a misfolded form of a protein of interest described above for the production of a vaccine for the treatment of a disease or disorder associated with a misfolded form of a protein that presents said epitope.

In other aspects, the invention provides for the use of epitopes identified by the epitope prediction methods, and related antibodies, to diagnose and treat disease and to screen samples for the presence of such epitopes.

Particularly, in a further aspect, the present invention provides a method for obtaining an immunogen useful to produce an antibody that binds selectively to a misfolded form of a protein relative to the natively folded form of that protein, the method comprising:

i) applying the epitope prediction method to identify an epitope presented uniquely by a misfolded form of said protein; and ii) producing an immunogen comprising a peptide that comprises an epitope unique to the misfolded form of said protein.

In related aspects, the invention provides an immunogen useful to raise antibodies, either endogenously in a subject to be treated or in a production host, wherein the immunogen comprises an epitope unique to the misfolded form of a protein.

In other related aspects, the invention provides an antibody useful to detect a misfolded protein in a sample or to treat a subject having a misfolded protein disease, wherein the antibody binds selectively to an epitope unique to the misfolded form of a protein relative to the natively folded form of that protein. In embodiments, the antibody is provided as a pharmaceutical composition comprising an amount of antibody effective for treatment. In another embodiment the antibody or a binding fragment is provided with a conjugated label, for detection of misfolded protein in a sample.

In another of its aspects, the present invention provides peptides of a specific sequence and antibodies that bind selectively therewith, which are useful to detect misfolded protein or to treat subjects presenting with diseases associated with those proteins.

In embodiments, the peptides are provided in isolated form, and have an amino acid sequence set out in any of SEQ ID Nos. 1-80.

In embodiments, the epitopes, peptides and antibodies of the invention are derived from or bind to proteins that in their misfolded state are associated with disease, wherein the proteins include tau, Abeta, SOD1, α-synuclein, PrP$^C$, TTR, β2-microglobulin, EGFR, CD20, CD38, CD44, FasR, and Notch1.

In embodiments, the immunogen and corresponding antibody are selected to target human proteins and particularly human proteins associated with disease, for use as either diagnostic or therapeutic agents useful in the detection or treatment thereof.

The invention provides, in part, methods for identifying regions or epitopes of structured protein domains which are prone to partially or fully unfold, making them susceptible to intermolecular interaction and aggregation. In alternative embodiments, the invention provides a method for identifying structured protein domains which are prone to partially unfold in cancer cells In one aspect of the invention, the method identifies the probability for unfolding of any region in a protein, accepting as input the atomic-resolution structure of that protein, or that of a related protein with high sequence similarity believed to have a similar structure to the protein of interest in the event that an atomic-resolution structure of the protein of interest is unavailable.

In another aspect of the invention, the method predicts disease-specific epitopes in proteins that could be used to diagnose and treat diseases associated with protein misfolding and cancer. In yet another aspect the invention a method is described for identifying the immunogenicity of regions found to have a relatively high probability of unfolding, to be used as epitopes for the development of antibodies, and isolating those epitopes that are expected to be immunoreactive only in the unfolded or misfolded state.

In alternative aspects, the methods according to the invention may be performed using a computer, for example, a computer including an input device, a processor, and an output device. In alternative embodiments, the invention includes a computer program, residing on a computer readable medium, for identifying regions or epitopes of structured protein domains which are prone to partially or fully unfold or for predicting a disease-specific epitope in a protein, together with instructions for a computer. In alternative embodiments, the invention provides a computational system including one or more of a general purpose programmable computer including software to implement the computational platform, dedicated hardware, and firmware, In alternative aspects, misfolding-specific epitopes identified according to the methods described herein, as well as antibodies immunoreactive to the misfolding-specific epitopes are encompassed within the scope of the invention. Such epitopes may by useful as diagnostic and therapeutic tools for the management of protein misfolding, cell proliferation, and other diseases.

This summary of the invention does not necessarily describe all features of the invention. Other aspects and features of the present invention will become apparent to those ordinarily skilled in the art upon review of the following description of specific embodiments of the invention.

DETAILED DESCRIPTION OF THE INVENTION

Figure 1:
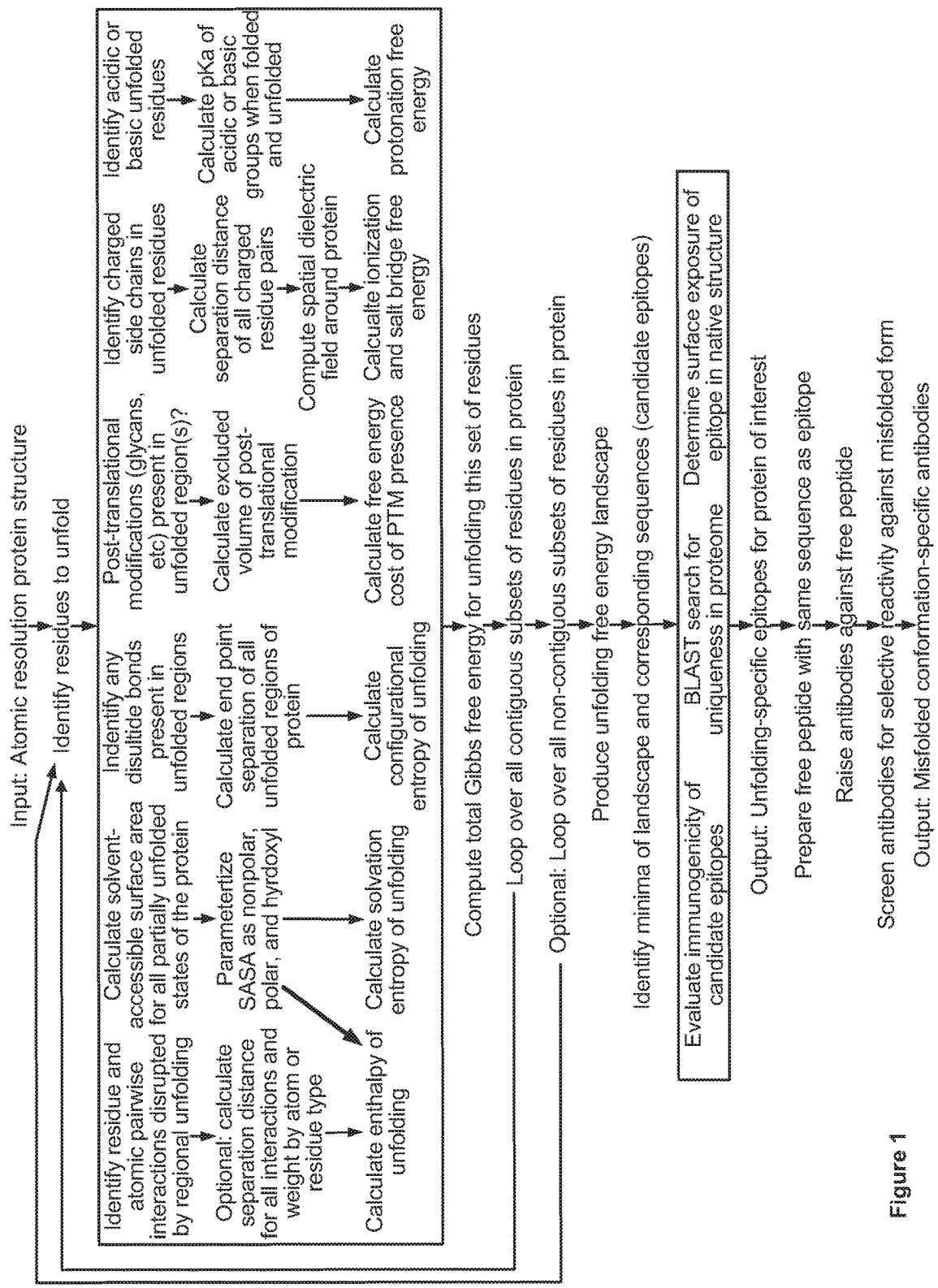
FIG. 1 is a flowchart of a method of identifying epitopes in regions of a protein that are prone to unfolding and producing antibodies against such epitopes according one embodiment of the invention.

In order that the invention herein described may be more fully understood, the following description is set forth and terminology is defined. Any terms not directly defined herein shall be understood to have the meanings commonly associated with them as understood within the art of the invention.

Free Energy of Unfolding Function

A component of the present invention is the calculation of the free energy change for unfolding of a set of one or more amino acid residues of a protein.

As explained in the background, the free energy change is a complex function of structural and solvation parameters of a protein. The epitope prediction methods according to the present invention address contributions to the free energy of unfolding, which include:

$\Delta H$, the enthalpy of unfolding, arising in part from the disruption of hydrogen bonds and their reformation with the solvent, and the disruption upon unfolding of the van der Waals interaction between hydrophobic groups in contact in the native protein conformation;

$\Delta S_{solvation}$, the solvation entropy of unfolding, arising from the formation of a structured solvation shell around newly solvent-exposed amino acids or residues of a protein;

$\Delta S_{configuration}$, the configurational entropy of unfolding, arising from the increased conformational freedom of the unfolded regions of the protein upon unfolding;

$\Delta G_{salt\ bridge}$, the free energy of breaking salt bridges that were present in the native structure;

$\Delta G_{charge\ transfer}$, the free energy of transferring charged groups in the protein between the low dielectric environment of the folded protein and the high dielectric environment of free solvent water;

$\Delta G_{pH}$, the free energy of changing pKa's of the acidic or basic side chains and N- and C-termini of the protein as a consequence of unfolding; and $\Delta G_{PTM}$, the effect of post-translational modifications, including glycans, on the stability of the folded and unfolded states.

The epitope prediction methods can accept as input the atomic resolution structure of a protein (as for example determined by nuclear magnetic resonance, X-ray crystallography, electron microscopy or other methods known in the art), as well as, other structures as further described herein. The epitope prediction methods can obtain an accurate determination of the free energy of unfolding a set of amino acid residues from the protein by analyzing the values of these contributions, for example, as follows:

$$\Delta G_{unfolding} = \Delta H - T\Delta S_{solv} - T\Delta S_{config} + \Delta G_{saltbridge} + \Delta G_{chargetrans} + \Delta G_{pH} + \Delta G_{PTM}$$

It is to be understood that the contributions to the free energy of unfolding described above are exemplary and are not intended to be exhaustive or necessary in the calculation of the free energy of unfolding. Accordingly, one or more of the contributions described above may be removed from the calculation of the free energy of unfolding and/or one or more other contributions known in the art may be added to the calculation of the free energy of unfolding while still falling within the scope of the present invention.

Enthalpy of Unfolding

The enthalpy of unfolding describes the change in internal energy and the product of system pressure and volume arising from unfolding of part of the protein structure, including changes in hydrogen bonding (both within the protein and with solvent), van der Waals, and cation-pi energies. The enthalpy of unfolding may be calculated in several ways, without limitation.

The enthalpy of unfolding of a set may be determined by identifying the discrete interactions between hydrogen bonded pairs disrupted by unfolding.

Each interaction may be assigned a potential energy as the energy required to break that bond. In a non-distance dependent approach, any polar atoms (e.g., N, O, or S) found to be within a cutoff distance $r_{crit}$ of each other, and having at least one atom within the set, are assigned a fixed interaction energy $\varepsilon$, which may be between about 1 and about 2 kcal/mol/interaction (Nicholls et al Proteins 11 (4) 281-296 (1991)). Alternatively, the fixed interaction energy may be between about 0.5 and about 2 kcal/mol/interaction. The total enthalpy of unfolding a set may then be determined by considering each polar atom in the amino acid sequence of the set to be unfolded and identifying all the polar atoms belonging to residues greater than one away from it in the amino acid sequence of the protein that are within the $r_{crit}$. Redundant interactions may be eliminated (those between residues in the set to be unfolded will otherwise be counted twice), and the number of interactions may be multiplied by $\varepsilon$ to determine the total enthalpy of unfolding. In the alternative, the non-distance approach described above may be applied to pairs of atoms comprised of polar and non-polar atoms.

The cutoff distance may be about 4.8 Angstroms. Alternatively, the cutoff distance may be between about 2 Angstroms and about 7 Angstroms, or any value(s) therebetween, such as between about 3 and about 5 Angstroms. The fixed interaction energy $\varepsilon$ may be chosen to reproduce the experimentally-determined stability of the protein when the protein is completely unfolded by the method as described above. The total enthalpy of unfolding of a set may be determined by considering each polar and/or non-polar atom in the sequence to be unfolded and identifying all of the polar and/or non-polar atoms belonging to residues greater than 3 away from it in the amino acid sequence of the protein that are within the $r_{crit}$.

The energy of interaction may be distance dependent, such that the energy of interaction between two polar atoms varies as their separation distance r changes. This distance dependence may take the form of a "10-12" potential used to model hydrogen bonding interactions (Gordon D B et al Curr Op Struct Biol 9 509 (1999)), such the energy of separating two polar atoms may be represented by $$\Delta H = \epsilon' \cos^4(\theta)\left(\left(\frac{1}{r}\right)^{10} - \beta\left(\frac{1}{r}\right)^{12}\right)$$

In this equation, θ is the angle between the covalent bonds of the polar atoms to adjacent carbon atoms, and r is the separation distance between the polar atoms. The angle θ may be limited to an angle cutoff in determining whether or not a hydrogen bond exists. The smaller the angle cutoff, the less hydrogen bonds will be counted. In one embodiment, the angle cutoff may be around 20 degrees. Alternatively, the angle cutoff may be between about 15 and about 35 degrees. The constants ε' and β may be selected such that the average interaction energy per hydrogen bond lies between about 1 and about 2 kcal/mol. In one embodiment, β is taken to have a value of between about 5 and about 6. In an alternative embodiment, the constants ε' and β may be selected such that the average interaction energy per hydrogen bond lies between about 0.5 and about 2 kcal/mol. In the further alternative, the distance approach described above may be applied to pairs of atoms comprised of polar and non-polar atoms.

In another embodiment, the change in solvent accessible surface area (ASA) may be used to describe the enthalpy change on unfolding. The change in enthalpy to expose surface area upon unfolding has been determined experimentally (Murphy and Friere, Adv Protein Chem 43, 313 (1992)). This enthalpy change depends on the polar, nonpolar, or hydroxyl character of residue groups. It is given at Celsius temperature T in terms of the change in ASA as:

$$\Delta H(T) = (-8.44 \Delta ASA_{nonpolar} + 31.4(\Delta ASA_{polar} + \Delta ASA_{hydroxyl}) - (60-T)$$
$$(0.45 \Delta ASA_{nonpolar} - 0.26 \Delta ASA_{polar} - 0.09 \Delta ASA_{hydroxyl})) \frac{cal}{mol \cdot K}$$

Nitrogen, oxygen, and sulfur atoms in the structure may be considered to be polar, except those oxygens in the hydroxyl groups of threonine, serine, and tyrosine residues, which may be considered to be hydroxyl. Carbon atoms may be considered to be nonpolar, and hydrogens may be classified according to the atom to which they are bonded: hydrogens on a carbon may be considered nonpolar, hydrogens on a polar atom may be considered to be polar, and the hydrogen on a hydroxyl oxygen may be considered to be hydroxyl. The ASA of each atom in a structure may be calculated by a water-probe sweeping method (Lee and Richards, J Mol Biol 55 (3), 379 (1971)), using a probe radius of 1.4 angstroms, or by any other suitable method known in the art. The change in ASA on unfolding of a set of amino acid residues of the protein of interest may be calculated by taking the difference in ASA between the protein with the set unfolded and the natively structured protein by, for example:

1. Deleting the set considered to be unfolded from the structure of the protein and calculating the ASA of polar, nonpolar, and hydroxyl functional groups in the partial structure.
2. Taking the residues in the unfolded set and isolating triplets of the protein sequence as tripeptides, with each residue in the unfolded set located in the middle position of one tripeptide. Each tripeptide may then be used in an all-atom molecular dynamics simulation to determine the motion of the free tripeptide. Several structures of the tripeptide may be collected during the simulation, and the ASA of polar, nonpolar, and hydroxyl groups may be calculated for each structure and averaged among the structures. The average free-tripeptide ASA values for each residue in the unfolded set may be summed to obtain the total ASA of the free part of the protein.
3. Calculating the ASA of polar, nonpolar, and hydroxyl functional groups in the intact native protein structure.
4. Taking the ASA calculated in step (3) and subtracting it from the sum of the solvent accessible surface area (SASA) values found in (1) and (2).

Substituting the SASA values resulting from taking this difference into the experimental enthalpy change equation above yields the enthalpy change on unfolding.

In the alternative, the second step of the method described above may be modified to utilize polypeptides of length greater or less than 3.

In a further alternative, the method may be applied in a different manner to amino acid residues in the set located at the N- or C-terminus of the protein of interest. For example, for each amino acid residue in the set not located at the N- or C-terminus of the protein of interest, a polypeptide may be selected comprising the amino acid residue and a first number of the closest neighbouring amino acid residues to the amino acid residue in the amino acid sequence of the protein of interest. For each amino acid residue in the set located at the N- or C-terminus of the protein of interest, a polypeptide may be selected comprising the amino acid residue and a second number of the closest neighbouring amino acid residues to the amino acid residue in the amino acid sequence of the protein of interest. In one embodiment, the polypeptide may be a tripeptide, the first number may be 2 and the second number may be 1. In alternative embodiments, the first number and second number may be similar or dissimilar and may range from values of zero to the length of the protein of interest minus one.

In yet another embodiment, enthalpy change may be calculated from all-atom or coarse-grained molecular dynamics simulations of the protein in the folded and the unfolded state. For example, the enthalpy change may be calculated by:

1. Simulating the motion of the folded protein in a system containing the protein surrounded by a solvent composed of water molecules at a pressure and density representative of human physiologic conditions by solving Newton's equations of motion iteratively in time to determine the evolution of the system. The time between iterations may be about 1-2 femtoseconds and the temperature of the system may equal the physiologic temperature of the organism from which the protein is derived, most commonly 37 degrees Celsius. In alternative embodiments, the time step may range from about 0.1 femtoseconds to about 10 femtoseconds and the system temperature may be any temperature less than the unfolding temperature of the protein. The simulation may continue until the protein has sampled its equilibrium motion, most commonly about 20—about 40 nanoseconds. Pairwise energies between residues in the native state may be extracted from the simulation using currently-available potential energy functions (Brooks, J Comp Chem 30, 1545 (2009)) and may be averaged over the simulation.

2. Simulating the motion of the unfolded protein in a system containing the protein surrounded by a solvent composed of water molecules by first unfolding the protein from its native conformation with the use of supraphysiologic temperatures or direct application of outward forces to two or more structural elements of the protein. Periodic temperature quenching of the system to return it to physiologic temperature is performed to enable extraction of potential energies from the simulation. After extraction of potential energy information, the system may be returned to supraphysiologic temperature to enable more rapid evolution toward a different unfolded conformation. The simulation must sample a representative set of the unfolded conformations of the protein of interest, as established when the addition of more conformations to the set do not change the average pairwise energies by an amount greater than the desired precision, most commonly 1 kcal/mol. In one embodiment, 1000 alternations between supraphysiologic and physiologic temperature may be employed. Alternatively, as few as 10 alternations may be employed. Accordingly, the alternations may range from about 10 to about 1000. In the further alternative, the alternations may be any value capable of being simulated by a computing system.

3. Calculating from Steps (1) and (2) the unfolding free energy for a given set of amino acid residues of the protein. This includes summing the interaction energies from Step (2) between all pairs of residues in the unfolded set and subtracting from this sum the interaction energies from Step (1) between all pairs of residues in the unfolded set and the whole protein.

Alternatively, Steps (1) and (2) may be replaced by equivalent coarse-grained simulations, in which the detailed atomic structure of the protein and solvent may be supplanted by a parameterized description of the system in which each protein residue and solvent molecule is treated as a unitary entity with no internal degrees of freedom. In a further alternative, each protein residue may be divided into entities representing its peptide backbone and side chain separately. In yet a further alternative, other divisions of the system into any number of objects less than the total number of atoms in the protein-solvent system may be applied. In a yet further alternative, the solvent surrounding the protein may be replaced by an implicit force-field that approximates the effects of solvent molecules on the motion of the protein.

Solvation Entropy

The solvation entropy describes the change in the number of solvent microstates accessible due to changes in the exposure of functional groups in the protein, which may involve the formation of solvent cages around the newly exposed groups that reduces the freedom of solvent motion. The solvation entropy of polar groups, including hydroxyl groups, is generally 0 at a temperature of 335K and the solvation entropy of nonpolar groups is generally 0 at 385K (Baldwin, Proc Natl Acad Sci 83, 8069 (1986)). Using this result and the changes in SASA calculated as, for example, described under the heading "Enthalpy of Unfolding," the solvation entropy may be calculated at any temperature T.

In an alternative embodiment of the invention, the total solvation entropy may be calculated by solving the Poisson-Boltzmann equation to determine the total polar solvation energy (Baker N A, et al *Proc. Natl. Acad. Sci. USA* 98, 10037 (2001)).

Configurational Entropy

The configurational entropy describes the change in the number of protein microstates on unfolding due to reduced steric constraints on the unfolded segment. When a protein has folded into its native state, the mobility of the protein backbone and side chains is constrained. The native state of a protein therefore has a low configurational entropy compared to that present in its partially unfolded state, in which the unfolded set of amino acid residues is free to explore a much greater number of arrangements, subject to the limitations of having the starting and ending positions of the unfolded set fixed by continuity with the still-folded part of the protein, as well as the restrictions due to the steric excluded volume of the folded part of the protein and the unfolded strand itself.

The contribution of each amino acid to the configurational entropy change on complete protein unfolding is known (see, for example, D'Aquino et al, Proteins 25, 143 (1996)) and may be incorporated into the epitope prediction methods according to the invention by, for example, summing the values for each amino acid participating in the unfolded set. The component of the configurational entropy change associated with side chain exposure to solvent on unfolding may be prorated based on the degree of side chain solvent exposure present in the native structure, such that a residue in the native structure with a completely buried side chain receives 100% of this contribution and a residue with a completely exposed side chain receives none.

The presence of the still-folded part of the protein reduces the total configurational freedom of the unfolded set in the case of partial unfolding. This effect may be treated using a diffusion equation model for the unfolded polymer strand, where the rest of the protein may be treated as a planar absorbing boundary. This may account for the reduction in states due to the steric constraints of the rest of the still-folded protein. The approximation of a planar boundary may be desirable because the radius of the protein is generally larger than the radius of gyration of a typical melted strand of polymer, for initial unfolding events. The probability distribution $p_w$ of a random walker to propagate a distance r into a volume of space $\Delta\tau$, in the presence of an absorbing boundary, may be given by:

$$p_w(r|n)\Delta\tau = \frac{\Delta\tau}{b}\frac{3z}{nb}\left(\frac{3}{2\pi n}\right)^{3/2} e^{-3r^2/2nb^2}$$

where b is the distance between alpha carbons in a protein (3.4 angstroms), z is the distance of the end point of the residues' random walk from the absorbing boundary, and n is the number of residues in the random walk.

Salt Bridge Energy

The salt bridge energy describes a component of the unfolding enthalpy that is calculated separately. It arises from the disruption of Coulombic interaction between full and partial charges in the native structure and the change in polarization of the dielectric surrounding each charge as the dielectric environment shifts from that in the protein to that in water. Disruption of salt bridges involving residues in the set of amino acid residues to be unfolded imposes an energetic cost. This effect may be addressed by considering in turn all charged residues present in the protein. For each charged residue, the oppositely charged residues present in the protein at a distance of less than about 7 angstroms may be identified, and each nonredundant pair of oppositely charged residues identifies and existing a salt bridge. In the alternative, a distance cutoff of between about 3 and about 10 Angstroms for salt bridges may be used. The Coulombic energy E of a salt bridge between two charges $q_1$ and $q_2$ separated by a distance r is calculated using a Coulombic relationship according to $E=1/(4\pi\kappa\varepsilon_0)*q_1 q_2/r^2$, where $\varepsilon_0$ is the permittivity of free space, assuming a fixed permittivity $\kappa$ of between about 10 and about 20, characteristic of the interior of a protein. Alternatively, $\kappa$ may be between about 2 and about 20. The energies of those salt bridges disrupted by partial unfolding are summed to produce the total salt bridge energy change involved in unfolding the set.

In the alternative, interactions between all pairs of charged particles, whether oppositely or similarly charged, may be identified and assigned an energy based on a Coulombic potential. Interactions involving members of the unfolded set are deemed to have been abolished on unfolding, so that the salt bridge energy change is the sum of these interaction energies. In the further alternative, interactions between all pairs of charged particles may be calculated by solution of the Poisson-Boltzmann equation using a locally-varying dielectric function that describes the electrostatic environment in and around the protein.

Charge Transfer Energy

Unfolding parts of a protein containing charged residues transfers their charged groups between dielectric environments, with an energy change. The energy change $\Delta G_{chargetransfer}$ depends on the dielectric environment around the charged groups in the folded and unfolded states $\varepsilon_{folded}$ and $\varepsilon_{unfolded}$ respectively and the separation distance r of the charged group from the surrounding dielectric environment according to $$\Delta G_{chargetransfer} = \frac{1}{8\pi \varepsilon_o\, r}\left(\frac{1}{\varepsilon_{unfolded}} - \frac{1}{\varepsilon_{folded}}\right)$$

In the present invention, $\varepsilon_{folded}$ is determined by an average of the dielectric constant of 10 to 20 for the interior of a protein and the dielectric constant of 78 for water weighted by the solvent exposure of the charged groups. The unfolded permittivity $\varepsilon_{unfolded}$ is taken to be 78, the relative permittivity for bulk water, and r is taken to be the ion radius plus the radius of a water molecule, or 2.8 to 3 angstroms. Alternatively, $\varepsilon_{folded}$ may be taken to be between about 2 and about 10. The transfer energy for each charged group in the unfolded set may be summed to obtain the total transfer energy of unfolding.

In an alternate embodiment, the dielectric constant in the folded state for each charged group may be calculated using the polarizability of the surrounding residues and the Debye equation (Onsager L J. Am. Chem Soc 58 1486-1493 (1936) or the Kirkwood-Frohlich equation.

pH Effects

The protonation energy describes the energy change due to the change in occupation probability for hydrogens on acidic and basic groups in the protein. As the electrostatic environment around acidic and basic groups changes during unfolding, their energies of protonation change. The pKa of the acidic and basic groups when folded may be calculated from the native protein structure (see, for example, Hui Li, et al. *Proteins*, (2005), 61, 704-721., Hilser et al, U.S. Pat. No. 7,027,969). Using this information, the change on unfolding of the free energy of protonation can be calculated for residues in the unfolded set, taking the pKa of acidic or basic residues in the unfolded state to be the same as for free amino acids.

Post Translational Modifications, Including Glycans

Post-translational modification energy describes a combined energy/entropy term due to the presence of disulfide bonds, glycans, GPI anchors, and related phenomena. The main effect of glycans on protein stability is to raise the free energy of the unfolded state by reducing the conformational entropy. The reduction in backbone entropy may be addressed by utilizing an analytic expression for the fraction of random walks consistent with the steric constraints of a spherical object whose volume is equal to that of the glycan. The expression for the entropy loss $\Delta G_{PTM}$ is $$\Delta G_{PTM} = -RT\ln\left(1 - \frac{a}{r_o}\left(1 - \operatorname{erf}\left(\frac{a - r_o}{b\sqrt{(2/3)n}}\right)\right)\right)$$

In this expression, R is the ideal gas constant, T is the temperature of interest (generally 37 degrees Celsius), a is the radius of the effective glycan sphere, $r_o$ is the distance from the center of the effective sphere to the backbone C alpha atom, b is the persistence length of unfolded protein (2-3 residues), and n is the number of persistence lengths. Entropy loss may be added for each strand of protein (N and C) that extends from the functionalized location.

Use of the Energy Function a) Combinatorial Unfolding

The energy function described above may be applied to calculate the free energy of unfolding for one or several sets of amino acid residues of a protein of interest. The sets may comprise any selection of any number of amino acid residues in the model of the protein of interest. The sets may also be restricted to certain types of subsequences of amino acid residues of the protein of interest and within one or more specified regions of the protein of interest. For example, the types of sets may comprise: all sets comprising a sequence of one or more contiguous amino acid residues in the model; all sets comprising a sequence of one or more contiguous amino acid residues in the model, wherein each set comprises at least one residue in the region; all sets comprising two or more non-contiguous sequences of one or more contiguous amino acid residues in the model; all sets comprising two or more non-contiguous sequences of one or more amino acid residues in the model, wherein each set comprises at least one amino acid residue in the region; sets limited to amino acid residues sequences having a length between a minimum length and a maximum length, or any combination of the foregoing.

The minimum length and maximum length may be selected based upon the amino acid resides sequence lengths of candidate epitopes that are desired. Any lengths may be selected that are less than or equal to the total length of the protein of interest. For example, the minimum length and the maximum length may be between about 3 to about 20; alternatively the minimum length and the maximum length may be between about 5 and about 15

Figure 2:
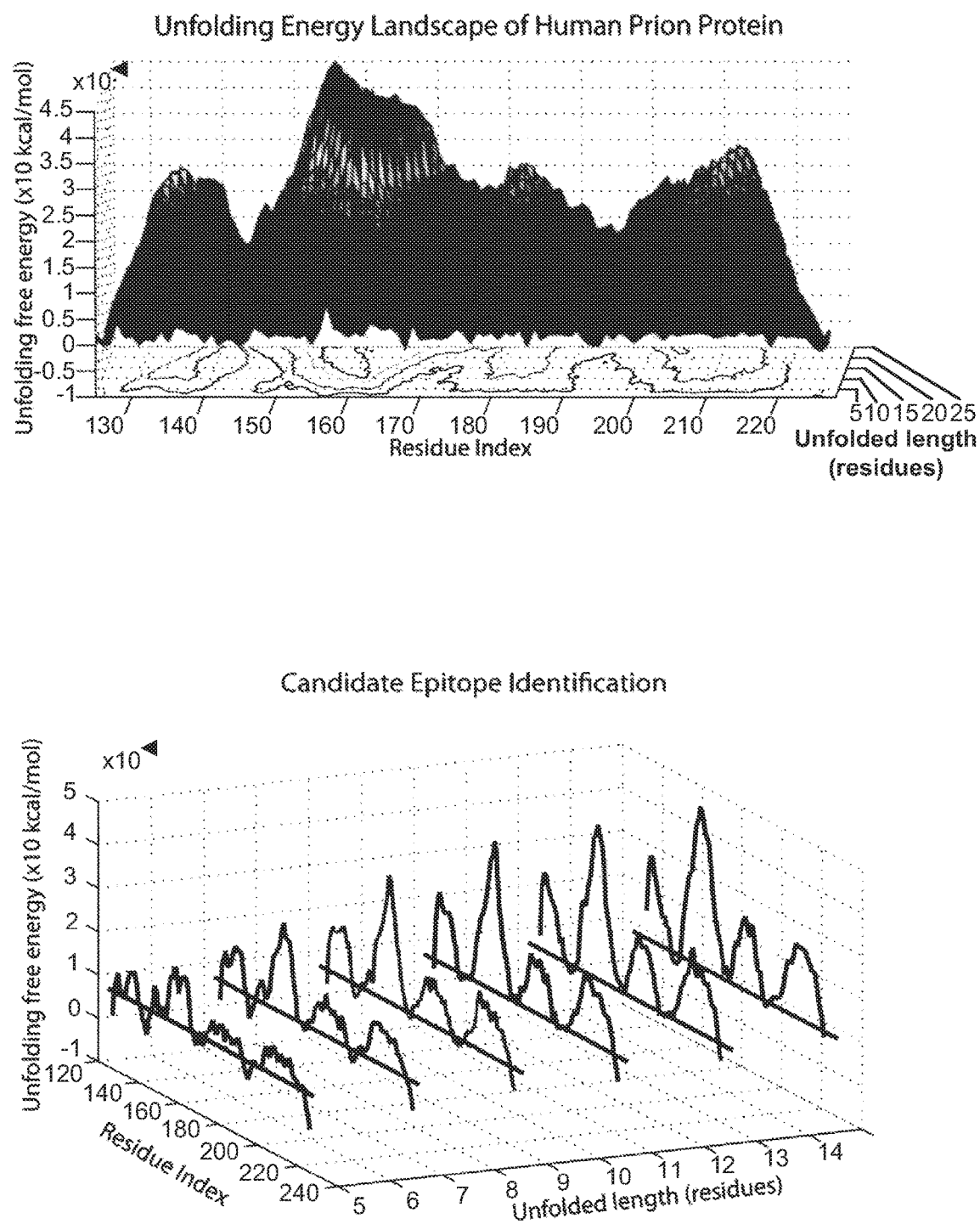
FIG. 2 provides two graphs of exemplary unfolding energy landscapes for the human prion protein.

In one particular embodiment, a plurality of sets of amino acid residues may be formed by iteratively unfolding one contiguous subsequence of one or more amino acids of the protein at a time, and applying the sets in the context of predicting rates and folding mechanisms. The unfolded subsequences may vary in length from 1 residue up to the total number of residues in the protein and in location from starting at the first residue to starting at the last residue less the number of residues in the unfolded region plus 1. For example, for a protein of length 100 residues, this results in an ensemble of 5050 sets representing 5050 partially unfolded states of the protein. For each set, the free energy of unfolding may be calculated as described above. The free energy of these sets may be represented on a three dimensional graph, with the location of the middle residue of the set on the x axis, the length of the unfolded region on the y axis, and the free energy of unfolding on the z axis. In keeping with the above-mentioned single-sequence approximation, where one contiguous subsequence of the protein may be unfolded at a time, this graph may be termed a single sequence energy landscape. For example, referring to FIG. 2, two exemplary graphs depicting single sequence energy landscapes for the human prion protein are shown. Treating these sets as an ensemble, the equilibrium probability of unfolding for each set may be calculated by dividing the Boltzmann factor for each set by the partition function as described in the background, with the approximation that all configurational states corresponding to the same stretch of unfolded protein have the same total energy. These equilibrium probabilities may then be plotted as a function of unfolding sequence position and length. To obtain the total probability of unfolding of a residue, the equilibrium probabilities of all sets containing this residue in the unfolded configuration may be summed. The total probabilities of unfolding thus obtained for all residues may be plotted as a function of residue number in the protein.

Identifying the regions of the protein with the highest total probability of unfolding is equivalent to finding the minima in the energy landscape, which may be done initially by visual inspection of the results, and then refined by examining the magnitude of the depth of a valley on the free energy landscape. The average free energy of unfolding a set comprising an amino acid residue sequence of fixed length may be calculated, and all sets comprising an amino acid residue sequence of the same fixed length with a free energy of unfolding less than the average energy by an amount E may be identified. This calculation may be repeated for all subsequence lengths of interest. The average energy of unfolding minus the amount E may be referred to as the "minimum energy", and may vary for each subsequence length for which it is calculated. In one embodiment, E may be equal to or greater than 1.4 kcal/mol, corresponding to a tenfold increase in the probability of unfolding over a set with the average free energy of unfolding; alternatively E may be equal to of greater than 3 kcal/mol, corresponding to a hundredfold increase in the total probability of unfolding. For the purpose of selecting unfolding-prone regions for candidate epitopes, minima corresponding to an unfolded sequence length of about 3 to about 20 may be acceptable; alternatively the length of the unfolded sequence may be between about 5 and about 15. In one embodiment, for a protein of length 100 residues, not more than the five most pronounced minima in the single sequence landscape and their corresponding candidate epitopes are selected for further analysis. In alternative embodiments, more or less than the five most pronounced minima may be selected for further analysis.

In another embodiment, sets are formed by unfolding two noncontiguous or contiguous subsequences of the protein at a time, resulting in a five dimensional object termed a double sequence energy landscape. This may be projected to a 3-dimensional graph depicting residue index on the x-axis, total number of unfolded residues on the y-axis, and free energy or probability of unfolding on the z-axis. The double-sequence energy landscape may be useful for identifying interactions between unfolding events at different sites, and illustrate how unfolding of part of a protein may increase the susceptibility of another part of the protein to unfolding. Accordingly, the structural consequences of having a candidate epitope region unfolded on the remainder of the folded structure may be determined. Additionally or alternatively, correlated and co-operative unfolding behavior that suggests an additional candidate epitope not apparent from the single sequence energy landscape may be determined.

In yet another embodiment, the energies of unfolding for all sets of all possible numbers of contiguous or noncontiguous subsequences of the protein of interest may be calculated, yielding a multidimensional energy landscape. This produces an exhaustive ensemble of partially unfolded states. However, this approach may be computationally laborious and may therefore be used where a complete exposition of all partially unfolded states is desirable, for example, for constructing a protein unfolding mechanism. This method uses the energy functions described above to calculate the free energy of unfolding for all possible sets of residues within the protein. The sets of amino acid residues are no longer required to be contiguous. The minimum unfolding free energies are identified, and the corresponding amino acid residue subsequences (one or more from each partially unfolded structure) are chosen as candidate epitopes. This method exhaustively searches for combinations of unstable regions that may not be apparent from unfolding of a single contiguous strand.

In yet a further alternative embodiment, epitopes are identified from sets having a total probability of unfolding above a minimum probability. The sets may comprise any variation of contiguous or non-contiguous amino acid residues sequences as desired. The total probability of unfolding of an epitope is determined as the sum of the equilibrium probabilities of unfolding of all of the sets comprising the amino acid residue sequence of the epitope. Epitopes having a total probability of unfolding above a "minimum probability" are then identified for further analysis. The minimum probability may vary depending on the length of the epitope under consideration and may be defined as a multiple of the average total probability of unfolding of all sets having subsequences of contiguous amino acid residues of the same length in the protein. Any value of the multiple may be selected in order to select epitopes having a total probability of unfolding above a desired minimum probability. In one embodiment, the multiple may be 10 or more. In an alternative embodiment, the multiple may be 100 or more.

As input, the epitope prediction method may accept the atomic resolution structure of a protein of interest or portion thereof (such as a protein domain or fragment) as determined by high resolution techniques like nuclear magnetic resonance or X-ray crystallography or electron microscopy or other methods. The structure may have a resolution of about 10 Angstroms or less, or may have a resolution of about 5 Angstroms or less. The atomic resolution structure of the protein of interest may be directly available or may be determined based on the atomic resolution structure of another protein(s) or polypeptide(s) with amino acid sequence similarities to the protein of interest. For example, the structure of the human TNF receptor may be obtained from the PDB (ID code 1TNR) and may be used directly. Alternatively, the structure of fas may be determined based on homology modelling to 1TNR as determined by the structure prediction program LOMETS or I-TASSER (Yang Zhang. I-TASSER server for protein 3D structure prediction. BMC Bioinformatics, vol 9, 40 (2008), (http://zhang.bioinformatics.ku.edu/LOMETS/); followed by equilibration/minimization for 20 ns with MD. Peptide numbering may be assigned according to the relevant structure in the PDB. In the further alternative, the epitope prediction method may accept as input structures of the protein of interest having a non-atomic resolution. For example, structures of the protein of interest having a residue resolution may be input.

In cases where the structure of a protein of interest has not yet been solved with sufficient precision, the structure of a protein known to have a high degree of sequence homology to the protein of interest may be used in its place and the minima of its free energy landscape determined by the first two components of the method. For example, a high degree of sequence homology includes an amino acid sequence which may be at least 50%, 55%, 60%, 65%. 70%, 75%, 80%, 85%, 90% or 95% identical or similar, or at least 96%, 97%, 98% or 99% identical or similar to another amino acid sequence. By "similar" is meant that the amino acid sequence of the protein of interest differs from that of another amino acid sequence by "conserved amino acids" or "conservative amino acids," when optimally aligned. Conserved amino acids classifications may be based on considerations of hydrophilicity or hydrophobicity, size or volume, or charge. Amino acids can be generally characterized as hydrophobic or hydrophilic, depending primarily on the properties of the amino acid side chain. A hydrophobic amino acid exhibits a hydrophobicity of greater than zero, and a hydrophilic amino acid exhibits a hydrophilicity of less than zero, based on the normalized consensus hydrophobicity scale of Eisenberg et al. (*J. Mol. Bio.* 179:125-142, 184). Hydrophobic amino acids include Gly, Ala, Phe, Val, Leu, Ile, Pro, Met and Trp, and hydrophilic amino acids include Thr, His, Glu, Gln, Asp, Arg, Ser, and Lys.

In some embodiments, the term "conserved amino acids" or "conservative amino acids" refers to amino acids having a similar hydrophilicity value (e.g., within a value of plus or minus 2.0, or plus or minus 1.5, or plus or minus 1.0, or plus or minus 0.5), where the following may be an amino acid having a hydropathic index of about −1.6 such as Tyr (−1.3) or Pro (−1.6) are assigned to amino acid residues (as detailed in U.S. Pat. No. 4,554,101, incorporated herein by reference): Arg (+3.0); Lys (+3.0); Asp (+3.0); Glu (+3.0); Ser (+0.3); Asn (+0.2); Gln (+0.2); Gly (0); Pro (−0.5); Thr (−0.4); Ala (−0.5); His (−0.5); Cys (−1.0); Met (−1.3); Val (−1.5); Leu (−1.8); Ile (−1.8); Tyr (−2.3); Phe (−2.5); and Trp (−3.4).

In alternative embodiments, conserved amino acids refers to amino acids having a similar hydropathic index (e.g., within a value of plus or minus 2.0, or plus or minus 1.5, or plus or minus 1.0, or plus or minus 0.5). In such embodiments, each amino acid residue may be assigned a hydropathic index on the basis of its hydrophobicity and charge characteristics, as follows: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5).

In alternative embodiments, conserved amino acids are divided into non-polar, acidic, basic and neutral classes, as follows: non-polar: Ala, Val, Leu, Ile, Phe, Trp, Pro, Met; acidic: Asp, Glu; basic: Lys, Arg, His; neutral: Gly, Ser, Thr, Cys, Asn, Gln, Tyr.

Hydrophobic or hydrophilic amino acids can be further subdivided based on the characteristics of their side chains. For example, an aromatic amino acid is a hydrophobic amino acid with a side chain containing at least one aromatic or heteroaromatic ring. Aromatic amino acids include Phe, Tyr, and Trp. An apolar amino acid is a hydrophobic amino acid with a side chain that is uncharged at physiological pH and which has bonds in which a pair of electrons shared in common by two atoms is generally held equally by each of the two atoms (i.e., the side chain is not polar). Apolar amino acids include Gly, Leu, Val, Ile, Ala, and Met. Apolar amino acids can be further subdivided to include aliphatic amino acids, which is a hydrophobic amino acid having an aliphatic hydrocarbon side chain. Aliphatic amino acids include Ala, Leu, Val, and Ile.

A polar amino acid is a hydrophilic amino acid with a side chain that is uncharged at physiological pH, but which has one bond in which the pair of electrons shared in common by two atoms is held more closely by one of the atoms. Genetically encoded polar amino acids include Ser, Thr, Asn, and Gln. An acidic amino acid is a hydrophilic amino acid with a side chain pKa value of less than 7. Acidic amino acids typically have negatively charged side chains at physiological pH due to loss of a hydrogen ion. Acidic amino acids include Asp and Glu. A basic amino acid is a hydrophilic amino acid with a side chain pKa value of greater than 7. Basic amino acids typically have positively charged side chains at physiological pH due to association with hydronium ion. Basic amino acids include Arg, Lys, and His.

It will be appreciated by one skilled in the art that the above classifications are not absolute and that an amino acid may be classified in more than one category. In addition, amino acids can be classified based on known behaviour and or characteristic chemical, physical, or biological properties based on specified assays or as compared with previously identified amino acids.

Candidate epitopes may be found by examining regions likely to unfold in a hypothetical protein with the known structure, but with the sequence of interest, i.e. the sequence is structurally aligned to the protein of highest sequence homology. These may be compared to candidate epitopes for the sequence whose structure has been determined to provide additional information as the local stability of candidate epitopes.

Alternatively, the structure may be determined by ab initio prediction based on the primary protein sequence.

b) Analytical Models of Unfolding

The 2-state nature of the model, with an amino acid being folded or unfolded, allows for a mapping to an Ising-like model. Ising-like models have been introduced for protein folding (Munoz and Eaton, Proc Natl Acad Sci USA 96, 11311 (1999)), and may be adapted to the present invention to model unfolding and misfolding. The partition function for a partially unfolded protein with one or more sequence strands melted out may be found using the energy function described above along with statistical mechanics tools.

In the Ising-model formalism, the energy function contains non-local interactions representing interacting amino acids distant in sequence but close in space. Partial traces performed analytically over states may exceed the efficiency of the combinatorial component of the method, and allow for multiple contiguous sequences to be simultaneously unfolded. The combinatorial component of the method may, where appropriate, be substituted by analytic methods involving partial traces with statistical mechanics tools.

c) Selection of Epitopes Based on the Candidates from the Energy Landscapes

Those candidate misfolding-specific epitopes chosen by inspection of the energy landscapes may be refined to select for further development those epitopes that will selectively bind the misfolded protein with high affinity and not the normally folded protein nor other proteins within the organism's proteome. For this purpose, a series of screening steps may be implemented as the third component of the method:

To enhance the probability that a candidate epitope is adequately immunogenic for antibodies to be raised against it, its sequence may be inspected for the presence of an adequate number of hydrophilic residues (namely arginine, asparagine, aspartate, cysteine, glutamine, glutamate, histidine, lysine, methionine, serine, threonine, tryptophan, and tyrosine), which maybe generally more immunogenic than hydrophobic residues. Approaches for estimating the immunogenicity of epitopes for antibody production by a B-cell response have been developed elsewhere (Roggen Immunogenicity of Biopharmaceuticals 8, 75 (2008)) and may be used to score the candidate epitopes for their probability of eliciting robust antibody production.

To reduce the probability that a candidate epitope is not immunoreactive against the protein containing it in a native conformation, the solvent exposure of the epitope in the native structure may be investigated. The epitope may be minimally solvent-exposed in the nature structure, as this raises the probability of selective immunoreactivity on misfolding. However, it often happens that significant parts, especially hydrophilic and charged groups, of the epitope are solvent exposed in the folded state. Candidate epitopes that have these hydrophilic or charged groups exposed in a way that could replicate a free peptide are discarded, but those that have a configuration that would not be replicated by a free peptide of the same sequence are retained. For example, this may occur when hydrophilic or polar groups are exposed on separate faces of a protein in the native structure that would not be simultaneously accessible to recognition by an antibody. In cases where a set of structures for a protein are available, the root-mean square deviation of all regions in the protein may be calculated and used to refine the choice of epitopes. Those regions with large RMSD in the folded state are less desirable as epitopes because this is an indication of greater mobility.

Figure 4:
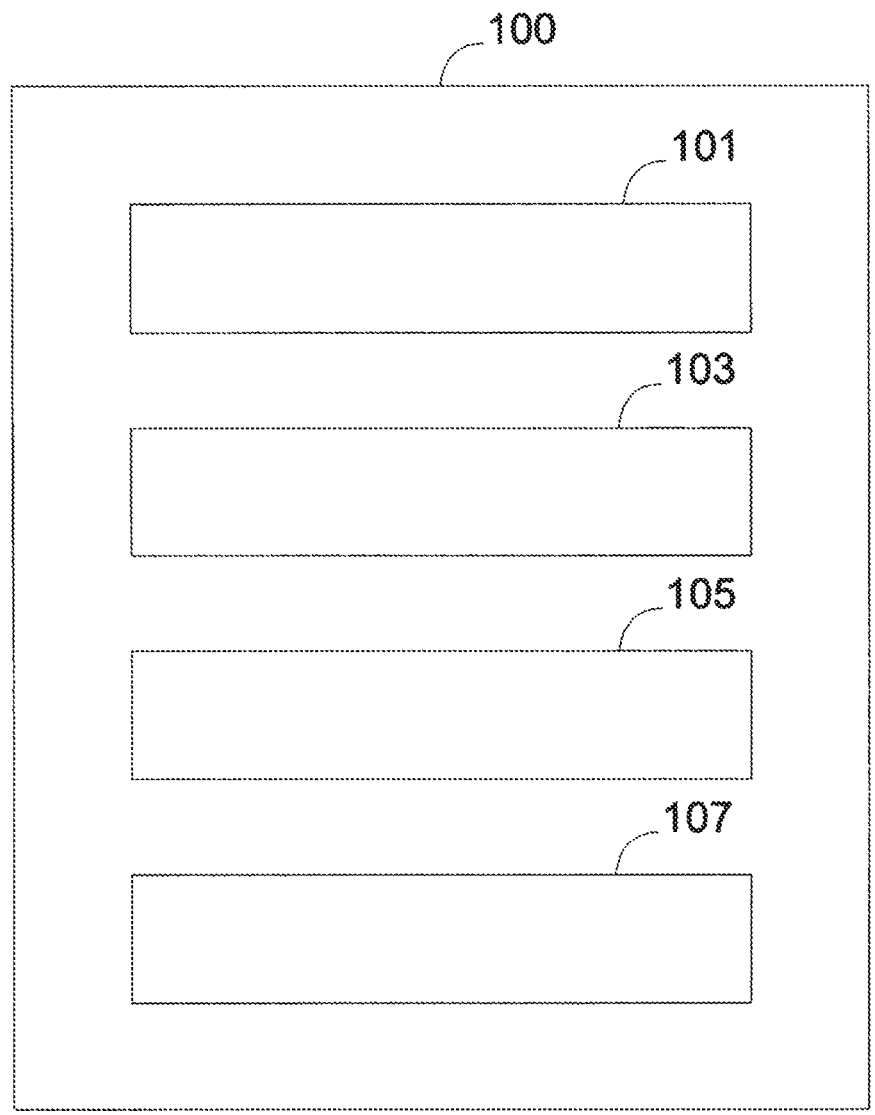
FIG. 4 is a system diagram of a system for identifying epitopes in regions of a protein that are prone to unfolding according to another embodiment of the invention.

To reduce the probability that the candidate epitope is not present in other proteins in the target organism, a search of the epitope sequence may be conducted for example by protein BLAST, which can identify similar sequences in the organism's proteome. These similar sequences may cause undesirable cross reactions on exposure to agents targeting the candidate epitope that would compromise its diagnostic or therapeutic usefulness. In general, the candidate sequence should share less than 80% of its residues in order with others in the proteome; a very distinct epitope would have a minimal similarity and for example it should share less than 50% with other protein sequences in the genome.

Those candidate epitopes that satisfy one or more of the criteria listed above may then be accepted as misfolding specific epitopes.

In one embodiment, the method thus comprises but is not limited to the following parts:

a) An energy function for determining the Gibbs or Helmholtz free energy of unfolding for any set of one or more amino acid residues contained within the amino acid sequence of a protein with a secondary or tertiary structure. This free energy function may take several forms as explained in detail below, but most generally takes into account all of the following energetic contributions to the free energy of unfolding: enthalpy change, solvation entropy change, configurational entropy change, energy of salt bridge breakage, pH-dependent ionization energy of acidic and basic residues, energy of transfer of charged groups between dielectric environments, and glycan and/or disulfide bond stabilization (if the protein of interest contains these structural elements).

b) A method for applying the free energy function to the calculation of unfolding free energies and total probabilities of unfolding for all or several sets of one or more amino acids of the protein of interest and representing the resulting energies in a form suitable for interpretation. In a particular instance of the method, this involves calculating the free energy of unfolding for sets of all contiguous subsequences of amino acid residues contained within the protein's sequence and representing the free energies on a three dimensional surface plot that shows free energy or total probability of unfolding as a function of unfolded subsequence length and position in the protein sequence. Another particular instance of the method, involves calculating the free energy of all partially unfolded states containing two unfolded subsequences (known as the "double-sequence approximation in the field of protein folding). The unfolded sequences corresponding to minima on the unfolding energy landscape surface are identified as regions most likely to unfold and are therefore candidates for misfolding specific epitopes.

c) Taking the candidate misfolding specific epitopes defined in part b) and analyzing their immunogenicity, propensity to be immunoreactive in the folded form of the protein, and occurrence in other proteins of the proteome. Only those candidate epitopes determined to be immunogenic, nonreactive to antibodies when the protein of interest is in its folded form, and not present in other cell surface or extracellular proteins in a way likely to cause cross-reactivity are selected.

d) A method that predicts misfolding specific epitopes in proteins based on calculation of the free energy of unfolding for all possible sequence-contiguous candidate epitopes contained within the protein. The method identifies these regions by generating a free energy landscape of the unfolding events, where relatively probable unfolding events are located at minima or valleys on a free energy surface. The method is also able to describe the energy contour around these minima, thereby determining the probability of a given unfolding event predisposing to other more extensive unfolding events.

e) A method for identifying the immunogenicity of regions found to have a relatively high probability of unfolding, to be used as epitopes for the development of antibodies, and isolating those epitopes that are expected to be immunoreactive only in the unfolded or misfolded state. A prominent and practical advantage of this approach is that antibodies raised against free peptides defined by the method, by virtue of the lack of secondary or tertiary structure in the immunogen and the screening target, are highly likely to specifically recognize the identical extended linear unfolded sequence in the partially denatured parent protein.

Referring to FIG. 1, a flowchart is shown describing the steps of one embodiment of method is shown.

System for Identifying Epitopes In an alternative embodiment, the epitope prediction methods described above are implemented in a system for identifying epitopes present in a misfolded form in a protein. Referring to FIG. 4, a system 100 is shown comprising an input unit 101, a candidate selection unit 103, a free energy computation unit 105 and an epitope identification unit 107.

In the present embodiment, the system 100 comprises a computer having a processor and memory (not shown). The memory contains statements and instructions recorded thereon that when executed by the processor provide the functionality of the input unit 101, the candidate selection unit 103, the free energy computation unit 105 and the epitope identification unit 107 described herein. In alternative embodiments, the input unit 101, the candidate selection unit 103, the free energy computation unit 105 and the epitope identification unit 107 may be comprised of one or more processors and memories located at one more locations communicating through one or more networks. The processors may be comprised on one or more computers, application specific circuits, programmable logic controllers, field programmable gate arrays, microcontrollers, microprocessors, virtual machines, electronic circuits and other processing devices known to one skilled in the art. Further, the memories may be comprised of one or more random access memories, flash memories, read only memories, hard disc drives, optical drives and optical drive media, flash drives, and other computer readable storage media known to one skilled in the art.

The input unit 101 is configured to receive a model representing the structure of a protein. As described above, the input unit 101 may accept an atomic model of the protein obtained from using techniques, such as, nuclear magnetic resonance, X-ray crystallography, electron microscopy, and other methods known in the art. In addition, the input unit 101 is also configured to receive operational parameters defining the operation of the system 100, including, the regions of the modelled protein to be evaluated for unfolded protein epitopes, the types of sets of amino acids in the regions to be selected, and parameters of the free energy of unfolding function as described above. In the present embodiment, the input unit 101 receives the model of the protein and the operational parameters by reading configuration data stored in the memory of the system 100. In an alternative embodiment, the input unit 101 may receive the model representing the protein and the operational parameters from through any means know in the art, such as, for example, manual entry through a keyboard, or accessing data in a remote server. In a further alternative embodiment, the input unit 101 may receive one or more of the model representing the protein, the operations parameters described above, and other operational parameters apparent to one skilled in the art.

The candidate selection unit 103 is configured to select from the model one or more sets of one or more amino acid residues. The parameters specifying the types of sets to be selected is provided to the candidate selection unit 103 by the input unit 101. The types of sets may be selected with respect to location in the model, length, and the number of non-contiguous sequences of amino acid residues. For example, the types of sets may comprise: all sets comprising a sequence of one or more contiguous amino acid residues in the model; all sets comprising a sequence of one or more contiguous amino acid residues in the model, wherein each set comprises at least one residue in the region; all sets comprising two or more non-contiguous sequences of one or more contiguous amino acids residues in the model; all sets comprising two or more non-contiguous sequences of one or more amino acid residues in the model, wherein each set comprises at least one amino acid residue in the region; and sets limited to amino acid residues sequences having a length between a minimum length and a maximum length, or any combination of the foregoing.

In an alternative embodiment, the parameters specifying types of sets to be selected and/or the region to be evaluated are not received by the input unit 101 and the candidate selection unit 103 is preconfigured to select specific types of sets and/or specific regions. For example, the candidate selection unit 103 may be configured to select all sets comprising sequences of one or more contiguous amino acid residues in the entire model.

The free energy computation unit 105 is configured to determine the free energy of unfolding for each set selected by the candidate selection unit 103 by applying the free energy of unfolding function described above. In the present embodiment, the free energy computation unit 105 is configured to determine each element of the free energy of unfolding function using all-atom molecular dynamics or changes in solvent accessible surface area or changes in the number of non-hydrogen atoms in spatial proximity for enthalpy changes, changes in solvent-accessible surface area for solvation entropy changes, an analytic diffusion model for configurational entropy changes and post-translational modification effects, continuum electrostatics calculations with either a constant or spatially-varying dielectric constant from the Poisson-Boltzmann equation or the Coulomb equation for salt bridge energies and charge transfer energies. In alternative embodiments, the free energy computation unit 105 may determine each element of the free energy of unfolding function using one or the average of two or more of the methods described above for the determination of each element.

The epitope identification unit 107 is configured to identify one or more epitopes present in a misfolded form of the protein by one of two methods. The epitopes can be identified by either (a) determining the total probability of unfolding for each residue in the region and identifying epitopes from the sets having a total probability of unfolding above a minimum probability, or (b) identifying epitopes from the sets having a free energy of unfolding below a minimum energy. The epitope identification unit 107 identifies epitopes by storing data describing the epitopes in the memory of the system 100. In alternative embodiments, the epitopes may be identified by presenting graphical or numerical depiction on a display or printed medium.

In operation, a model of a protein to be evaluated for unfolded protein epitopes and the operational parameters are stored as configuration data in the memory of system 100. The input unit 101 receives the model of the protein and operational parameters by reading the configuration data from the memory. The candidate selection unit 103 then selects sets of amino acid residues in the model of the character specified in the operational parameters received by the input unit 101. The free energy computation unit 105 then determines the free energy of unfolding for each set selected by the candidate selection unit 103. Based on the free energy of unfolding determined for each set by the free energy computation unit 105, the epitope identification unit 107 identifies epitopes by either (a) determining the total probability of unfolding for each residue in the region and identifying epitopes from the sets having a total probability of unfolding above a minimum probability, or (b) identifying epitopes from the sets having a free energy of unfolding below a minimum energy. The epitope identification unit 107 then stores data describing the epitopes to the memory of the system 100.

EXEMPLARY EMBODIMENTS

Figure 3:
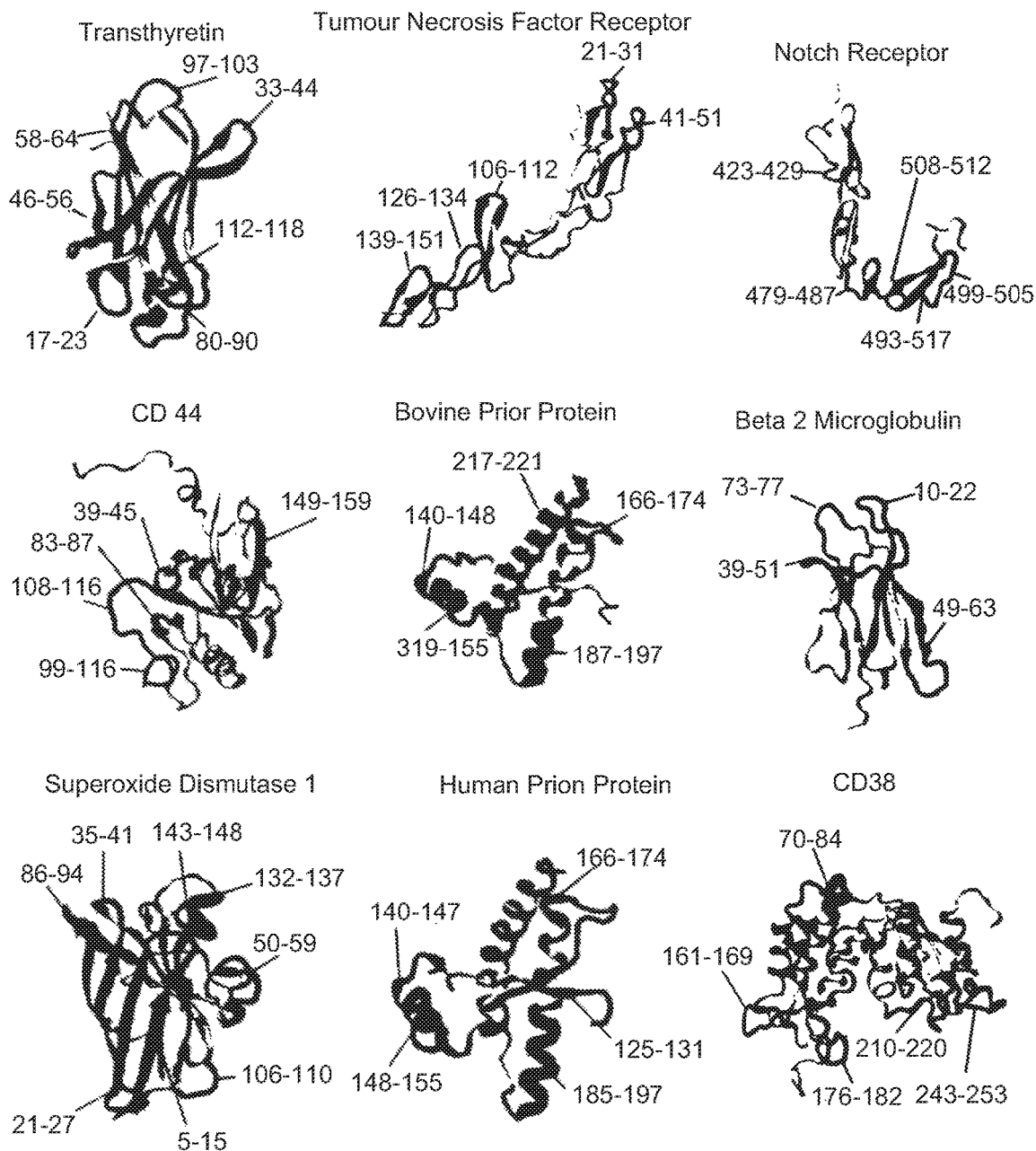
FIG. 3 is a depiction of exemplary unfolding-specific epitopes identified for 9 proteins involved in misfolding diseases and cancer.

We have used the epitope prediction methods described herein to identify the misfolding specific epitopes of human prion protein, bovine prion protein, human superoxide dismutase 1, human transthyretin, human $\beta_2$ microglobulin, human Notch receptor, human CD38, human CD44, human tumor necrosis factor receptor, human FAS receptor and human epidermal growth factor receptor. We implemented the above steps described in the detailed description of the invention to obtain the sequences as shown in FIG. 3 and as listed in Table 1 below.

TABLE 1

| Protein Target (abbr) UniProtKB/ SwissProt # | Residue span | Sequence | SEQ ID No. |
|---|---|---|---|
| Human prion protein (hPrP) P04156 residues 1-230 | 125-131 | LGGYML | 1 |
| | 126-134 | GGYMLGS | 2 |
| | 140-147 | HFGSDYED | 3 |
| | 143-147 | SDYED | 4 |
| | 148-155 | RYYRENMH | 5 |
| | 151-155 | RENMH | 6 |
| | 160-166 | QVYYRPM | 7 |
| | 166-174 | PMDEYSNQNN | 8 |
| | 167-174 | MDEYSNQNN | 9 |
| | 185-197 | KQHTVTTTTKGEN | 10 |
| Bovine prion protein (bPrP) P10279 residues 25-241 | 140-148 | HFGSDYEDR | 11 |
| | 139-155 | IHFGSDYERYYRENMH | 12 |
| | 166-174 | VDQYSNQNN | 13 |
| | 187-197 | HTVTTTTKGEN | 14 |
| | 217-221 | QYQRE | 15 |
| Human transthyretin (hTTR) P02766 residues 21-147 | 17-23 | LDAVRGS | 16 |
| | 33-43 | FRKAADDTWE | 17 |
| | 46-56 | SGKTSESGELH | 18 |
| | 58-64 | LTTEEQ | 19 |
| | 80-90 | KALGISPFHEH | 20 |
| | 97-103 | ANDSGPR | 21 |
| | 112-118 | SPYSYST | 22 |
| Human $\beta_2$ microglobulin ($\beta$2M) P61769 residues 22-119 | 10-22 | YSRHPAENGKSNF | 23 |
| | 39-51 | LLKNGERIEKVEH | 24 |
| | 49-63 | VEHSDLSFSKDWSFY | 25 |
| | 73-77 | TEKDE | 26 |
| Human Cu/Zn superoxide dismutase (hSOD1) P00441 residues 2-154 | 5-15 | VCVLKGDGPVQ | 27 |
| | 9-16 | KGDGPVQG | 28 |
| | 21-27 | EQKESNG | 29 |
| | 35-41 | IKGLTEG | 30 |
| | 50-59 | FGDNTAGCTS | 31 |
| | 50-60 | FGDNTAGCTSA | 32 |
| | 86-94 | NVTADKDGV | 33 |
| | 87-95 | VTADKDGVA | 34 |
| | 106-110 | LSGDH | 35 |
| | 105-112 | SLSGDHCI | 36 |
| | 132-137 | EESTKT | 37 |
| | 133-139 | ESTKTGN | 38 |
| | 143-148 | RLACGV | 39 |
| | 143-153 | RLAXGVGIAQ (X = cysteic acid) | 40 |
| Human CD38 P28907 residues 1-300 | 70-84 | YTEIHPEMRHVDCQS | 41 |
| | 161-169 | GEFATSKIN | 42 |
| | 176-182 | WRKDCSN | 43 |
| | 210-220 | GSRSKIFDKDS | 44 |
| | 243-253 | IHGGREDSRDL | 45 |

TABLE 1-continued

| Protein Target (abbr) UniProtKB/ SwissProt # | Residue span | Sequence | SEQ ID No. |
|---|---|---|---|
| Human CD44 P16070 residues 21-742 | 39-45 | NGRYSIS | 46 |
| | 83-87 | EGHVV | 47 |
| | 108-116 | TSNTSNYDT | 48 |
| | 149-159 | NRDGTRYVQKG | 49 |
| | 99-116 | ANNTFVYILTSNTSNYDT | 50 |
| Human tumour necrosis factor receptor (hTNFR) P19438 | 21-31 | IHPQNNSICCT | 51 |
| | 41-51 | NDCPGPGQDTD | 52 |
| | 106-112 | YWSENLF | 53 |
| | 126-134 | HLSCQEKQN | 54 |
| | 139-151 | CTCHAGFFLRENECV | 55 |
| Human notch protein (hNOTCH1) P46531 residues 1-2550 | 423-429 | CEHAGKC | 56 |
| | 479-487 | MPGYEGVHC | 57 |
| | 499-505 | CLHNGRC | 58 |
| | 508-512 | KINEF | 59 |
| | 493-517 | ECASSPCLHNGRC→LDKINEFQCECP | 60 |
| Human FAS (hTNFR6) P25445 residues 1-335 | 52-60 | LHHDGQFCH | 61 |
| | 70-80 | ARDCTVNGDEP | 62 |
| | 105-111 | RLCDEGH | 63 |
| | 136-142 | NSTVCEH | 64 |
| | 167-189 | EEPSRSNLGWLCL | 65 |
| Human epidermal growth factor receptor (hEGFR) P00533 residues 25-1210 | 11-25 | SNKLTQLFTFEDHFL | 66 |
| | 46-56 | VQRNYDLSFLK | 67 |
| | 83-95 | IRGNMYYENSYAL | 68 |
| | 97-107 | VLSNYDANKTG | 69 |
| | 143-155 | IVSSDFLSNMSMD | 70 |
| | 148-169 | FLSNMSMDFQNHLGS | 71 |
| | 176-181 | WGAGEE | 72 |
| | 241-259 | PPLMLYNPTTYQMDVNPE | 73 |
| | 257-266 | PEGKYSFGAT | 74 |
| | 273-282 | RNYVVTDHGS | 75 |
| | 288-301 | GADSYEMEEDGVRK | 76 |
| | 314-328 | NGIGIGEFKDSLSIN | 77 |
| | 328-337 | ATNIKHFKN | 78 |
| | 348-363 | LPVAFRGDSFTHTPPL | 79 |
| | 465-474 | KIISNRGENS | 80 |

The peptides listed in Table 1 constitute valuable embodiments of the present invention, in their isolated form, i.e., in a form removed from the parent peptide in which these sequences are resident and, preferably, in a form from which all other peptides are essentially absent.

It will be appreciated from a review of Table 1 that the method according to the invention can take the multitude of potential epitopes in a protein of interest and reduce them to 100, 50, 20, 10 or fewer misfolding specific epitopes.

It is intended that these epitopes are examples of the capability of the present invention for identification of disease specific epitopes. All epitopes identified using the epitope prediction methods of this invention on a protein, and antibodies raised to be immunoreactive to them, are considered aspects of the present invention.

It is noteworthy that the application of the epitope prediction methods according to the invention may identify epitopes already claimed in other earlier patents as misfolding specific epitopes. Thus we exclude from the claims of this patent those epitopes identified by the present invention but identified by other means and claimed previously for the purpose of selectively identifying misfolded proteins such as Super Oxide Dismutase 1 (SOD) epitopes previously claimed in PCT application number PCT/CA2007/0000346 and US patents US20080206251A1 and US20070292410A1.

The invention relates to epitopes that are presented "uniquely" by the misfolded form of a protein, relative to the natively folded form of that protein.

Presentation of the epitope provides a basis for distinguishing between the two forms of the protein, allows the misfolded protein to be targeted, and substantially removes the natively folded protein as a complicating factor in therapeutic and diagnostic applications of the invention. In principle, an epitope is unique to a misfolded protein if an antibody or other ligand that binds that epitope does not bind to, or shows significantly reduced binding to, the natively folded form of that protein. The particular magnitude of the difference in binding is not critical, provided the binding difference is effective to yield a discernible test result or therapeutic result. Thus, the present epitopes, and the methods used to identify them, provide a basis for distinguishing between the misfolded and natively folded forms of the same protein.

The misfolded form of a protein is characterized, in the present context, as a form that presents an epitope not found in the natively folded protein. This typically results from the protein adopting a different conformation, resulting from different environmental conditions (for example, oxidation of cysteine), defects in protein folding surveillance (for example, ineffective chaperone function), aberrant post-translational modifications (for example, defective maturation of glycosylation), abnormal interaction with another protein (for example, $PrP^C$-$PrP^{Sc}$ interaction), or from genetic mutation. As a result of misfolding, the protein can adopt an unusual and undesirable aggregated state. Alternatively, the misfolded protein can remain unassociated with other proteins but with a different immunogenicity relative to its normal state. It is to be understood that the misfolded form of a protein includes transiently misfolded states, for example, when the protein has adopted a partially unfolded conformation during misfolding and, optionally, aggregation.

As used herein, the term "epitope" refers a region of a protein that is recognized by a B cell or T-cell receptor, or an antibody or a binding fragment thereof and is represented herein by linear peptides having amino acid sequences that are found in the parent protein in which the epitope resides. It is to be understood an epitope according to the invention includes epitopes within a protein that may be exposed transiently, for example, when the protein has adopted a partially unfolded conformation during misfolding and, optionally, aggregation. As noted herein above, the epitope will usually comprise at least 3 contiguous residues, representing the minimal domain necessary for antibody binding. However, it will be appreciated that the epitope can include a larger number of contiguous residues, such as 5 residues, 7 residues which typically is the length required for minimal immunogenicity within common antibody production hosts, 10 residues, 15 residues, 20 residues or more. The criticality lies in providing an epitope that harbours an antibody-binding domain. Thus, and with reference to Table 1, it is to be appreciated that the peptides specifically listed may, in addition to serving per se as epitopes, further comprise additional amino acid residues at one or both flanks thereof, particularly for those peptides that consist of fewer than 7 residues. The additional residues can be those normally associated with the peptide in the context of the parent protein. Conversely, it should be appreciated that truncated forms of the peptides can also serve as epitopes, especially when the peptide consists of more than 7 residues. The extent of truncation can vary depending on the actual length of a given peptide. Any contiguous 7 residues within a listed peptide can be expected to be immunogenic per se, and any 3, 4, 5, 6, or 7 contiguous residues or more can be expected to be useful as an epitope to which antibodies can bind.

For example, when applied to human PrP c protein, the epitope prediction methods predict an unfolding event that presents an epitope within beta strand 1, represented by the sequence YML, that is common to both predicted peptides, LGGYML and GGYMLGS (SEQ ID Nos. 1 and 2, respectively. It will be appreciated from the discussion above that variations of these specific peptides that also comprise YML and are based also on parent protein sequence are included in embodiments of the present invention. Such peptides can include, for instance, GGYMLGS (SEQ ID NO: 81), GGYMLG (SEQ ID NO: 82), GYMLGS (SEQ ID NO: 83), GGYML (SEQ ID NO: 84), YMLGS (SEQ ID NO: 85), GYML (SEQ ID NO: 86), YMLG (SEQ ID NO: 87) and YML (SEQ ID NO: 88).

It will be appreciated that the epitopes and other free peptides mentioned herein can be prepared by solid or solution phase synthesis in accordance with standard practice, and isolated and optionally purified also in accordance with established procedures.

It is apparent to those skilled in the art that substitution of certain amino acids in these epitopes will not affect immunoreactivity toward the epitopes. For example, substitution of leucine by isoleucine or valine and all combinations thereof is unlikely to alter the sensitivity of an antibody raised against this epitope. Thus all epitopes capable of generating antibodies reactive to the epitopes listed above for the purpose of selectively identifying misfolded specific protein are aspects of this invention.

It is occasionally desirable to derivatize amino acids present in the epitopes to obtain a more robust immune response or more selective reactivity toward the misfolded form. For example, the SOD1-derived epitope FGDNTAGCTSA (SEQ ID No. 32) contains a cysteine that on misfolding of SOD1 may become oxidatively derivatized to cysteine sulfinic acid or cysteine sulfonic acid (cysteic acid). Thus antibodies against a free peptide containing, for example, a cysteic acid residue in place of cysteine are potentially more specific to the misfolded form of the protein. In general, candidate epitopes identified according to the methods described herein and containing derivatives of their constituent amino acids are an aspect of the present invention.

For epitopes containing proline, it may be desirable to prepare antigen peptides containing proline analogues that are fixed in the cis- or trans-configuration. Such analogues have been described previously (Scheraga et al, J Am Chem Soc 121 (49), 11558 (1999); Wang et al, J Org Chem 68 (6), 2343 (2002)). Unlike the other amino acids, for which there is a prohibitively large energy difference between the cis- and trans-amide bond stereoisomers, proline in unstructured peptides is able to interconvert between a cis- and trans-geometry on a relatively rapid time scale. When a proline is incorporated into the folded protein, steric interactions lock it into only one of the two possible conformers, but on unfolding it is free to racemerize. By raising antibodies against peptides incorporating a proline analogue with the opposite stereochemistry to that present in the native structure, the selectivity of the antibody for the unfolded state is much increased. Thus epitope peptides predicted by the method and incorporating cis- or trans-analogues of proline are an aspect of this invention.

Thus, it will be appreciated that the epitopes predicted by the method of the present invention, as exemplified in Table 1 above, will comprise at least 3 contiguous residues and up to 20 residues or more. The residues within the epitope may be represented as such in the parent protein, or may be a variation thereof in which 1, 2 or 3 residues have been substituted by a residue not found in the parent protein. The substituting amino acids may be conservative amino acid replacements, such as substitution of Leu by Ile or Val, or they may be chemically altered forms of the original amino acid, such as oxidized, nitrated or carboxylated forms, or particular enantiomeric alternatives.

With particular reference to Table 1, embodiments of the epitopes of the present invention thus include variations in which peptides longer than 7 residues are truncated by any number of residues effective to reduce the residue number to 7, peptides shorter than 7 residues are extended to include flanking residues present in the parent protein, and analogs in which 1, 2 or 3 residues have been substituted by another amino acid.

To identify epitopes that are useful in their truncated or extended form, e.g., relative to those peptides listed in Table 1, the epitope prediction methods can be applied or re-applied setting the stringency at a higher or lower level, thereby to relax or tighten the criteria applied when designating the peptide constituting a particular epitope.

Peptides comprising amino acid sequences that constitute epitopes can be useful per se to raise antibodies that bind specifically to them, provided they are endowed per se with the immunogenicity required to raise antibody in the selected antibody production host. For those epitopes that lack such immunogenicity, it is desirable to provide an immunogen that contains the epitope sequence. As used herein, "immunogen" refers to an immunogenic form of a peptide or other molecule that comprises the epitope, and is represented by the peptide itself when immunogenic per se, or is represented by the peptide in combination with an immunogenicity-enhancing agent. Any of the established agents can be used for this purpose. These agents typically include carrier proteins that can be coupled to the epitope either directly, such as through an amide bond, or indirectly through a chemical linker such as carbodiimide, a cysteine, or any peptide spacer sequence such as a glycine or glycine-serine sequence including Gly4-S. For example, an isolated peptide comprising a given epitope can be conjugated to MAP antigen, or keyhole limpet hemocyanin (KLH). Its large size makes it very immunogenic, and the large number of lysine residues available for conjugation make KLH very useful to attach to a polypeptide. The peptide corresponding to the epitope may further comprise a linker effective to couple the peptide tandemly to another copy of the same or a different peptide corresponding to the same or a different epitope. In another embodiment, the peptides may comprise additional amino acids that enhance the immunogenicity or solubility of the peptide. In one embodiment, the additional amino acids number from 1 to about 10, preferably 1 to 8, more preferably 1 to 5. Importantly the additional residues do not materially affect the conformation of the peptide.

Thus, epitopes that are not themselves immunogenic and do not constitute an immunogen can be rendered so, and provided as an immunogen, by incorporating immune enhancing agents that are either conjugated therewith or coupled covalently.

A composition comprising the immunogen can be prepared for purposes of producing antibodies in a selected host by combining the immunogen with an appropriate vehicle. Such vehicles include Freund's complete adjuvant or a suitable saline or phosphate buffered saline solution (0.05-1.0%).

Antibodies are then prepared to react against these epitopes when they are in an unstructured state. As noted, each peptide may be conjugated to a carrier protein like KLH to form an immunogen that is injected, optionally in combination with an adjuvant such as Freund's complete adjuvant, into a mammalian production host like a mouse, rat, rabbit, sheep or goat to provoke an immune response that generates antibodies against the peptide. Standard immunization protocols can be used, and the antibodies can be recovered from blood by enrichment against the immunizing agent, as exemplified herein.

The antibodies that bind selectively to the misfolding specific epitopes may be either polyclonal or monoclonal, of the IgG or IgM class, and may be derived from any mammal, particularly goats, rabbits or mice, or by recombinant methods. More generally, it will be appreciated that antibodies useful in the present invention include the various intact forms including polyclonal antibodies, monoclonal antibodies, and recombinant antibodies including chimeric antibodies, humanized antibodies as well as fully human antibodies. The chimeric antibodies comprise a portion of the heavy and/or light chain that is homologous with corresponding sequences in antibodies derived from a particular species, or belonging to a particular antibody class or subclass, while the remainder of the chain(s) is homologous with corresponding sequences derived from another species or belonging to a different antibody class. Humanized antibodies are chimeric antibodies that comprise minimal sequence derived from non-human antibody, usually incorporating CDRs from a non-human antibody into a human antibody framework, which may further be altered to incorporate non-human residues that restore and enhance antigen binding. The "fully" human antibodies can be produced in a non-human host using various techniques that are now established, including through the use of phage display libraries, and particularly by introducing human immunoglobulin loci into transgenic animals such as mice in which the endogenous immunoglobulin genes have been partially or completely inactivated. Upon challenge, human antibodies are produced which closely resemble that seen in humans in most respects, including gene rearrangement, assembly and antibody repertoire. The antibodies may be of any useful class, including IgA, IgD, IgE, IgG and IgM, and isotypes including IgG1, IgG2, IgG3, and IgG4. The constant region (Fc) of the antibodies can also be engineered or conjugated to provide altered effector function, thereby to enhance antibody dependent cell-mediated cytotoxicity (ADCC) and/or complement dependent cytotoxicity (CDC) activity.

In preferred embodiments, the antibody binds selectively to the sequence constituting the target epitope. Selective-binding agents are agents that bind the target epitope, and bind proteins that present the target epitope in a solvent-accessible orientation, with an affinity that is at least one order of magnitude greater (e.g., at least 2, 3, 4 or 5 orders of magnitude greater) than the affinity with which they bind a different, unrelated epitope. For instance, the binding affinity of an antibody that binds an EGFR on a cancer cell is preferably at least an order of magnitude greater than its binding affinity for the EGFR on normal tissue. Relative binding affinities can be determined, and the antibody so selected, on the basis of assays and techniques that generally are well established in the art for this purpose.

It will be appreciated that the antibody can, in some applications, be substituted by fragments thereof that also bind the target epitope, including Fab, Fab', F(ab')2, and Fv fragments, or by diabodies, linear antibodies, single chain antibody molecules, and multispecific antibodies formed from antibody fragments. Antibody fragments that incorporate the Fc region can also be engineered or conjugated to provide altered effector function, thereby to enhance ADCC and/or CDC activity.

It will also be appreciated that antibodies that bind selectively to the epitope unique to a misfolded form of a protein can be produced by techniques other than immunization, such as by the application of phage display and other systems that use high throughput to identify complementarity determining regions (CDR) or other sequences that bind to the target epitope. It is not essential that the resulting antibody has been first raised in vivo.

In embodiments, the antibody is one that binds selectively to a misfolded protein that presents an epitope set out in SEQ ID Nos. 1-4, 6, 8-26, 28-36, 41-75 and 77-80.

In use, the misfolding specific antibodies that bind to epitopes identified using the epitope prediction methods are potentially of great diagnostic and therapeutic use in protein misfolding diseases and cancer. In the case of protein misfolding diseases, including CJD, BSE, GSS, FFI, kuru, ALS, Alexander disease, familial amyloid polyneuropathy, senile systemic amyloidosis, and microglobin amyloidosis, misfolding-specific antibodies against their respective causative protein or proteins offer diagnosis of the disease by identification of the misfolded proteins in patient samples and minimally toxic treatment by selective inhibition of further misfolding and immune-targeted destruction of the misfolded protein complexes. In the case of cancers, including leukemias, myelomas, and adenocarcinomas, application of misfolding specific antibodies to tissue specimens will determine the presence or absence of misfolded protein selectively present on the surface of cancerous cells. Cancers that do express misfolded protein on their surface are then amenable to treatment by infusion of antibodies against the misfolded protein. As such, the present invention provides, as an article of manufacture, a diagnostic test and treatment procedure for protein misfolding diseases or cancers, by incorporating antibodies for recognition of misfolded proteins whose epitopes are identified by the epitope prediction methods.

More particularly, the present invention provides for the use of either the epitopes or the misfolding-specific antibodies raised from them for diagnostic use or for therapeutic use.

In therapeutic use, the epitopes or antibodies that bind selectively to them can be used to treat patients or subjects presenting with or at risk for a disease associated with the misfolded form of the protein to which the epitope is unique. The terms "treat", "treatment," "treating", "therapeutic use," or "treatment regimen" encompass prophylactic, palliative, and therapeutic modalities of administration of the compositions of the present invention, and include any and all uses of the present products that remedy a disease state, condition, symptom, sign, or disorder caused or associated with, either directly or indirectly, a misfolded form of a protein, including an inflammation-based pathology, infectious disease, allergic response, hyperimmune response, or other symptom to be treated, or which prevents, hinders, retards, or reverses the progression of symptoms, signs, conditions, or disorders associated therewith.

The term "subject" or "patient" generally refers to mammals and other animals including humans and other primates, companion animals, zoo, and farm animals, including, but not limited to, cats, dogs, rodents, rats, mice, hamsters, rabbits, horses, cows, sheep, pigs, elk or other ungulates, goats, poultry, etc. A subject includes one who is to be tested, or has been tested for prediction, assessment or diagnosis of a disease or disorder associated with a given misfolded protein target. The subject may have been previously assessed or diagnosed using other methods, such as those in current clinical practice, or may be selected as part of a general population (a control subject). A subject may be a transgenic animal, e.g. a rodent, such as a mouse, that produces a target protein especially in misfolded form, or is lacking expression thereof (e.g. a 'knock-out' mouse). For example, the subject may a transgenic mouse overexpressing a normal form of the target protein or may be a wild-type mouse or hamster that has been infected with a misfolded form of the target protein.

For treatment, the active ingredient, such as the immunogen used for active immunization and the antibody used for passive immunization are used in "effective amounts". These are amounts useful, in a treatment regimen, to reduce the effect of the endogenous, misfolded protein. It will be apparent that the present invention is applicable to a wide variety of diseases, and that the particular amount and treatment regimen effective to reduce the effect of the endogenous protein will vary with each disease, in accordance with established clinical practice for each disease.

In one embodiment, the present invention provides, for therapeutic use, a vaccine comprising any immunogenic form of an epitope that is unique to a misfolded form of a protein, to treat subjects presenting with disease that is associated with that misfolded form of the protein. For treatment, subjects are immunized on a schedule that can vary from once a day, to once a week, to once a month, to once a year, to once a decade. A typical regimen includes an immunization followed by booster injections at 6 weekly intervals. Another regimen consists of immunization followed by booster injections 1, 2 and 12 months later. Alternatively, booster injections will vary depending on the immune response and the physiological condition of the subject. For immunization, the epitope-containing immunogen can be administered in a dose that ranges from about 0.0001 microgram to 10 grams, about 0.01 microgram to about 1 gram, about 1 microgram to about 1 mg, and about 100 to 250 micrograms per treatment. In one embodiment the timing of administering treatment is at one or more of the following: 0 months, 2 months, 6 months, 9 months, and/or 12 months. In one regimen, the dosing is at 2, 6, 9, and 12 months following the first immunization. In another regimen, the dosing is at 2 and 4 weeks following the first immunization, and then monthly afterwards. In an alternative regimen, the dosing varies depending on the physiological condition of the subject and/or the response to the subject to prior immunizations. The route of administration optionally includes, but is not limited to, intramuscular and intraperitoneal injections. In one embodiment the composition is injected into the deltoid muscle.

The vaccine composition itself can further comprise adjuvants. Adjuvants for parenteral immunization include aluminum compounds (such as aluminum hydroxide, aluminum phosphate, and aluminum hydroxy phosphate). The antigen can be precipitated with, or adsorbed onto, the aluminum compound according to standard protocols. Other adjuvants such as RIBI (ImmunoChem, Hamilton, Mont.) can also be used in parenteral administration.

In embodiments of the present invention, vaccines useful in the treatment of disease include the following:

a) a vaccine that incorporates an immunogen comprising the epitope designated by SEQ ID No. 1, 2, 3, 4, 5, 6, 7, 8, 9 or 10, and particularly 3, 4, 6, 7, 8, 9 or 10, for the treatment of subjects afflicted with CJD or a related prion disease;

b) a vaccine that incorporates an immunogen comprising the epitope designated by SEQ ID No. 11, 12, 13, 14, or 15 for administration to subjects, particularly cattle, at risk for BSE or a related prion disease;

c) a vaccine that incorporates an immunogen comprising the epitope designated by SEQ ID No. 16, 17, 18, 19, 20, 21 or 22 for the treatment of subjects afflicted with familial amyloid polyneuropathy or senile systemic amyloidosis or a disease related by the presence of misfolded TTR;
d) a vaccine that incorporates an immunogen comprising the epitope designated by SEQ ID No. 23, 24, 25, or 26 for the treatment of subjects afflicted with renal accumulation of β2 microglobulin amyloid deposits or a disease related by the presence of misfolded β2 microglobulin;
e) a vaccine that incorporates an immunogen comprising the epitope designated by SEQ ID No. 27, 28, 29, 30, 31, 32, 33, 34, 35, 36, 37, 38, 39 or 40, and particularly by SEQ ID Nos. 28, 29, 31, 32, 33, 34, 35 and 36 for the treatment of subjects afflicted with amyotrophic lateral sclerosis (ALS) or a disease related by the presence of misfolded SOD1;
f) a vaccine that incorporates an immunogen comprising the epitope designated by SEQ ID No. 41, 42, 43, 44, or 45 for the treatment of subjects afflicted with leukemias or myelomas or a disease related by the presence of misfolded CD38;
g) a vaccine that incorporates an immunogen comprising the epitope designated by SEQ ID No. 46, 47, 48, 49, or 50 for the treatment of subjects afflicted with colon cancer metastasis and or a disease related by the presence of misfolded CD44;
h) a vaccine that incorporates an immunogen comprising the epitope designated by SEQ ID No. 51, 52, 53, 54, or 55 for the treatment of subjects afflicted with cancer in which Fas receptor is implicated;
i) a vaccine that incorporates an immunogen comprising the epitope designated by SEQ ID No. 56, 57, 58, 59, or 60 for the treatment of subjects afflicted with cancers including cervical, head and neck, endometrial, lung and breast carcinomas, pleural mesotheliomas, malignant melanomas, Hodgkin lymphomas, anaplastic large cell non-Hodgkin lymphomas, or a disease related by the presence of misfolded NOTCH1 including certain acute myeloid leukemias and B-cell chronic lymphoid leukemias;
j) a vaccine that incorporates an immunogen comprising the epitope designated by SEQ ID No. 61, 62, 63, 64, or 65 for the treatment of subjects afflicted with cancer in which Fas receptor activation is implicated; and
k) a vaccine that incorporates an immunogen comprising the epitope designated by SEQ ID No. 66, 67, 68, 69, 70, 71, 72, 73, 74, 75, 76, 77, 78, 79 or 80, with the optional proviso that SEQ ID No. 76 is excluded, for the treatment of subjects afflicted with certain cancers and related disorders in which misfolded EGFR is implicated.

It will be appreciated that the vaccines noted above may comprise, instead of the epitope designated above, a variant thereof that incorporates 1, 2 or 3, amino acid additions, substitutions or deletions. Particularly the epitope may be a variant that has been truncated or extended to consist of 6, 7, or 8 amino acids, preferably 7 amino acids, and that incorporates up to 2, usually 1, amino acid substitution, for instance in which an amino acid is replaced by an oxidized form thereof, or an enantiomeric alternative thereof.

In addition to such vaccines, the present invention provides for the therapeutic use of antibodies in the treatment of subjects presenting with the conditions noted above, including conditions/diseases related by the presence of the given misfolded protein. For treatment, antibody that binds selectively to the target epitope is administered as a pharmaceutical composition, comprising the antibody and a pharmaceutically acceptable carrier, in dosage form.

The dosage form is optionally a liquid dosage form. Antibody solutions can be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. Conventional procedures and ingredients for the selection and preparation of suitable formulations are described, for example, in Remington's Pharmaceutical Sciences (2003-20th edition) and in The United States Pharmacopeia: The National Formulary (USP 24 NF19) published in 1999.

Formulations optionally contain excipients including, but not limited to, a buffering agents, an anti-oxidant, a stabilizer, a carrier, a diluent, and an agent for pH adjustment. The pharmaceutical forms suitable for injectable use include sterile aqueous solutions or dispersion and sterile powders for the extemporaneous preparation of sterile injectable solutions or dispersions.

In treatment, the dose of antibody optionally ranges from about 0.0001 mg/kg to about 100 mg/kg, about 0.01 mg/kg to about 5 mg/kg, about 0.15 mg/kg to about 3 mg/kg, 0.5 mg/kg to about 2 mg/kg and about 1 mg/kg to about 2 mg/kg of the subject's body weight. In other embodiments the dose ranges from about 100 mg/kg to about 5 g/kg, about 500 mg/kg to about 2 mg/kg and about 750 mg/kg to about 1.5 g/kg of the subject's body weight.

Therapeutic use of an antibody according to the present invention entails antibody administration, by injection or infusion, to subjects presenting with a disease in which cells or fluids present the epitope targeted by the antibody, i.e., in which the misfolded target protein is present. Subjects that would benefit from treatment can be identified by their clinical features, together with examination of tissue samples or bodily fluids to identify cells that present the epitope targeted by the antibody, as discussed infra.

In embodiments of the present invention, antibody compositions useful in the treatment of disease include compositions that incorporate the following:
a) an antibody that binds selectively to the epitope designated by SEQ ID No. 1, 2, 3, 4, 5, 6, 7, 8, 9 or 10, and particularly 3, 4, 6, 7, 8, 9 or 10, for the treatment of subjects afflicted with CJD or a related prion disease;
b) a an antibody that binds selectively to the epitope designated by SEQ ID No. 16, 17, 18, 19, 20, 21 or 22 for the treatment of subjects afflicted with familial amyloid polyneuropathy or senile systemic amyloidosis or a disease related by the presence of misfolded TTR;
c) an antibody that binds selectively to the epitope designated by SEQ ID No. 23, 24, 25, or 26 for the treatment of subjects afflicted with renal accumulation of β2 microglobulin amyloid deposits or a disease related by the presence of misfolded β2 microglobulin;
d) an antibody that binds selectively to the epitope designated by SEQ ID No. 27, 28, 29, 30, 31, 32, 33, 34, 35, 36, 37, 38, 39 or 40 and particularly by SEQ ID Nos. 28, 29, 31, 32, 33, 34, 35 and 36 for the treatment of subjects afflicted with amyotrophic lateral sclerosis (ALS) or a disease related by the presence of misfolded SOD1;
e) an antibody that binds selectively to the epitope designated by SEQ ID No. 41, 42, 43, 44, or 45 for the treatment of subjects afflicted with leukemias or myelomas or a disease related by the presence of misfolded CD38;
f) an antibody that binds selectively to the epitope designated by SEQ ID No. 46, 47, 48, 49, or 50 for the treatment of subjects afflicted with colon cancer metastasis and or a disease related by the presence of misfolded CD44;

g) an antibody that binds selectively to the epitope designated by SEQ ID No. 51, 52, 53, 54, or 55 for the treatment of subjects afflicted with cancer in which Fas receptor activation is implicated;

h) an antibody that binds selectively to the epitope designated by SEQ ID No. 56, 57, 58, 59, or 60 for the treatment of subjects afflicted with cancers including cervical, head and neck, endometrial, lung and breast carcinomas, pleural mesotheliomas, malignant melanomas, Hodgkin lymphomas, anaplastic large cell non-Hodgkin lymphomas, or a disease related by the presence of misfolded NOTCH1 including certain acute myeloid leukemias and B-cell chronic lymphoid leukemias;

i) an antibody that binds selectively to the epitope designated by SEQ ID No. 61, 62, 63, 64, or 65 for the treatment of subjects afflicted with cancer in which misfolded Fas receptor could be targeted; and j) an antibody that binds selectively to the epitope designated by SEQ ID No. 66, 67, 68, 69, 70, 71, 72, 73, 74, 75, 76, 77, 78, 79 or 80, with the optional proviso that SEQ ID No. 76 is excluded, for the treatment of subjects afflicted with certain cancers and related disorders in which misfolded EGFR is implicated.

It will be appreciated that the antibody compositions noted above may comprise, as the antibody, an antibody that is polyclonal, monoclonal, recombinant, chimeric, human or humanized and that desirably comprises an active effector function conferred by an intact Fc region or a functionally equivalent variant thereof.

To assist with the identification of subjects who are candidates for treatment with the antibody or vaccine compositions of the invention, the present invention further provides for the detection of an epitope by in vitro or in vivo diagnostic methods.

To detect the presence of a misfolded protein in any given sample, the present invention provides a detection method in which a sample suspected to contain the misfolded protein is treated with an antibody or binding fragment that binds selectively to an epitope presented uniquely by the misfolded protein relative to the natively folded form of that protein; and determining whether an antigen:antibody complex has formed, the formation thereof being indicative of the presence in the sample of a misfolded form of said protein. In one embodiment, the epitope is one that has been identified by applying the present epitope prediction method. In another embodiment, the epitope is one that is, or is comprised within, a peptide having any one of SEQ ID Nos. 1-80. In a further embodiment, the antibody is one that binds selectively to a peptide having any one of SEQ ID Nos. 1-80 with the proviso that the peptide is not SEQ ID No. 1, 5, 7, 27, 30, 37-40 or 76.

When applied in vitro, the detection method entails analysis of a sample of body fluid or tissue or organ sample from a subject, usually a subject suspected of having endogenous misfolded target protein. For example, the biological sample may a body fluid such as cerebrospinal fluid, blood, plasma, lymph fluid, serum, urine or saliva. A tissue or organ sample, such as that obtained from a solid or semi-solid tissue or organ, may be digested, extracted or otherwise rendered to a liquid form—examples of such tissues or organs include cultured cells, blood cells, brain, neurological tissue, skin, liver, heart, kidney, pancreas, islets of Langerhans, bone marrow, blood, blood vessels, heart valve, lung, intestine, bowel, spleen, bladder, penis, face, hand, bone, muscle, fat, cornea or the like, including cancerous forms thereof. A biological sample or samples may be taken from a subject at any appropriate time, including before the subject is diagnosed with, or suspected of having a protein misfolding associated disease or disorder, during a therapeutic regimen for the treatment or amelioration of symptoms of that disease or disorder, after death of the subject (regardless of the cause, or suspected cause). Alternately, a biological sample may include donated body fluid or tissue, such as blood, plasma or platelets when in care of a centralized blood supply organization or institution. Alternately, a biological sample may include meat, blood or tissue from a food animal, for example taken at the time of slaughter in an abattoir.

The presence of misfolded target protein in the sample is confirmed if the antibody forms a detectable antigen:antibody complex. The formation of such complex can be determined using a wide variety of protocols that include ELISA, RIA, flow cytometry, Western blots, immunohistochemistry and the like. To reveal the complex and hence the presence of the epitope in the sample, the antibody desirably is provided as a labeled antibody by conjugation or coupling to an agent that is detectable either visually or with the aid of instrumentation. The agent, or label, is capable of producing, either directly or indirectly, a detectable signal. For example, the label may be radio-opaque or a radioisotope, such as $^{3}H$, $^{14}C$, $^{32}P$, $^{35}S$, $^{123}I$, $^{125}I$, $^{131}I$; a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion. Alternatively, the epitope can be revealed using a labeled secondary reagent that binds to the epitope antibody, such as a labeled antibody that binds the epitope antibody, to reveal presence of the epitope indirectly. The presence of an antibody:antigen complex may be detected by indirect means that do not require the two agents to be in solution. For instance, the complex is detectable indirectly using flow cytometry, where the antibody binds to, and forms an antibody:antigen complex with, the epitope presented on the surface of an intact cell. The application of the antibodies for detection of cell-surface forms of the epitope is a very useful embodiment of the invention particularly for detection of cancer cells presenting such epitopes. Detection of such cells including cancer cells can be achieved using the well established technique of flow cytometry. It will also be appreciated that the antigen:antibody complex can also be identified by non-antibody based methods, that include those which sort proteins based on size, charge and mobility, such as electrophoresis, chromatography, mass spectroscopy and the like.

In a related embodiment, the labeled antibodies of the invention, or labeled form of a binding fragment thereof, can be used in vivo to image the presence of the misfolded protein to which the antibody binds. To this end, the present invention provides an antibody or fragment in a form coupled to an agent useful for in vivo imaging, such as isotopes of technetium, gadolinium, and the like.

The invention also includes articles of manufacture as well as kits that comprise components useful to perform the diagnostic and therapeutic methods of the present invention. The articles of manufacture comprise packaging material and a composition comprising an antibody or antisera that binds selectively to an epitope unique to a misfolded form of protein, relative to the natively folded form of that protein. The composition includes a physiologically or pharmaceutically acceptable excipient, and the packaging material may include a label which indicates the active ingredients of the composition (e.g. the antisera or antibody). The label may further include an intended use of the composition, for example as a diagnostic reagent to be used with kits as set out herein.

Also provided is an article of manufacture, comprising packaging material and a composition comprising a peptide, or one or more peptides, as provided herein. The composition may include a physiologically or pharmaceutically acceptable excipient, and the packaging material may include a label which indicates the active ingredients of the composition (e.g. the peptide). The label may further include an intended use of the composition, for example as a therapeutic or prophylactic reagent, or as a composition to induce an immune response in a subject for the purpose of producing antisera or antibodies specific to mammalian PrP$^{Sc}$, to be used with kits as set out herein.

In a further embodiment, there is provided a kit comprising a composition comprising one or more peptides as provided herein, along with instructions for use of the compound or composition for the production or screening of antibodies for identification of a misfolded protein. The kit may be useful for production and/or identification of PrP$^{Sc}$ specific antibodies or antisera, and the instructions may include, for example, dose concentrations, dose intervals, preferred administration methods, methods for immunological screening or testing, or the like.

In another embodiment, a kit for the preparation of a medicament, comprising a composition comprising one or more peptides as provided herein, along with instructions for its use is provided. The instructions may comprise a series of steps for the preparation of the medicament, the medicament being useful for inducing a therapeutic or prophylactic immune response in a subject to whom it is administered. The kit may further comprise instructions for use of the medicament in treatment for treatment, prevention or amelioration of one or more symptoms of a disease or disorder associated with protein misfolding, or in which protein misfolding is implicated, and include, for example, dose concentrations, dose intervals, preferred administration methods or the like.

In another embodiment, a kit for diagnosing a disease or disorder associated with protein misfolding is provided. The kit comprises one or more misfolded protein-selective antibodies or antisera as described herein, along with instructions for its use. The antibody may further be coupled to a detection reagent. Examples of detection reagents include secondary antibodies, such as an anti-mouse antibody, an anti-rabbit antibody or the like. Such secondary antibodies may be coupled with an enzyme that, when provided with a suitable substrate, provides a detectable colorimetric or chemiluminescent reaction. The kit may further comprise reagents for performing the detection reaction, including enzymes such as proteinase K, blocking buffers, homogenization buffers, extraction buffers, dilution buffers or the like.

In another embodiment, a kit for detecting the presence of misfolded protein in a biological sample is provided. The kit comprises one or more antibodies or antisera that specifically bind the misfolded protein, along with instructions for its use. The antibody may further be coupled to a detection reagent. Examples of detection reagents include secondary antibodies, such as an anti-mouse antibody, an anti-rabbit antibody or the like. Such secondary antibodies may be coupled with an enzyme that, when provided with a suitable substrate, provides a detectable colorimetric or chemiluminescent reaction. The kit may further comprise reagents for performing the detection reaction, including enzymes such as proteinase K, blocking buffers, homogenization buffers, extraction buffers, dilution buffers or the like.

Example 1—hSOD1

As described in WO2007/098607, Cashman et al teach the production of an hSOD1 antibody that was raised against the 35-45 region of hSOD1, a region essentially predicted by the present epitope prediction methods as constituting an hSOD1 epitope with a propensity for unfolding. The predicted sequence of 35-41 is essentially a truncated version of the 35-45 region targeted by the published antibody. The antibody production and testing work published in that patent application is reproduced below.

For antibody production, 4 female BALB/c mice were initially immunized by intraperitoneal injections with 25 μg of immunogen comprising peptide C-IKGLTEGLHGF (SEQ ID NO:89, corresponding to hSOD1 residues 35-45) coupled to KLH by disulfide formation with a cysteine that was added to the N terminus, in Complete Freund's Adjuvant. Four subsequent boosts were administered as above, spaced at 3 week intervals, with Incomplete Freund's Adjuvant. When the serum titre had risen more than 10-fold from a preimmune serum sample, as determined by ELISA, the 2 highest responders were each boosted intravenously with 10 μg of protein antigen, in 100 μl of sterile PBS pH 7.4. Three days later the donor mice were sacrificed and the spleen cells were harvested and pooled. Fusion of the splenocytes with SP2/0 BALB/c parental myeloma cells was performed as previously described as in example one above except that one-step selection and cloning of the hybridomas was performed in Clone EZ medium. This semi-solid medium allows HAT selection and cloning in a single step and eliminates the overgrowth of slower growing desirable clones by faster growing, perhaps undesirable, hybridomas. Clones were picked 11 days post fusion and resuspended in wells of 96-well tissue culture plates in: 200 μl of D-MEM (Invitrogen) medium containing 20% fetal bovine serum. After 4 days, the supernatants were screened by indirect ELISA for antibody activity on plates coated with 1 μg/well of protein antigen.

ELISA Conditions:

For Screening and Testing:

HSOD1-BSA antigen was coated onto plate in $dH_2O$ at 1 μg/well and dried down overnight at 37° C.

For testing on negative control antigen: 0.5 μg/well HT (human transferrin) antigen coated onto plate in $dH_2O$ at 50 μL/well and dried down overnight at 37° C.

Blocking:

Plates were blocked with 3% skim milk powder in PBS (pH 7.4) at 100 μL/well and incubated for 1 hour at room temperature.

1° Antibody:

Mouse anti-HSOD1 hybridoma tissue culture supernatant and mouse monoclonal controls were added at 100 μL neat per well for screening and testing. Mouse anti-DSE-1a immune serum and mouse pre-immune serum diluted 1/800 in SP2/0 tissue culture supernatant were added at 100 μL/well and incubated for 1 hour at room temperature with shaking.

2° Antibody Used for Screening and Testing:

1/10000 Goat anti-mouse IgG Fc HRP conjugated was used. Secondary antibody was diluted in PBS-Tween (pH 7.4), added at 100 μL/well and incubated for 1 hour at 37° C. with shaking.

Substrate:

TMB buffer (BioFx cat#TMBW-1000-01) was added at 50 μL per well and incubated in the dark at room temperature. The reaction stopped with 504 μL 1M HCl per well after 15 minutes and read at $OD_{450}$ nm.

Table 2 shows the ELISA screening of hybridoma clones for antibodies directed against hSOD1 epitope (IKGLTEGL-HGF, SEQ ID NO:_89), an extension of epitope IKGLTEG of SEQ ID No. 30. The antibodies generated by several of the hybridoma clones were highly specific for the peptide corresponding to the epitope, and did not detectably recognize the control antigen HT (human transferrin). These results show that monoclonal antibodies can be produced against peptides corresponding to epitopes identified as selectively presented or accessible on misfolded forms of SOD1.

TABLE 2

ELISA screening of hybridoma clones for antibodies directed against epitope hSOD1 residues IKGLTEGLHGF (35-45)

| Clone | Exp #1 DSE-5-BSA Antigen | Exp #2 DSE-5-BSA Antigen | HT Antigen | Isotype |
|---|---|---|---|---|
| 5C6 | 2.779 | 1.787 | 0.079 | IgG |

Example 2—EGFR

As noted in Table 1 herein, application of the epitope prediction methods to the structure of human epidermal growth factor receptor (hEGFR) indicates that an epitope with propensity for unfolding resides at residues 288-301, having the peptide sequence GADSYEMEEDGVRK (SEQ ID No.76). The EGFR itself is a protein targeted for therapeutic intervention by a variety of antibodies that are either marketed (cetuximab as Erbitux®, panitumumab as Vectibix®) or in clinical development (nimotuzumab). These antibodies have efficacy in the treatment of various solid tumours, including head and neck as well as pediatric glioma. With the exception of nimotuzumab, the antibodies targeting EGFR raise significant toxicities associated particularly with their interaction with keratinocytes—while improvements can be shown in the stasis or regression of tumour growth, recipients show a variety of skin disorders including severe rash. This results from the antibody's non-selective binding not only to the EGFR presented by the cancer cells, but also by the skin and other cells. Application of the epitope prediction methods to identify epitopes unique to cancer cells relative to other cells can be very useful for development of EGFR-targeting drugs that are selective for disease cells.

The ability of the epitope prediction methods to predict targets useful to bind EGFR in its misfolded state is demonstrated by the raising of antibodies to a peptide having substantially the same sequence as the 288-301 peptide noted above. In particular, Garrett et al (PNAS, 2009, 106(13):5082-5087 incorporated herein by reference) describe the production and testing of an antibody that binds a short cysteine loop within the extracellular domain of EGFR, comprising residues 287-302. In other words, this antibody (mAb806, an IgG2b) binds to the epitope prediction methods-predicted, 288-301 region of EGFR. As shown by Garrett et al, mAb806 displays negligible binding to normal cells and substantially higher levels of binding to tumour cells that have overexpressed and/or activated EGFR. Moreover, the studies of Garrett et al demonstrate the tumoricidal effect of the antibody when tested against the prostate cell line DU145. It will thus be appreciated that the epitope prediction method of the present invention is useful to identify epitopes that can usefully be targeted for therapeutic purposes.

Example 3—Additional EGFR Epitopes

Rabbits were immunized with EGFR peptides predicted by the epitope prediction methods to have a propensity for unfolding to present unique epitopes (see Table 1). For convenience, rabbit E1 was immunized with 8 peptides, i.e., peptides having SEQ ID Nos. 67, 69, 70, 72, 73, 75, and 78. Rabbit E2 was immunized with 7 peptides, i.e., peptides having SEQ ID Nos. 66, 71, 74, 76, 77, 79 and 80.

Antisera from these rabbits were tested for their ability to bind to one normal cell (HUVEC) and 14 tumor cells. Preimmune rabbit serum was used as a binding control. Each cell was also evaluated for its level of EGFR expression using a commercially available anti-EGFR antibody compared to an isotype control antibody.

On analysis of the results, it was observed that the normal cells (HUVEC) express low levels of EGFR and do not bind antisera from rabbit E1 or E2. Two of the tumors tested (human GI stromal colon tumour LTL-257, and human cervical carcinoma cell line SiHa) express EGFR, but do not bind to either antisera from rabbits E1 or E2. Three of the tumors tested (mouse neuroblastoma cell line NSc34, mouse melanoma cell line B16 and human myeloid line HL60) do not express EGFR and do not bind to either antisera from rabbits E1 or E2. Six of the tumors tested (human prostate tumour LTL-220a, human lung cancer LTL-657, human colon adenocarcinoma LTL-289, human melanoma LTL-323, human pancreatic LTL-249 and human lung cancer LTL-618) express EGFR and bind to antisera from both rabbits E1 and E2. Three of the tumors tested (a human oligodendroglial cell line Mo3.13, human ovarian cancer LTL-321 and human lymphoma LTL-013) express EGFR and bind to antisera from rabbit E2, but not rabbit E1.

These data indicate that EGFR is misfolded at the cell surface of selected human and mouse tumor cells, but not on normal cells (HUVEC). Differences in immunoreactivity of tumors with the two immunized rabbit sera tested suggest that particular patterns of EGFR misfolding may be present at the cell surface of different tumors; these differences can be confirmed and characterized with monoclonal antibodies derived from the immunized rabbits. Monoclonal antibodies thus derived can be utilized as diagnostic reagents for particular tumor types, and humanized for passive immunotherapies of the applicable tumor.

Example 4—Human PrP—YYR

The epitope prediction method has predicted that epitopes uniquely exposed on misfolded, but not natively structured, $PrP^C$ reside in the peptides RYYRENMH and QVYYRPV (SEQ ID Nos 5 and 7 respectively). Resident within each of these peptides is the 3-amino acid epitope designated YYR noted above. Antibodies against the YYR epitope of PrP are described in the literature by Cashman (see U.S. Pat. No. 7,041,807 incorporated herein by reference). That work is reproduced below. As noted in the results, the antibodies to YYR bind selectively to the disease-misfolded form of $PrP^C$, and do not bind to the natively folded form.

In order to develop an antibody to the YYR epitope presented by misfolded $PrP^C$ and but not by natively folded $PrP^C$, a peptide with the amino acid sequence Acetyl-Cys-Tyr-Tyr-Arg-NH2 (YYR) was synthesized, conjugated to KLH, and injected intramuscularly into rabbits using well known techniques. At the amino-terminus of the peptide, a cysteine residue was added to allow conjugation of the peptide with the protein carrier. The amino group of the peptide was blocked by acetylation, and the carboxylic group of the peptide was blocked by amidation.

Peptides were synthesized using solid phase peptide synthesis methods either manually or automated (MPS396 peptides synthesizer, Advanced ChemTech). Coupling of amino acid residues was accomplished using Fmoc peptide synthesis chemistry (Fields et al., 1990, IJPPR 35, 161). Syntheses were performed on Wang or on amide Rink resins, with full side chain protection of amino acids. Since the alpha-NH2 groups of the amino acids were protected with the Fmoc group, the following protective groups were chosen for the side groups of the trifunctional amino acids:
Cysteine: 5-triphenylmethyl (Trt)
Arginine: 2,2,4,6,7-pentamethyldihydrobenzofuran-5 sulfonyl (Pbf)
Tyrosine: tert.-butyl ether (tBu)\
BOP, PyBOP, or TBTU were used as activation agents, depending on the chemistry and difficulty of the coupling reaction. All chemicals were purchased from Advanced Chem Tech, Bachem, and Calbiochem/NovaBiochem. Formation of each peptide bond between residues of the sequence was ensured by using a 3 to 6 fold excess of coupling reagents and by so-called double coupling; meaning that the coupling reaction was repeated for each amino acid added to the growing peptide chain.

After synthesis, the peptides were cleaved from the resin using the Reagent K as a cleavage mixture: water (2.5%), TIS (2.5%), EDT (2.5%), TFA (92.5%).

The peptides were then precipitated with cold diethyl ether. The precipitates were centrifuged, washed three times with diethyl ether, dissolved in 20%-50% AcCN/water mixture, and lyophilized. Analysis of crude products was performed using analytical RP-HPLC and electrospray MS.

The crude peptide was purified by Rp-HPLC (reverse phase high performance liquid chromatography) on a Vydac C18 column, 2.5×25 cm, using a linear gradient of 10-50% acetonitrile in water, with 0.06% TFA (1%/min gradient, 10 ml/min flow rate), with monitoring by UV at 215 nm and 254 nm. Analytical HPLC was used to estimate the purity of the fractions. The final product was obtained as a lyophilized peptide with at least 95% purity estimated by analytical HPLC (Vydac C18, 0.46×25 cm, linear gradient 10-60% acetonitrile in water, 0.1% TFA, 1%/min, 1 mL/minflow rate, detection by UV absorption at 215 nm and 254 nm). The pure peptide was identified by molecular mass analysis using a SCIEX API III mass spectrometer according to standard procedures.

The retention time of the peptide on RP-HPLC was 21.215 minutes. The theoretical molecular weight of the peptide was calculated to be 644.74; the actual molecular weight, through molecular mass analysis, was found to be 646.5 (MW+H*).

Peptides were coupled to a carrier, in this case Keyhole limpet hemocyanin (KLH). Other carriers useful for such coupling include, without limitation, albumin, or ovalbumin, 8map, or lysozyme. Coupling was effected via a thioether linkage to the mercapto group of the cysteine. This type of linkage has the advantage that the peptide is coupled in a defined way to a carrier protein.

Coupling to KLH was performed as follows. 10 mg of the peptide was dissolved in 2 ml of phosphate buffered solution (PBS 1×). 1 ml of KLH (pierce products #77100) was added to the peptide solution and stirred (1 mole of peptide/50 amino acids). The KLH concentration was 10 mg/ml. 20 ul of glutaraldehyde (25% aqueous solution) was added to the peptide/carrier solution with constant stirring, incubated for 1 hour, after which a glycine stop solution was added. The peptide/carrier conjugate was separated from the peptide by dialysis against PBS Additional YYR peptides (eg., CYYRRYYRYY and CKYEDRYYRE; SEQ ID NOs:_90 and 91) can be synthesized according to standard methods, for example, those described herein. Other synthetic peptides can be prepared by making appropriate modifications of the above described synthetic methods. Such peptides are also characterized using any of the standard methods known in the art (e.g. those described herein).

Polyclonal antibodies were prepared according to standard methods, and an immune response was enhanced with repeated booster injections, at intervals of 3 to 8 weeks. The success of the immunization was verified by determining the concentration of antibodies in a western blot or ELISA or both. More specifically, to generate polyclonal antibodies to misfolded $PrP^C$ (or $PrP^{Sc}$), the tripeptide YYR conjugated to KLH was injected into rabbits in accordance with a 164 day immunization regimen, after which the animals that had produced specific antibodies were bled.

In order to sample the serum prior to immunization, 10 ml of blood per rabbit was taken as a preimmune control. Primary immunizations were carried out with Freund's complete adjuvant and subsequent boosts with incomplete Freund's adjuvant (IFA0 (1 ml per rabbit, 0.5 ml per thigh muscle). Each injection consisted of approximately 200 ug of the purified peptide. At days 21, 42 and 70, a booster injection was given with IFA. At days 31, 42 and 80, 10 ml of blood was collected from the central ear artery for titer determination (6 ml/kg/rabbit). At day 80, the titer of the sera was checked, and 3 more injections were given (IFA) at 4 week intervals, followed by blood sampling 10 days later. 10 days after the last boost, anesthetized rabbits were exsanguinated via cardiac puncture, and antisera were collected.

Goat polyclonal antibodies were generated according to standard methods. Three goats were immunized as follows. On day 1, all the goats received a primary immunization of 1 mg of YYR-KLH conjugates in complete Freund's adjuvant. Boosts were done by injection of 1 mg YYR-KLH in incomplete Freund's adjuvant for two of the three goats, whereas the third goat received 1 mg YYR-8map conjugates in incomplete Freund's adjuvant. Serum samples from each of the three bleeds were tested for reactivity by ELISA against YYR-BSA conjugates. From the third set of bleeds, total IgG was purified by ammonium sulfate precipitation and YYR-reactive IgG was purified using a YYR affinity column. IgG fractions were tested for reactivity to PrPSc as described herein. The exact immunization schedule was as follows: Day 1, primary immunization; D 21, first boost immunization; Day 30, first bleed; Day 46, second boost immunization; Day 53, second boost immunization; Day 60, second bleed; Day 76, third boost immunization; Day 83, third boost immunization; and Day 90, third bleed.

Alternatively, monoclonal antibodies may be prepared using the synthetic peptides described herein and standard hybridoma technology (see, e.g., Kohler et al., Nature 256, 1975; Kohler et al., Eur. J. Immunol. 6:511, 1976; Kohler et al., Eur. J. Immunol. 6:292, 1976 Hammerling et al., In Monoclonal Antibodies and T Cell Hydridomas, Elsevier, N Y, 1981; Ausubel et al., 1999, Current Protocols in Molecular Biology, Wiley Interscience, New York,) Once produced, monoclonal antibodies are also tested for specific PrP recognition by immunoprecipitation and western blot analysis.

The generation of monoclonal antibodies was carried out as follows. Mice were immunized with baculovirus supernatant containing mouse PrP-AP fusion protein in complete Freund's adjuvant, then boosted 2 weeks later with the same antigen in incomplete Freund's adjuvant. Two weeks after that immunization the mice were boosted with a mixture of PrP-AP supernatant plus 100 ug of KLH-CYYRRYYRYY (SEQ ID NO:_90_ and 10 ug of KLH-CKYEDRYYRE (SEQ ID NO:_91) conjugates. Splenocytes from these mice were fused to the FO murine B cell line (ATCC CRL-1646) to generate specific hybridoma clones. Hybridoma supernatants were screened by ELISA. There were no reactive supernatants to PrP-AP or to the CKYEDRYYRE (SEQ ID NO:_91) sequence, although there were clones reactive to YYR-8map conjugates.

Total rabbit IgG was purified from serum using the Pharmacia protein A HiTrap column according to the manufacturer's recommendations. Briefly, a HiTrap column was equilibrated with 3 column volumes of start buffer (0.2M sodium phosphate buffer, pH7.0). Serum was applied, using a syringe through a luer adaptor, onto the column. The column was subsequently washed with 5 ml of start buffer. Bound protein was eluted with 0.1 M glycine, pH 3.0, and collected in eppendorf tubes containing 1M Tris ph 8.0 (50 ul/500 ul sample). Fractions were analyzed on SDA-PAGE.

Goat polyclonal antibodies were purified from serum samples as is described above.

Mouse monoclonal antibodies were produced as ascites, and purified using a protein A column kit (Pierce) according to the manufacturer's instructions. Briefly, a sample of ascites was diluted with binding buffer at a 1:1 final ratio. The sample was then added to the top of the column, which had been previously equilibrated with binding buffer, and allowed to flow through the matrix. The pass-through material was collected and the column washed with 5 volumes of binding buffer. Mild elution buffer was added to the column to release the bound IgG antibody from the matrix. Other antibody isotypes were collected by switching to the IgG elution buffer. All the antibodies were collected in 1 ml fractions, which were analyzed by BCA to determine total protein content and SDS-PAGE electrophoresis to establish the degree of antibody purity. The fraction containing the most yield of IgG was desalted by passing it through a D-salt column (Pierce). The antibody fraction was allocated and stored at −80 C. in PBS Antibodies produced using the aforementioned procedures were subsequently tested for high-affinity binding as follows.

Ten ul of brain extract was added to 950 ul of Immunoprecipitation buffer (PBS 3% NP-40, 3% Tween-20) and incubated at 37 C. for 30 or 60 minutes. For experiments evaluating the reactivity of PrP 27-30 with the bead conjugates, the incubation was preceded by addition of 50 ul of 1 mg/ml proteinase K. Samples not treated with proteinase K were still incubated at 37 D. for the appropriate time period. After the incubation, 60 ul of an 100 mM PMSF solution were added to both sets of tubes. On hundred ul of resuspended bead conjugates were then added to the mixture, and incubated with rotation at room temperature for 2 hours. The beads were washed 3 times with washing buffer (PBS 2% NP-40 2% Tween-20) and resuspended by vortex after each wash. After the last wash, the beads were resuspended in 20 ul of 2× loading buffer (100 mM Tris pH 6.8, 4% SDS, 0.015% bromphenol blue, 20% glycerol) and heated at 95 C. for 3 minutes.

The PrP$^{Sc}$ content of brain homogenates was determined by western blotting according to standard methods. Protein samples were mixed with 2× sample buffer at a ratio of 1:1 and boiled for 5 minutes at 100 C. SDS-PAGE analysis was performed according to standard methods. Samples were applied to a pre cast 15% acrylamide gels (Biorad) along with pre-stained molecular weight markers (Biorad). The gels were run at 100 V until the bromophenol blue dye front reached the bottom of the gel. The separated protein was then transferred onto PVDF membranes at 100 V or 1 hr. The membranes were washed as described above before incubation with a goat anti-mouse IgG alkaline phosphatase conjugated secondary antibody (1:5000 in TBST) for 1 hour at room temperature. After washing, signals were developed with the chemiluminescent substrate CDP-star, and exposed to x-ray films.

Spleen cell suspensions were prepared from Balb/c mice by passing the tissues through a wire mesh. The cells were washed once with cold Dulbecco's PBS without Ca2+ or Mg2+ and viable cells were isolated by underlayering of the cell suspension with Lympholyte (Cedarlane) and centrifugation at 1300 g for 20 minutes. The cells were washed once with cold Dulbecco's PBS without CA2+ or Mg2+2.5% fetal bovine serum, and $0.5 \times 10^6$ cells were aliquoted per well in a round bottom 96 well plate. The cells were centrifuged and resuspended in 50 ul of antibody-FITC conjugates at 1/10 final concentration in Dulbecco's PBS without CA2+ or Mg2+2.5% fetal bovine serum, for 15 minutes on ice. The cells were then washed twice with cold Dulbecco's PBS without Ca2+ or Mg2+2.5% fetal bovine serum and resuspended in the same medium containing 1 ug/ml of propidium iodide. The cells were analyzed on a Coulter Epics flow cytometer and were gated by size and granularity (forward and side scatter) and viability (exclusion of propidium iodide fluorescence).

Fluoresceinated mAbs were made by using the Fluorotag kit (Sigma) following the manufacturer's instructions. Briefly, 0.5 mg of each antibody was raised to pH 9 with concentrated bicarbonate buffer, and FITC stock solution was added to produce an FITC: antibody ratio of 20:1. The vials were then incubated for 2 hours at room temperature. Labeled antibody was separated from free FITC by passing the mixture over a Sephadex G-25M column. Conjugated antibodies were tested for successful fluoresceination by measuring their FITC emissions at 35 nm using an LJL Biosystems Analyst, and the antibodies were tested for retention of their binding activity with an ELISA against YYR-8map conjugates.

To determine whether antibody pAbC2 was useful in specifically recognizing PrP$^{Sc}$ from bovine brain extracts, compared to PrPC using recombinant PrP (rbPrP), an ELISA approach was used. Either pools of PrPSc containing brain extracts or rbPrP was used to test the specificity of pAbC2 for PrPSc. The wells of an Immunolon ELISA plate (Dynex) were coated overnight at 4 C. with the PC2 containing culture supernatant in a TBS buffer containing 50 mM Tris, pH 7.5, 150 mM NaCl, 1 mM CaCl2. For BSE-brain extract experiments, control wells were coated with a supernatant containing Mek-4; for rbPrP experiments, milk was used as a control to determine the nonspecific binding of the antibody to the well. The coating fo the ELISA plates with soluble PC2 was confirmed with an anti-PC2 monoclonal antibody. The wells were washed four times using a SLT 'Columbus' microplate washer (Tecan) with TBS containing 0.05% Tween 20, and blocked by filling the wells with 0.2% I-Block (Tropix) in TBST and incubating the plate at 37 C for 1 hour. The plates were washed and the bovine brain homogenate (diluted to 1% w/v in TBS) or rbPrP was added to designated wells and incubated at RT for 1 h. Wells were washed four times with TBST. pAbC2 was added to appropriate wells and incubated at RT or 1 hour, followed by a further 45 minute incubation with 100 ul of an anti-rabbit or mouse IgG/horseradish peroxidase conjugate (1:5000) in TBST containing 1% nonfat milk. Wells were washed four times with TBST. Signals were developed with TMB/H2O2 as a substrate for peroxidase. Reactions were stopped after 15 minutes by the addition of 100 ul of 2M phosphoric acid. Signals were monitored at 450 nm with reference at 620 nm using a SLT microplate reader. Specific positive signals were determined by comparing PrP binding to PC2 with PrP binding to the negative control, Mek-4 or milk. Preimmune controls showed no binding.

It will thus be appreciated that various antibodies that recognize and bind selectively to the YYR epitope unique to misfolded PrP c (shown herein above using an aggregated form known as PrP$^{Sc}$) can be identified be obtained by first applying the present epitope prediction methods to identify useful epitopes, and then raising antibodies against those epitopes in accordance with standard practices well established for these purposes.

Example 5—Human PrP—YML

As shown in Table 1, the epitope prediction method predicts the unfolding of a region of beta strand 1 in the human prion protein, PrP$^C$, a region that contains the epitope designated YML as shown by peptides LGGYML and GGYMLGS of SEQ ID Nos 1 and 2, respectively. In the experiment that follows, the monoclonal IgM antibody 1A1 is raised specifically against the YML epitope using, as antigen/immunogen, a peptide having the sequence GGYMLGS (beta strand one with two flanking residues N and C terminal, SEQ ID No.2).

General references: 263K hamster-adapted prions are described by Kimberlin et al., 1978. RML mouse-adapted prions are described by Chandler, R. L. (1961) (Lancet 1, 1378-1379). These may be used to infect mice or hamsters, using methods known in the art, for example those of Bueler H et al., 1993 (Cell 73:1339-1347), Oldstone et al., 2002, or Meade-White et al., 2009. Bolton et al., 1987 describe methods that may be used for isolation and purification of scrapie agent. Carlson et al., 1986 (Cell, 46:503-511) describes methods that may be used for clinical diagnosis of scrapie in mice and hamsters. Various transgenic mice overexpressing, partially expressing or lacking expression of PrP are described by Fischer et al., 1996 (EMBO J 15:1255-1264) and Weissmann et al., 2003 (British Medical Bulletin 66:43-60).

Brain and Spleen Homogenate Preparation

Brain tissues (normal and scrapie-infected mouse or hamster) were processed and analyzed as modified from Fischer et al 2000 (Nature 408:479-483). Briefly, 10% homogenates were made in PBS, 0.5% deoxycholate (Sigma), 0.5% NP-40. The total protein concentration in the homogenate was determined by BCA assay (Pierce) and adjusted to 5 mg/ml with homogenization buffer. For detection of PK-resistant material, 1.5 μl of homogenate was incubated with, or without, 0.15 μg PK (Sigma) at 37° C. for 60 minutes. Digestion was halted by addition of 20 mM PMSF (Sigma).

Magnetic Bead Antibody Conjugation and Immunoprecipitation

Antibodies were conjugated to magnetic beads and used for immunoprecipitation experiments as modified from Paramithiotis, 2003. Briefly, $7\times10^8$ magnetic beads (in 1 ml PBS) (Dynal, Lake Success, New York) were coupled according to the manufacturer's instructions to: 1A1, 8B4, 4E4 or IgM isotype control. Conjugated beads were washed and blocked according to the manufacturer's recommendations, then resuspended in 1 ml of PBS.

10 μL of antibody-coupled beads were incubated with 1 μL of 10% brain homogenate in 6% detergent (3% Tween20 and 3% NP40 in PBS) for 3 hr at room temperature. Magnet-captured immune complexes were washed 3 times with 4% detergent (2% Tween20 and 2% NP40 in PBS), boiled in 4% SDS without reducing agents, and resolved on 15% Trisglycine or 4-12% bis-tris acrylamide gels (Invitrogen).

Immunoblotting

Immunoblotting was performed as described (Paramithiotis et al., 2003). Proteins were transferred onto PVDF membranes (Invitrogen). Membranes were blocked with 5% (w/v) dried non-fat milk. All incubations were done in TBST (25 mM Tris-HCl, 0.2 M NaCl, 0.5% Tween-20). Peroxidase activity was detected by chemiluminescence; enhanced ECL (Amersham) or superWest Dura (Pierce; Rockford, Ill.).

Immunoprecipitation of $PrP^{Sc}$

Immunoprecipitated samples were analyzed by Western blotting (FIG. 1) with 6D11-biotin as the primary antibody (1:5000) and Strep-HRP as the secondary antibody (1:5000). 8B4-bead acted as a positive control and was able to immunoprecipitate PrP from all the brain homogenate samples except the PrP Knocked Out mouse (K/O). Beads only, IgM-isotype-beads and 4E4-beads acted as negative controls and as expected, no PrP was immunoprecipitated, except two very faint bands in the RML and 263K lanes as immunoprecipitated by the 4E4. 1A1, an IgM antibody that was raised against the beta-1 strand of PrP, was able to immunoprecipitate scrapie prion proteins from both RML (mouse scrapie strain) and 263K (hamster scrapie strain). There is a faint band in the Tg20 lane possibly due to a small content of misfolded PrP in this Prnp overexpressing transgenic mouse brain. Our data indicated that 1A1 was able to recognize only the scrapie PrP, but not the wild type PrP in both mouse and hamster brain.

Example 6—YML Exposure on the Cell Surface of Tumors and as a Therapeutic Target for Cancer Immunotherapy The 1A1 antibody was tested for its ability to bind to both normal and tumor cells. As a control, the anti-PrPC antibody 6D11 was used to identify the level of expression of PrP on each cell type. The ability of antibodies to bind to cells was observed by flow cytometry using HUVEC (human umbilical vein endothelial cells) as the normal cell type. Data is shown for binding to eight types of tumor cells. Five of the cancer cells tested are immortalized cell lines from mice (B16—melanoma, NSC34—motor neuron/neuroblastoma hybrid) and humans (HL60—promylocytic leukemia, MO3.13—oligodendrocyte/muscle hybrid, SiHa—cervical carcinoma). The remaining cancer cells tested are primary tumor cells that have been propagated by the Living Tumor Laboratory (LTL) at the British Columbia Cancer Agency. Using proprietary technology, primary human tumors are propagated under the kidney capsules of immunodeficient mice. This allows the original tumor architecture and phenotype to remain consistent with the originally harvested tumor. The three tumors that have been tested for binding to the 1A1 antibody are LTL-013 (large diffuse B-Cell lymphoma), LTL-257 (colorectal sarcoma) and LTL-323 (melanoma).

By flow cytometry, the 1A1 YML monoclonal antibody shows minimal binding to normal HUVEC cells compared to an isotype IgM control. 1A1 also shows no detectable binding to HL60 myeloid leukemia compared to IgM isotype control. HUVECs and HL60 cells have moderate and high levels, respectively, of 6D11 immunoreactivity, indicating that YML exposure is not a simple function of prion protein expression. The 1A1 antibody also shows detectable binding to seven other human and mouse tumor cell lines and LTL human tumors, all of which also display detectable cell surface 6D11 prion protein immunoreactivity.

Antibody Efficacy in a Tumor Model

To determine if an anti-DSE antibody can modify tumor progression in vivo, the 1A1 antibody was tested for its ability to modify growth of a murine melanoma tumor (B16) in female C57Bl/6 mice. On day 0 of the study, $3 \times 10^5$ tumour cells were implanted subcutaneously into the flank of 12 mice. The mice were randomly assigned to two treatment groups. Group 1 was treated with PBS. Group 2 was treated with 1A1 antibody at 10 mg/kg. Mice were treated on days −1, 2 and 5.

Figure 5:
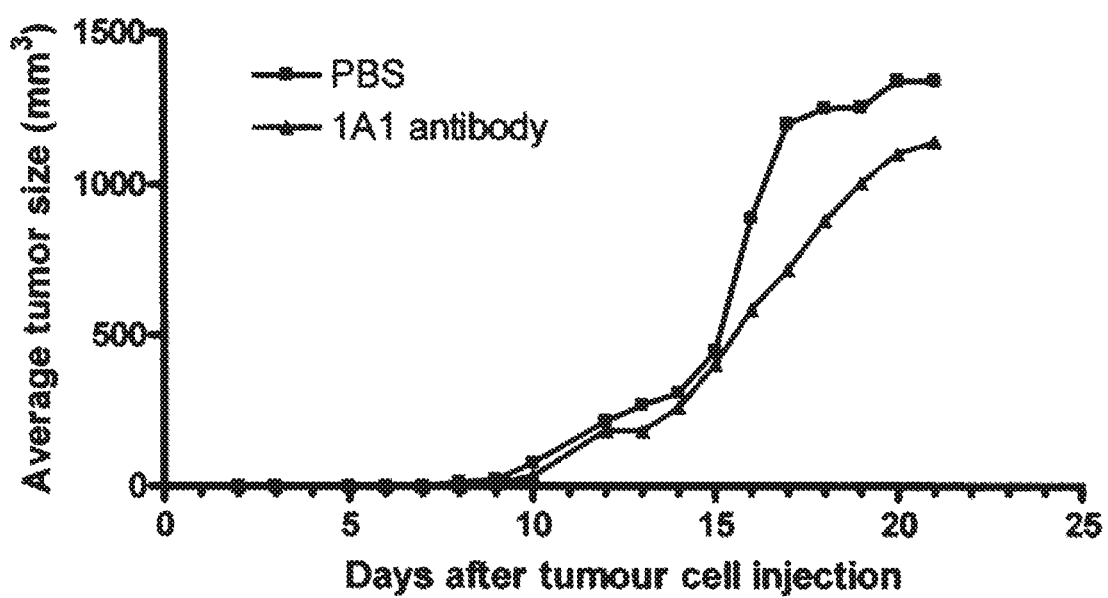
FIG. 5 is a graph showing the effect of treatment with the PrP YML-reactive 1A1 antibody on B16-F10 tumour bearing mice.

Tumour growth was monitored by measuring tumour dimensions with calipers beginning on day 2. Tumour length and width measurements were obtained and tumour volumes were calculated according to the equation $L \times W^2/2$ with the length (mm) being the longer axis of the tumour. Mice were sacrificed once tumour burden was high, according to standard animal care procedures. FIG. 5 shows the progression of tumour growth in both treatment groups in which the tumour volume prior to termination is carried through to the end. There is a significant difference in tumour growth between the two groups (paired t-test=0.012; Wilcoxin=0.007), indicating that a therapeutic effect of the 1A1 antibody has occurred.

All citations are herein incorporated by reference, as if each individual publication was specifically and individually indicated to be incorporated by reference herein and as though it were fully set forth herein. Citation of references herein is not to be construed nor considered as an admission that such references are prior art to the present invention.

One or more embodiments of the invention have been described by way of example. The invention includes all embodiments, modifications and variations substantially as hereinbefore described and with reference to the examples and figures. It will be apparent to persons skilled in the art that a number of variations and modifications can be made without departing from the scope of the invention as defined in the claims. Examples of such modifications include the substitution of known equivalents for any aspect of the invention in order to achieve the same result in substantially the same way.

We claim:

1. A method for obtaining an immunogen useful to produce an antibody that binds selectively to a misfolded form of a protein relative to the natively folded form of that protein, the method comprising:
  applying a method of operating a system to identify an epitope unique to a misfolded form of a protein of interest, the system comprising a processor and one or more memories coupled to the processor, the one or more memories containing instructions recorded thereon that, when executed by the processor, cause the processor to:
  (a) receive a model representing at least a portion of the structure of the protein of interest;
  (b) select one or more sets from the model, each set comprising one or more amino acid residues;
  (c) determine the free energy of unfolding of each set; and
  (d) identify the epitope by:
    (i) determining the total probability of unfolding of each set based on the free energy of unfolding of one or more of the sets in isolation, and identifying the epitope from the sets having a total probability of unfolding above a minimum probability; or
    (ii) identifying the epitope from the sets having a free energy of unfolding below a minimum energy;

wherein the identifying comprises storing data describing the epitope in the one or more memories of the system, or presenting graphical or numerical depiction of the epitope on a display or printed medium;

preparing a peptide comprising the epitope identified in step (d) by solid or solution phase synthesis; and isolating the peptide and producing the immunogen comprising the peptide that comprises the epitope unique to the misfolded form of the protein of interest.

2. The method of claim 1, wherein:

(a) the method further comprises receiving by the processor a selection of a region in the model; and (b) each of the one or more sets selected by the processor comprise at least one residue in the region.

3. The method of claim 1, wherein selecting by the processor one or more sets from the model comprises selecting all sets comprising a sequence of one or more contiguous amino acid residues in the model.

4. The method of claim 1, wherein selecting by the processor one or more sets from the model comprises selecting all sets comprising two or more non-contiguous sequences of one or more contiguous amino acid residues in the model.

5. The method of claim 3, wherein each sequence comprises a length between a minimum length and a maximum length.

6. The method of claim 1, wherein determining by the processor the free energy of unfolding of each set comprises determining the enthalpy of unfolding of the set by:

(a) determining the total number of pairs of polar atoms in the model that (i) are comprised of at least one polar atom in the set, (ii) are more than one amino acid residue apart in the amino acid sequence of the model, and (iii) are within a cutoff distance from one another; and (b) determining the enthalpy of unfolding of the set as the product of the total number of pairs determined in (a) by a fixed interaction energy.

7. The method of claim 1, wherein determining by the processor the free energy of unfolding of each set comprises determining the enthalpy of unfolding of the set by summing the results of solving the following equation for each pair of polar atoms in the model that are comprised of at least one atom in the set:

wherein:

$$\Delta H = \epsilon' \cos^4(\theta)\left(\left(\frac{1}{r}\right)^{10} - \beta\left(\frac{1}{r}\right)^{12}\right)$$

ΔH is enthalpy of unfolding of the pair of polar atoms;

$\acute{\varepsilon}$ is a fitting parameter;

θ is an angle between covalent bonds to carbon involving the polar atoms;

r is distance between the pair of polar atoms; and

β is a fitting parameter.

8. The method of claim 1, wherein determining by the processor the free energy of unfolding of each set comprises determining the enthalpy of unfolding of the set by:

(a) determining the solvent accessible surface area of the polar, nonpolar and hydroxyl functional groups that comprise the amino acid residues in the model;

(b) determining the solvent accessible surface area of the polar, nonpolar and hydroxyl functional groups that comprise the amino acid residues in the model with the set removed;

(c) determining the solvent accessible surface area of the polar, nonpolar and hydroxyl functional groups that comprise the amino acid residues of the set in isolation;

(d) determining the sum of the solvent accessible surface area of the polar functional groups determined in (b) and (c) minus the solvent accessible surface area of the polar functional groups determined in (a);

(e) determining the sum of the solvent accessible surface area of the nonpolar functional groups determined in (b) and (c) minus the solvent accessible surface area of the nonpolar functional groups determined in (a);

(f) determining the sum of the solvent accessible surface area of the hydroxyl functional groups determined in (b) and (c) minus the solvent accessible surface area of the hydroxyl functional groups determined in (a);

(g) determining the enthalpy of unfolding of the set by solving the following equation:

$$\Delta H(T) = (-8.44\Delta ASA_{nonpolar} + 31.4(\Delta ASA_{polar} + \Delta ASA_{hydroxyl}) - (60 - T)(0.45\Delta ASA_{nonpolar} - 0.26\Delta ASA_{polar} - 0.09\Delta ASA_{hydroxyl}))\frac{\text{cal}}{\text{mol}\cdot K}$$

wherein:

ΔH is change in enthalpy of unfolding of the set;

T is temperature;

$\Delta ASA_{polar}$ is change in solvent accessible surface area of the nonpolar functional groups determined in (d);

$\Delta ASA_{nonpolar}$ change in solvent accessible surface area of the nonpolar functional groups determined in (e); and $\Delta ASA_{hydroxyl}$ is change in solvent accessible surface area of the hydroxyl functional groups determined in (f).

9. The method of claim 1, wherein determining by the processor the free energy of unfolding of each set comprises determining the enthalpy of unfolding of the set by:
(a) simulating the motion of the model in a molecular dynamics simulation;
(b) summing the interaction energies between all pairs of amino acid residues in the model, wherein each pair comprises at least one amino acid residue in the set;
(c) simulating the motion of the model with the set in an unfolded state in a molecular dynamics simulation;
(d) summing the interaction energies between all pairs of amino acid residues in the set in the unfolded state; and
(e) subtracting the interaction energies determined in (d) from (b).

10. The method of claim 1, wherein determining by the processor the free energy of unfolding of each set comprises determining the free energy of breaking one or more salt bridges in the model by unfolding the set by determining the sum of the Coulombic energy between each pair of amino acid residues in the model, wherein each pair comprises at least one amino acid residue in the set, the Coulombic energy determined assuming a fixed permittivity within the protein.

11. The method of claim 1, wherein determining the free energy of unfolding of each set comprises determining the effects of one or more glycans on the free energy by solving the following equation:

$$\Delta G_{PTM} = -RT \ln\left(1 - \frac{a}{r_o}\left(1 - \text{erf}\left(\frac{a - r_o}{b\sqrt{(2/3)n}}\right)\right)\right)$$

wherein:
$\Delta G_{ptm}$ is effect of the glycans on the free energy of unfolding;
R is an ideal gas constant;
T is temperature;
a is a radius of the glycans;
$r_o$ is a starting position of the set around the glycans as measured from a center of the glycans;
erf is an error function;
b is a persistence length of the unfolded set; and
n is a number of residues in the unfolded set.

12. The method of claim 1, wherein determining the total probability of unfolding of each set based on the free energy of unfolding of one or more of the sets comprises, for each set, determining the sum of the equilibrium probabilities of unfolding of all of the sets comprising the amino acid residue sequence of the set, the equilibrium probability of unfolding of each set determined based on the free energy of unfolding of the set.

13. An immunogen, whenever produced by the method according to claim 1.

14. A method for obtaining an antibody that binds selectively to a misfolded form of a protein relative to the natively folded form of that protein, the method comprising:
(a) applying the method of operating a system as defined in claim 1 to identify an epitope unique to a misfolded form of said protein; and
(b) producing an antibody that binds selectively to said epitope, thereby obtaining an antibody that binds selectively to said misfolded form of said protein.

15. An antibody, whenever prepared by the method according to claim 14.

* * * * *

SEQUENCE LISTING

```
<160> NUMBER OF SEQ ID NOS: 91

<210> SEQ ID NO 1
<211> LENGTH: 6
<212> TYPE: PRT
<213> ORGANISM: Artificial sequence
<220> FEATURE:
<223> OTHER INFORMATION: Predicted epitope of a human prion protein

<400> SEQUENCE: 1

Leu Gly Gly Tyr Met Leu
1               5

<210> SEQ ID NO 2
<211> LENGTH: 7
<212> TYPE: PRT
<213> ORGANISM: Artificial sequence
<220> FEATURE:
<223> OTHER INFORMATION: Predicted epitope of a human prion protein

<400> SEQUENCE: 2

Gly Gly Tyr Met Leu Gly Ser
1               5

<210> SEQ ID NO 3
<211> LENGTH: 8
<212> TYPE: PRT
<213> ORGANISM: Homo sapiens
<220> FEATURE:
<223> OTHER INFORMATION: Predicted epitope of a human prion protein

<400> SEQUENCE: 3

His Phe Gly Ser Asp Tyr Glu Asp
1               5

<210> SEQ ID NO 4
<211> LENGTH: 5
<212> TYPE: PRT
<213> ORGANISM: Artificial sequence
```

```
<220> FEATURE:
<223> OTHER INFORMATION: Predicted epitope of a human prion protein

<400> SEQUENCE: 4

Ser Asp Tyr Glu Asp
1               5

<210> SEQ ID NO 5
<211> LENGTH: 8
<212> TYPE: PRT
<213> ORGANISM: Artificial sequence
<220> FEATURE:
<223> OTHER INFORMATION: Predicted epitope of a human prion protein

<400> SEQUENCE: 5

Arg Tyr Tyr Arg Glu Asn Met His
1               5

<210> SEQ ID NO 6
<211> LENGTH: 5
<212> TYPE: PRT
<213> ORGANISM: Artificial sequence
<220> FEATURE:
<223> OTHER INFORMATION: Predicted epitope of a human prion protein

<400> SEQUENCE: 6

Arg Glu Asn Met His
1               5

<210> SEQ ID NO 7
<211> LENGTH: 7
<212> TYPE: PRT
<213> ORGANISM: Artificial sequence
<220> FEATURE:
<223> OTHER INFORMATION: Predicted epitope of a human prion protein

<400> SEQUENCE: 7

Gln Val Tyr Tyr Arg Pro Met
1               5

<210> SEQ ID NO 8
<211> LENGTH: 10
<212> TYPE: PRT
<213> ORGANISM: Artificial sequence
<220> FEATURE:
<223> OTHER INFORMATION: Predicted epitope of a human prion protein

<400> SEQUENCE: 8

Pro Met Asp Glu Tyr Ser Asn Gln Asn Asn
1               5                   10

<210> SEQ ID NO 9
<211> LENGTH: 9
<212> TYPE: PRT
<213> ORGANISM: Artificial sequence
<220> FEATURE:
<223> OTHER INFORMATION: Predicted epitope of a human prion protein

<400> SEQUENCE: 9

Met Asp Glu Tyr Ser Asn Gln Asn Asn
1               5

<210> SEQ ID NO 10
<211> LENGTH: 13
<212> TYPE: PRT
<213> ORGANISM: Artificial sequence
```

```
<220> FEATURE:
<223> OTHER INFORMATION: Predicted epitope of a human prion protein

<400> SEQUENCE: 10

Lys Gln His Thr Val Thr Thr Thr Thr Lys Gly Glu Asn
1               5                   10

<210> SEQ ID NO 11
<211> LENGTH: 9
<212> TYPE: PRT
<213> ORGANISM: Artificial sequence
<220> FEATURE:
<223> OTHER INFORMATION: Predicted epitope of a bovine prion protein

<400> SEQUENCE: 11

His Phe Gly Ser Asp Tyr Glu Asp Arg
1               5

<210> SEQ ID NO 12
<211> LENGTH: 16
<212> TYPE: PRT
<213> ORGANISM: Artificial sequence
<220> FEATURE:
<223> OTHER INFORMATION: Predicted epitope of a bovine prion protein

<400> SEQUENCE: 12

Ile His Phe Gly Ser Asp Tyr Glu Arg Tyr Tyr Arg Glu Asn Met His
1               5                   10                  15

<210> SEQ ID NO 13
<211> LENGTH: 9
<212> TYPE: PRT
<213> ORGANISM: Artificial sequence
<220> FEATURE:
<223> OTHER INFORMATION: Predicted epitope of a bovine prion protein

<400> SEQUENCE: 13

Val Asp Gln Tyr Ser Asn Gln Asn Asn
1               5

<210> SEQ ID NO 14
<211> LENGTH: 11
<212> TYPE: PRT
<213> ORGANISM: Artificial sequence
<220> FEATURE:
<223> OTHER INFORMATION: Predicted epitope of a bovine prion protein

<400> SEQUENCE: 14

His Thr Val Thr Thr Thr Thr Lys Gly Glu Asn
1               5                   10

<210> SEQ ID NO 15
<211> LENGTH: 5
<212> TYPE: PRT
<213> ORGANISM: Artificial sequence
<220> FEATURE:
<223> OTHER INFORMATION: Predicted epitope of a bovine prion protein

<400> SEQUENCE: 15

Gln Tyr Gln Arg Glu
1               5

<210> SEQ ID NO 16
<211> LENGTH: 7
<212> TYPE: PRT
<213> ORGANISM: Artificial sequence
```

```
<220> FEATURE:
<223> OTHER INFORMATION: Predicted epitope of human transthyretin

<400> SEQUENCE: 16

Leu Asp Ala Val Arg Gly Ser
1               5

<210> SEQ ID NO 17
<211> LENGTH: 10
<212> TYPE: PRT
<213> ORGANISM: Artificial sequence
<220> FEATURE:
<223> OTHER INFORMATION: Predicted epitope of human transthyretin

<400> SEQUENCE: 17

Phe Arg Lys Ala Ala Asp Asp Thr Trp Glu
1               5                   10

<210> SEQ ID NO 18
<211> LENGTH: 11
<212> TYPE: PRT
<213> ORGANISM: Artificial sequence
<220> FEATURE:
<223> OTHER INFORMATION: Predicted epitope of human transthyretin

<400> SEQUENCE: 18

Ser Gly Lys Thr Ser Glu Ser Gly Glu Leu His
1               5                   10

<210> SEQ ID NO 19
<211> LENGTH: 6
<212> TYPE: PRT
<213> ORGANISM: Artificial sequence
<220> FEATURE:
<223> OTHER INFORMATION: Predicted epitope of human transthyretin

<400> SEQUENCE: 19

Leu Thr Thr Glu Glu Gln
1               5

<210> SEQ ID NO 20
<211> LENGTH: 11
<212> TYPE: PRT
<213> ORGANISM: Artificial sequence
<220> FEATURE:
<223> OTHER INFORMATION: Predicted epitope of human transthyretin

<400> SEQUENCE: 20

Lys Ala Leu Gly Ile Ser Pro Phe His Glu His
1               5                   10

<210> SEQ ID NO 21
<211> LENGTH: 7
<212> TYPE: PRT
<213> ORGANISM: Artificial sequence
<220> FEATURE:
<223> OTHER INFORMATION: Predicted epitope of human transthyretin

<400> SEQUENCE: 21

Ala Asn Asp Ser Gly Pro Arg
1               5

<210> SEQ ID NO 22
<211> LENGTH: 7
<212> TYPE: PRT
<213> ORGANISM: Artificial sequence
```

```
<220> FEATURE:
<223> OTHER INFORMATION: Predicted epitope of human transthyretin

<400> SEQUENCE: 22

Ser Pro Tyr Ser Tyr Ser Thr
1               5

<210> SEQ ID NO 23
<211> LENGTH: 13
<212> TYPE: PRT
<213> ORGANISM: Artificial sequence
<220> FEATURE:
<223> OTHER INFORMATION: Predicted epitope of human beta-2 microglobulin

<400> SEQUENCE: 23

Tyr Ser Arg His Pro Ala Glu Asn Gly Lys Ser Asn Phe
1               5                   10

<210> SEQ ID NO 24
<211> LENGTH: 13
<212> TYPE: PRT
<213> ORGANISM: Artificial sequence
<220> FEATURE:
<223> OTHER INFORMATION: Predicted epitope of human beta-2 microglobulin

<400> SEQUENCE: 24

Leu Leu Lys Asn Gly Glu Arg Ile Glu Lys Val Glu His
1               5                   10

<210> SEQ ID NO 25
<211> LENGTH: 15
<212> TYPE: PRT
<213> ORGANISM: Artificial sequence
<220> FEATURE:
<223> OTHER INFORMATION: Predicted epitope of human beta-2 microglobulin

<400> SEQUENCE: 25

Val Glu His Ser Asp Leu Ser Phe Ser Lys Asp Trp Ser Phe Tyr
1               5                   10                  15

<210> SEQ ID NO 26
<211> LENGTH: 5
<212> TYPE: PRT
<213> ORGANISM: Artificial sequence
<220> FEATURE:
<223> OTHER INFORMATION: Predicted epitope of human beta-2 microglobulin

<400> SEQUENCE: 26

Thr Glu Lys Asp Glu
1               5

<210> SEQ ID NO 27
<211> LENGTH: 11
<212> TYPE: PRT
<213> ORGANISM: Artificial sequence
<220> FEATURE:
<223> OTHER INFORMATION: Predicted epitopes of human Cu/Zn superoxide
      dismutase

<400> SEQUENCE: 27

Val Cys Val Leu Lys Gly Asp Gly Pro Val Gln
1               5                   10

<210> SEQ ID NO 28
<211> LENGTH: 8
<212> TYPE: PRT
<213> ORGANISM: Artificial sequence
```

```
<220> FEATURE:
<223> OTHER INFORMATION: Predicted epitopes of human Cu/Zn superoxide
      dismutase

<400> SEQUENCE: 28

Lys Gly Asp Gly Pro Val Gln Gly
1               5

<210> SEQ ID NO 29
<211> LENGTH: 7
<212> TYPE: PRT
<213> ORGANISM: Artificial sequence
<220> FEATURE:
<223> OTHER INFORMATION: Predicted epitopes of human Cu/Zn superoxide
      dismutase

<400> SEQUENCE: 29

Glu Gln Lys Glu Ser Asn Gly
1               5

<210> SEQ ID NO 30
<211> LENGTH: 7
<212> TYPE: PRT
<213> ORGANISM: Artificial sequence
<220> FEATURE:
<223> OTHER INFORMATION: Predicted epitopes of human Cu/Zn superoxide
      dismutase

<400> SEQUENCE: 30

Ile Lys Gly Leu Thr Glu Gly
1               5

<210> SEQ ID NO 31
<211> LENGTH: 10
<212> TYPE: PRT
<213> ORGANISM: Artificial sequence
<220> FEATURE:
<223> OTHER INFORMATION: Predicted epitopes of human Cu/Zn superoxide
      dismutase

<400> SEQUENCE: 31

Phe Gly Asp Asn Thr Ala Gly Cys Thr Ser
1               5                   10

<210> SEQ ID NO 32
<211> LENGTH: 11
<212> TYPE: PRT
<213> ORGANISM: Artificial sequence
<220> FEATURE:
<223> OTHER INFORMATION: Predicted epitopes of human Cu/Zn superoxide
      dismutase

<400> SEQUENCE: 32

Phe Gly Asp Asn Thr Ala Gly Cys Thr Ser Ala
1               5                   10

<210> SEQ ID NO 33
<211> LENGTH: 9
<212> TYPE: PRT
<213> ORGANISM: Artificial sequence
<220> FEATURE:
<223> OTHER INFORMATION: Predicted epitopes of human Cu/Zn superoxide
      dismutase

<400> SEQUENCE: 33

Asn Val Thr Ala Asp Lys Asp Gly Val
1               5
```

```
<210> SEQ ID NO 34
<211> LENGTH: 9
<212> TYPE: PRT
<213> ORGANISM: Artificial sequence
<220> FEATURE:
<223> OTHER INFORMATION: Predicted epitopes of human Cu/Zn superoxide
      dismutase

<400> SEQUENCE: 34

Val Thr Ala Asp Lys Asp Gly Val Ala
1               5

<210> SEQ ID NO 35
<211> LENGTH: 5
<212> TYPE: PRT
<213> ORGANISM: Artificial sequence
<220> FEATURE:
<223> OTHER INFORMATION: Predicted epitopes of human Cu/Zn superoxide
      dismutase

<400> SEQUENCE: 35

Leu Ser Gly Asp His
1               5

<210> SEQ ID NO 36
<211> LENGTH: 8
<212> TYPE: PRT
<213> ORGANISM: Artificial sequence
<220> FEATURE:
<223> OTHER INFORMATION: Predicted epitopes of human Cu/Zn superoxide
      dismutase

<400> SEQUENCE: 36

Ser Leu Ser Gly Asp His Cys Ile
1               5

<210> SEQ ID NO 37
<211> LENGTH: 6
<212> TYPE: PRT
<213> ORGANISM: Artificial sequence
<220> FEATURE:
<223> OTHER INFORMATION: Predicted epitopes of human Cu/Zn superoxide
      dismutase

<400> SEQUENCE: 37

Glu Glu Ser Thr Lys Thr
1               5

<210> SEQ ID NO 38
<211> LENGTH: 7
<212> TYPE: PRT
<213> ORGANISM: Artificial sequence
<220> FEATURE:
<223> OTHER INFORMATION: Predicted epitopes of human Cu/Zn superoxide
      dismutase

<400> SEQUENCE: 38

Glu Ser Thr Lys Thr Gly Asn
1               5

<210> SEQ ID NO 39
<211> LENGTH: 6
<212> TYPE: PRT
<213> ORGANISM: Artificial sequence
<220> FEATURE:
<223> OTHER INFORMATION: Predicted epitopes of human Cu/Zn superoxide
      dismutase
```

```
<400> SEQUENCE: 39

Arg Leu Ala Cys Gly Val
1               5

<210> SEQ ID NO 40
<211> LENGTH: 11
<212> TYPE: PRT
<213> ORGANISM: Artificial sequence
<220> FEATURE:
<223> OTHER INFORMATION: Predicted epitopes of human Cu/Zn superoxide
      dismutase
<220> FEATURE:
<221> NAME/KEY: misc_feature
<222> LOCATION: (4)..(4)
<223> OTHER INFORMATION: Xaa is cysteic acid

<400> SEQUENCE: 40

Arg Leu Ala Xaa Gly Val Ile Gly Ile Ala Gln
1               5                   10

<210> SEQ ID NO 41
<211> LENGTH: 15
<212> TYPE: PRT
<213> ORGANISM: Artificial sequence
<220> FEATURE:
<223> OTHER INFORMATION: Predicted epitope of human CD38

<400> SEQUENCE: 41

Tyr Thr Glu Ile His Pro Glu Met Arg His Val Asp Cys Gln Ser
1               5                   10                  15

<210> SEQ ID NO 42
<211> LENGTH: 9
<212> TYPE: PRT
<213> ORGANISM: Artificial sequence
<220> FEATURE:
<223> OTHER INFORMATION: Predicted epitope of human CD38

<400> SEQUENCE: 42

Gly Glu Phe Ala Thr Ser Lys Ile Asn
1               5

<210> SEQ ID NO 43
<211> LENGTH: 7
<212> TYPE: PRT
<213> ORGANISM: Artificial sequence
<220> FEATURE:
<223> OTHER INFORMATION: Predicted epitope of human CD38

<400> SEQUENCE: 43

Trp Arg Lys Asp Cys Ser Asn
1               5

<210> SEQ ID NO 44
<211> LENGTH: 11
<212> TYPE: PRT
<213> ORGANISM: Artificial sequence
<220> FEATURE:
<223> OTHER INFORMATION: Predicted epitope of human CD38

<400> SEQUENCE: 44

Gly Ser Arg Ser Lys Ile Phe Asp Lys Asp Ser
1               5                   10
```

```
<210> SEQ ID NO 45
<211> LENGTH: 11
<212> TYPE: PRT
<213> ORGANISM: Artificial sequence
<220> FEATURE:
<223> OTHER INFORMATION: Predicted epitope of human CD38

<400> SEQUENCE: 45

Ile His Gly Gly Arg Glu Asp Ser Arg Asp Leu
1               5                   10

<210> SEQ ID NO 46
<211> LENGTH: 7
<212> TYPE: PRT
<213> ORGANISM: Artificial sequence
<220> FEATURE:
<223> OTHER INFORMATION: Predicted epitope of human CD44

<400> SEQUENCE: 46

Asn Gly Arg Tyr Ser Ile Ser
1               5

<210> SEQ ID NO 47
<211> LENGTH: 5
<212> TYPE: PRT
<213> ORGANISM: Artificial sequence
<220> FEATURE:
<223> OTHER INFORMATION: Predicted epitope of human CD44

<400> SEQUENCE: 47

Glu Gly His Val Val
1               5

<210> SEQ ID NO 48
<211> LENGTH: 9
<212> TYPE: PRT
<213> ORGANISM: Artificial sequence
<220> FEATURE:
<223> OTHER INFORMATION: Predicted epitope of human CD44

<400> SEQUENCE: 48

Thr Ser Asn Thr Ser Asn Tyr Asp Thr
1               5

<210> SEQ ID NO 49
<211> LENGTH: 11
<212> TYPE: PRT
<213> ORGANISM: Artificial sequence
<220> FEATURE:
<223> OTHER INFORMATION: Predicted epitope of human CD44

<400> SEQUENCE: 49

Asn Arg Asp Gly Thr Arg Tyr Val Gln Lys Gly
1               5                   10

<210> SEQ ID NO 50
<211> LENGTH: 18
<212> TYPE: PRT
<213> ORGANISM: Artificial sequence
<220> FEATURE:
<223> OTHER INFORMATION: Predicted epitope of human CD44

<400> SEQUENCE: 50

Ala Asn Asn Thr Phe Val Tyr Ile Leu Thr Ser Asn Thr Ser Asn Tyr
1               5                   10                  15

Asp Thr
```

```
<210> SEQ ID NO 51
<211> LENGTH: 11
<212> TYPE: PRT
<213> ORGANISM: Artificial sequence
<220> FEATURE:
<223> OTHER INFORMATION: Predicted epitope of human tumour necrosis
      factor receptor

<400> SEQUENCE: 51

Ile His Pro Gln Asn Asn Ser Ile Cys Cys Thr
1               5                   10

<210> SEQ ID NO 52
<211> LENGTH: 11
<212> TYPE: PRT
<213> ORGANISM: Artificial sequence
<220> FEATURE:
<223> OTHER INFORMATION: Predicted epitope of human tumour necrosis
      factor receptor

<400> SEQUENCE: 52

Asn Asp Cys Pro Gly Pro Gly Gln Asp Thr Asp
1               5                   10

<210> SEQ ID NO 53
<211> LENGTH: 7
<212> TYPE: PRT
<213> ORGANISM: Artificial sequence
<220> FEATURE:
<223> OTHER INFORMATION: Predicted epitope of human tumour necrosis
      factor receptor

<400> SEQUENCE: 53

Tyr Trp Ser Glu Asn Leu Phe
1               5

<210> SEQ ID NO 54
<211> LENGTH: 9
<212> TYPE: PRT
<213> ORGANISM: Artificial sequence
<220> FEATURE:
<223> OTHER INFORMATION: Predicted epitope of human tumour necrosis
      factor receptor

<400> SEQUENCE: 54

His Leu Ser Cys Gln Glu Lys Gln Asn
1               5

<210> SEQ ID NO 55
<211> LENGTH: 15
<212> TYPE: PRT
<213> ORGANISM: Artificial sequence
<220> FEATURE:
<223> OTHER INFORMATION: Predicted epitope of human tumour necrosis
      factor receptor

<400> SEQUENCE: 55

Cys Thr Cys His Ala Gly Phe Phe Leu Arg Glu Asn Glu Cys Val
1               5                   10                  15

<210> SEQ ID NO 56
<211> LENGTH: 7
<212> TYPE: PRT
<213> ORGANISM: Artificial sequence
<220> FEATURE:
<223> OTHER INFORMATION: Predicted epitope of human notch protein
```

```
<400> SEQUENCE: 56

Cys Glu His Ala Gly Lys Cys
 1               5

<210> SEQ ID NO 57
<211> LENGTH: 9
<212> TYPE: PRT
<213> ORGANISM: Artificial sequence
<220> FEATURE:
<223> OTHER INFORMATION: Predicted epitope of human notch protein

<400> SEQUENCE: 57

Met Pro Gly Tyr Glu Gly Val His Cys
 1               5

<210> SEQ ID NO 58
<211> LENGTH: 7
<212> TYPE: PRT
<213> ORGANISM: Artificial sequence
<220> FEATURE:
<223> OTHER INFORMATION: Predicted epitope of human notch protein

<400> SEQUENCE: 58

Cys Leu His Asn Gly Arg Cys
 1               5

<210> SEQ ID NO 59
<211> LENGTH: 5
<212> TYPE: PRT
<213> ORGANISM: Artificial sequence
<220> FEATURE:
<223> OTHER INFORMATION: Predicted epitope of human notch protein

<400> SEQUENCE: 59

Lys Ile Asn Glu Phe
 1               5

<210> SEQ ID NO 60
<211> LENGTH: 25
<212> TYPE: PRT
<213> ORGANISM: Artificial sequence
<220> FEATURE:
<223> OTHER INFORMATION: Predicted epitope of human notch protein

<400> SEQUENCE: 60

Glu Cys Ala Ser Ser Pro Cys Leu His Asn Gly Arg Cys Leu Asp Lys
 1               5                  10                  15

Ile Asn Glu Phe Gln Cys Glu Cys Pro
             20                  25

<210> SEQ ID NO 61
<211> LENGTH: 9
<212> TYPE: PRT
<213> ORGANISM: Artificial sequence
<220> FEATURE:
<223> OTHER INFORMATION: Predicted epitope of human FAS

<400> SEQUENCE: 61

Leu His His Asp Gly Gln Phe Cys His
 1               5

<210> SEQ ID NO 62
<211> LENGTH: 11
<212> TYPE: PRT
<213> ORGANISM: Artificial sequence
```

```
<220> FEATURE:
<223> OTHER INFORMATION: Predicted epitope of human FAS

<400> SEQUENCE: 62

Ala Arg Asp Cys Thr Val Asn Gly Asp Glu Pro
1               5                   10

<210> SEQ ID NO 63
<211> LENGTH: 7
<212> TYPE: PRT
<213> ORGANISM: Artificial sequence
<220> FEATURE:
<223> OTHER INFORMATION: Predicted epitope of human FAS

<400> SEQUENCE: 63

Arg Leu Cys Asp Glu Gly His
1               5

<210> SEQ ID NO 64
<211> LENGTH: 7
<212> TYPE: PRT
<213> ORGANISM: Artificial sequence
<220> FEATURE:
<223> OTHER INFORMATION: Predicted epitope of human FAS

<400> SEQUENCE: 64

Asn Ser Thr Val Cys Glu His
1               5

<210> SEQ ID NO 65
<211> LENGTH: 13
<212> TYPE: PRT
<213> ORGANISM: Artificial sequence
<220> FEATURE:
<223> OTHER INFORMATION: Predicted epitope of human FAS

<400> SEQUENCE: 65

Glu Glu Pro Ser Arg Ser Asn Leu Gly Trp Leu Cys Leu
1               5                   10

<210> SEQ ID NO 66
<211> LENGTH: 15
<212> TYPE: PRT
<213> ORGANISM: Artificial sequence
<220> FEATURE:
<223> OTHER INFORMATION: Predicted epitope of human epidermal growth
      factor receptor

<400> SEQUENCE: 66

Ser Asn Lys Leu Thr Gln Leu Phe Thr Phe Glu Asp His Phe Leu
1               5                   10                  15

<210> SEQ ID NO 67
<211> LENGTH: 11
<212> TYPE: PRT
<213> ORGANISM: Artificial sequence
<220> FEATURE:
<223> OTHER INFORMATION: Predicted epitope of human epidermal growth
      factor receptor

<400> SEQUENCE: 67

Val Gln Arg Asn Tyr Asp Leu Ser Phe Leu Lys
1               5                   10
```

```
<210> SEQ ID NO 68
<211> LENGTH: 13
<212> TYPE: PRT
<213> ORGANISM: Artificial sequence
<220> FEATURE:
<223> OTHER INFORMATION: Predicted epitope of human epidermal growth
      factor receptor

<400> SEQUENCE: 68

Ile Arg Gly Asn Met Tyr Tyr Glu Asn Ser Tyr Ala Leu
1               5                   10

<210> SEQ ID NO 69
<211> LENGTH: 11
<212> TYPE: PRT
<213> ORGANISM: Artificial sequence
<220> FEATURE:
<223> OTHER INFORMATION: Predicted epitope of human epidermal growth
      factor receptor

<400> SEQUENCE: 69

Val Leu Ser Asn Tyr Asp Ala Asn Lys Thr Gly
1               5                   10

<210> SEQ ID NO 70
<211> LENGTH: 13
<212> TYPE: PRT
<213> ORGANISM: Artificial sequence
<220> FEATURE:
<223> OTHER INFORMATION: Predicted epitope of human epidermal growth
      factor receptor

<400> SEQUENCE: 70

Ile Val Ser Ser Asp Phe Leu Ser Asn Met Ser Met Asp
1               5                   10

<210> SEQ ID NO 71
<211> LENGTH: 15
<212> TYPE: PRT
<213> ORGANISM: Artificial sequence
<220> FEATURE:
<223> OTHER INFORMATION: Predicted epitope of human epidermal growth
      factor receptor

<400> SEQUENCE: 71

Phe Leu Ser Asn Met Ser Met Asp Phe Gln Asn His Leu Gly Ser
1               5                   10                  15

<210> SEQ ID NO 72
<211> LENGTH: 6
<212> TYPE: PRT
<213> ORGANISM: Artificial sequence
<220> FEATURE:
<223> OTHER INFORMATION: Predicted epitope of human epidermal growth
      factor receptor

<400> SEQUENCE: 72

Trp Gly Ala Gly Glu Glu
1               5

<210> SEQ ID NO 73
<211> LENGTH: 18
<212> TYPE: PRT
<213> ORGANISM: Artificial sequence
<220> FEATURE:
<223> OTHER INFORMATION: Predicted epitope of human epidermal growth
      factor receptor
```

```
<400> SEQUENCE: 73

Pro Pro Leu Met Leu Tyr Asn Pro Thr Thr Tyr Gln Met Asp Val Asn
1               5                   10                  15

Pro Glu

<210> SEQ ID NO 74
<211> LENGTH: 10
<212> TYPE: PRT
<213> ORGANISM: Artificial sequence
<220> FEATURE:
<223> OTHER INFORMATION: Predicted epitope of human epidermal growth
      factor receptor

<400> SEQUENCE: 74

Pro Glu Gly Lys Tyr Ser Phe Gly Ala Thr
1               5                   10

<210> SEQ ID NO 75
<211> LENGTH: 10
<212> TYPE: PRT
<213> ORGANISM: Artificial sequence
<220> FEATURE:
<223> OTHER INFORMATION: Predicted epitope of human epidermal growth
      factor receptor

<400> SEQUENCE: 75

Arg Asn Tyr Val Val Thr Asp His Gly Ser
1               5                   10

<210> SEQ ID NO 76
<211> LENGTH: 14
<212> TYPE: PRT
<213> ORGANISM: Artificial sequence
<220> FEATURE:
<223> OTHER INFORMATION: Predicted epitope of human epidermal growth
      factor receptor

<400> SEQUENCE: 76

Gly Ala Asp Ser Tyr Glu Met Glu Glu Asp Gly Val Arg Lys
1               5                   10

<210> SEQ ID NO 77
<211> LENGTH: 15
<212> TYPE: PRT
<213> ORGANISM: Artificial sequence
<220> FEATURE:
<223> OTHER INFORMATION: Predicted epitope of human epidermal growth
      factor receptor

<400> SEQUENCE: 77

Asn Gly Ile Gly Ile Gly Glu Phe Lys Asp Ser Leu Ser Ile Asn
1               5                   10                  15

<210> SEQ ID NO 78
<211> LENGTH: 9
<212> TYPE: PRT
<213> ORGANISM: Artificial sequence
<220> FEATURE:
<223> OTHER INFORMATION: Predicted epitope of human epidermal growth
      factor receptor

<400> SEQUENCE: 78

Ala Thr Asn Ile Lys His Phe Lys Asn
1               5
```

```
<210> SEQ ID NO 79
<211> LENGTH: 16
<212> TYPE: PRT
<213> ORGANISM: Artificial sequence
<220> FEATURE:
<223> OTHER INFORMATION: Predicted epitope of human epidermal growth
      factor receptor

<400> SEQUENCE: 79

Leu Pro Val Ala Phe Arg Gly Asp Ser Phe Thr His Thr Pro Pro Leu
1               5                   10                  15

<210> SEQ ID NO 80
<211> LENGTH: 10
<212> TYPE: PRT
<213> ORGANISM: Artificial sequence
<220> FEATURE:
<223> OTHER INFORMATION: Predicted epitope of human epidermal growth
      factor receptor

<400> SEQUENCE: 80

Lys Ile Ile Ser Asn Arg Gly Glu Asn Ser
1               5                   10

<210> SEQ ID NO 81
<211> LENGTH: 7
<212> TYPE: PRT
<213> ORGANISM: Artificial sequence
<220> FEATURE:
<223> OTHER INFORMATION: Synthesized

<400> SEQUENCE: 81

Gly Gly Tyr Met Leu Gly Ser
1               5

<210> SEQ ID NO 82
<211> LENGTH: 6
<212> TYPE: PRT
<213> ORGANISM: Artificial sequence
<220> FEATURE:
<223> OTHER INFORMATION: Synthesized

<400> SEQUENCE: 82

Gly Gly Tyr Met Leu Gly
1               5

<210> SEQ ID NO 83
<211> LENGTH: 6
<212> TYPE: PRT
<213> ORGANISM: Artificial sequence
<220> FEATURE:
<223> OTHER INFORMATION: Synthesized

<400> SEQUENCE: 83

Gly Tyr Met Leu Gly Ser
1               5

<210> SEQ ID NO 84
<211> LENGTH: 5
<212> TYPE: PRT
<213> ORGANISM: Artificial sequence
<220> FEATURE:
<223> OTHER INFORMATION: Synthesized

<400> SEQUENCE: 84

Gly Gly Tyr Met Leu
1               5
```

```
<210> SEQ ID NO 85
<211> LENGTH: 5
<212> TYPE: PRT
<213> ORGANISM: Artificial sequence
<220> FEATURE:
<223> OTHER INFORMATION: Synthesized

<400> SEQUENCE: 85

Tyr Met Leu Gly Ser
1               5

<210> SEQ ID NO 86
<211> LENGTH: 4
<212> TYPE: PRT
<213> ORGANISM: Artificial sequence
<220> FEATURE:
<223> OTHER INFORMATION: Synthesized

<400> SEQUENCE: 86

Gly Tyr Met Leu
1

<210> SEQ ID NO 87
<211> LENGTH: 4
<212> TYPE: PRT
<213> ORGANISM: Artificial sequence
<220> FEATURE:
<223> OTHER INFORMATION: Synthesized

<400> SEQUENCE: 87

Tyr Met Leu Gly
1

<210> SEQ ID NO 88

<400> SEQUENCE: 88

000

<210> SEQ ID NO 89
<211> LENGTH: 11
<212> TYPE: PRT
<213> ORGANISM: Artificial sequence
<220> FEATURE:
<223> OTHER INFORMATION: hSOD1 epitope

<400> SEQUENCE: 89

Ile Lys Gly Leu Thr Glu Gly Leu His Gly Phe
1               5                   10

<210> SEQ ID NO 90
<211> LENGTH: 10
<212> TYPE: PRT
<213> ORGANISM: Artificial sequence
<220> FEATURE:
<223> OTHER INFORMATION: YYR peptides

<400> SEQUENCE: 90

Cys Tyr Tyr Arg Arg Tyr Tyr Arg Tyr Tyr
1               5                   10

<210> SEQ ID NO 91
<211> LENGTH: 10
<212> TYPE: PRT
<213> ORGANISM: Artificial sequence
<220> FEATURE:
<223> OTHER INFORMATION: YYR peptide
```

```
<400> SEQUENCE: 91

Cys Lys Tyr Glu Asp Arg Tyr Tyr Arg Glu
1               5                   10
```